(12) United States Patent
Masakari et al.

(10) Patent No.: US 10,619,183 B2
(45) Date of Patent: Apr. 14, 2020

(54) MODIFIED AMADORIASE AND METHOD FOR PRODUCING THE SAME, AGENT FOR IMPROVING SURFACTANT RESISTANCE OF AMADORIASE AND COMPOSITION FOR MEASURING HBA1C USING THE SAME

(71) Applicant: Kikkoman Corporation, Noda-shi, Chiba (JP)

(72) Inventors: Yosuke Masakari, Noda (JP); Atsushi Ichiyanagi, Noda (JP)

(73) Assignee: Kikkoman Corporation, Chiba (JP)

( * ) Notice: Subject to any disclaimer, the term of this patent is extended or adjusted under 35 U.S.C. 154(b) by 308 days.

(21) Appl. No.: 14/910,789

(22) PCT Filed: Aug. 8, 2014

(86) PCT No.: PCT/JP2014/071036
§ 371 (c)(1),
(2) Date: Feb. 8, 2016

(87) PCT Pub. No.: WO2015/020200
PCT Pub. Date: Feb. 12, 2015

(65) Prior Publication Data
US 2016/0186232 A1 Jun. 30, 2016

(30) Foreign Application Priority Data

Aug. 9, 2013 (JP) ................. 2013-167005
Oct. 24, 2013 (JP) ................. 2013-221515

(51) Int. Cl.
| C12Q 1/26 | (2006.01) |
|---|---|
| C12N 9/06 | (2006.01) |
| G01N 33/72 | (2006.01) |

(52) U.S. Cl.
CPC ............ *C12Q 1/26* (2013.01); *C12N 9/0032* (2013.01); *G01N 33/723* (2013.01); *C12Y 105/03* (2013.01); *G01N 2333/805* (2013.01); *G01N 2333/90672* (2013.01)

(58) Field of Classification Search
None
See application file for complete search history.

(56) References Cited

U.S. PATENT DOCUMENTS

| 5,370,990 | A | 12/1994 | Staniford et al. |
|---|---|---|---|
| 7,070,948 | B1 | 7/2006 | Sakaue et al. |
| 2003/0162242 | A1 | 8/2003 | Yonehara |
| 2005/0101771 | A1 | 5/2005 | Kouzuma et al. |
| 2007/0154976 | A1 | 7/2007 | Taniguchi et al. |
| 2007/0178547 | A1 | 8/2007 | Taniguchi et al. |
| 2008/0113381 | A1 | 5/2008 | Matsuoka et al. |
| 2008/0233605 | A1 | 9/2008 | Taniguchi et al. |
| 2008/0295259 | A1 | 12/2008 | Ueda et al. |
| 2010/0330013 | A1* | 12/2010 | O'Connell ............... A61K 8/66 424/62 |
| 2011/0003361 | A1 | 1/2011 | Kurosawa et al. |
| 2011/0195444 | A1 | 8/2011 | Hirao et al. |
| 2012/0208226 | A1 | 8/2012 | Ikebukuro et al. |
| 2013/0171676 | A1 | 7/2013 | Murakami et al. |
| 2013/0267007 | A1 | 10/2013 | Ichiyanagi et al. |
| 2014/0234886 | A1 | 8/2014 | Aisaka et al. |
| 2015/0132786 | A1 | 5/2015 | Soya |

FOREIGN PATENT DOCUMENTS

| EP | 1878801 A1 | 1/2008 |
|---|---|---|
| EP | 2281900 A1 | 2/2011 |
| EP | 2808386 A1 | 12/2014 |
| JP | 05-033997 B2 | 5/1993 |
| JP | 11-127895 A | 5/1999 |
| JP | 2001-095598 A | 4/2001 |
| JP | 2003-235585 A | 8/2003 |
| JP | 2004-275013 A | 10/2004 |
| JP | 2004-275063 A | 10/2004 |

(Continued)

OTHER PUBLICATIONS

Arnold, F.H. 2001 Nature 409: 253-257. (Year: 2001).*
Weissman, K. 2004 Chemistry World "Rational or Random" (8 pages). (Retrieved from the internet Feb. 6, 2019). (Year: 2004).*
Supplementary European Search Report dated Dec. 9, 2016, in EP 14834684.4.
Database EPO Proteins [Online], Apr. 4, 2011, "Sequence 1 from Patent EP 2281900," retrieved from EBI accession No. EPOP:HI996699, Database accession No. HI996699, 2 pages.
International Search Report dated Sep. 9, 2014, in PCT/JP2014/071036.

(Continued)

*Primary Examiner* — Marsha Tsay
(74) *Attorney, Agent, or Firm* — Foley & Lardner LLP

(57) ABSTRACT

Provided is a composition by which glycated hemoglobin can be measured even in the presence of a stronger surfactant than a conventional case. Also provided is a buffer and/or stabilizer which maintains the residual activity of an amadoriase or lowers a reduction of residual activity. The present invention provides a composition for use in measuring glycated hemoglobin containing an amadoriase having substitution of one or more amino acid residues at a position(s) corresponding to an amino acid(s) selected from the group consisting of position 262, position 257, position 249, position 253, position 337, position 340, position 232, position 129, position 132, position 133, position 44, position 256, position 231 and position 81 of an amadoriase derived from the genus *Coniochaeta* and represented by SEQ ID No: 1 or 3, and having residual activity even in the presence of a surfactant. The present invention also provides a composition and kit for use in measuring glycated hemoglobin, comprising a specific stabilizer and/or a buffer. The present invention can provide an enzyme and a composition for use in measuring glycated hemoglobin, excellent in storage stability even if they are exposed to a surfactant.

10 Claims, 7 Drawing Sheets
Specification includes a Sequence Listing.

(56) References Cited

FOREIGN PATENT DOCUMENTS

| | | | |
|---|---|---|---|
| JP | 2006-325547 A | 12/2006 |
| JP | 2008-201968 A | 9/2008 |
| JP | 2009-000128 A | 1/2009 |
| JP | 2010-035469 A | 2/2010 |
| JP | 2010-057474 A | 3/2010 |
| JP | 2011-229526 A | 11/2011 |
| JP | 2013-500729 A | 1/2013 |
| WO | WO 97/13872 A1 | 4/1997 |
| WO | WO 02/06519 A1 | 1/2002 |
| WO | WO 2004/104203 A1 | 12/2004 |
| WO | WO 2005/049857 A1 | 6/2005 |
| WO | WO-2005/049858 A1 | 6/2005 |
| WO | WO 2005/087946 A1 | 9/2005 |
| WO | WO 2006/120976 A1 | 11/2006 |
| WO | WO 2010/041419 A1 | 4/2010 |
| WO | WO 2010/041715 A1 | 4/2010 |
| WO | WO 2011/015325 A1 | 2/2011 |
| WO | WO 2012/018094 A1 | 2/2012 |
| WO | WO 2012/020744 A1 | 2/2012 |
| WO | WO 2012/043601 A1 | 4/2012 |
| WO | WO 2012/173185 A1 | 12/2012 |
| WO | WO 2013/100006 A1 | 7/2013 |

OTHER PUBLICATIONS

Ferri et al., "Cloning and Expression of Fructosyl-amine Oxidase from Marine Yeast *Pichia* Species N1-1," Mar. Biotechnol., 2004, 6:625-632.

Ferri et al., "Isolation and characterization of a fructosyl-amine oxidase from an *Arthrobacter* sp.," Biotechnology Letters, 2005, 27:27-32.

Fujiwara et al., "Alteration of Substrate Specificity of Fructosyl-Amino Acid Oxidase from *Ulocladium* sp. JS-103," Journal of Bioscience and Bioengineering, 2006, 102(3):241-243.

Fujiwara et al., "Alteration of substrate specificity of fructosyl-amino acid oxidase from *Fusarium oxysporum*," Appl. Microbiol. Biotechnol., 2007, 74:813-819.

Hirokawa et al., "Molecular cloning and expression of novel fructosyl peptide oxidases and their application for the measurement of glycated protein," Biochemical and Biophysical Research Communications, 2003, 311:104-111.

Hirokawa et al., "Recombinant *Agrobacterium* AgaE-like Protein with Fructosyl Amino Acid Oxidase Activity," Biosci. Biotechnol. Biochem., 2002, 66(11):2323-2329.

Jeong et al., "The veA gene is necessary for the inducible expression by fructosyl amines of the *Aspergillus nidulans faoA* gene encoding fructosyl amino acid oxidase (amadoriase, EC 1.5.3.)," Arch. Microbiol., 2002, 178:344-350.

Kim et al., "Motif-Based Search for a Novel Fructosyl Peptide Oxidase from Genome Databases," Biotechnology and Bioengineering, Jun. 15, 2010, 106(3):358-366.

Sakai et al. Purification and Properties of Fructosyl Lysine Oxidase from *Fusarium oxysporum* S-1F4, Biosci. Biotech. Biochem., 1995, 59(3):487-491.

Sakaue et al., "Cloning and Expression of Fructosyl-amino Acid Oxidase Gene from *Corynebacterium* sp. 2-4-1 in *Escherichia coli*," Biosci. Biotechnol. Biochem., 2002, 66(6):1256-1261.

Yoshida et al., "Primary structures of fungal fructosyl amino acid oxidases and their application to the measurement of glycated proteins," Eur. J. Biochem., 1996, 242:499-505.

Office Action dated Mar. 5, 2019, in Japanese Application No. 2015-530983.

\* cited by examiner

Figure 1-1

```
                                                                                    Position 44                              Position 81
                                                                                        ●                                       ●
Co   1  MTSNRADTRVIVGGGGTIGSSTALHIVRSGYAPANITVLDTFEIPSAQSAGHDLNKIMGIRLRNKVDLQMSLEARQMWKEDELFQPFFHNTGRMDCEHT  100
Et   1  MAHSRASTKVVVGGGGTIGSSTALHLIRSGYTPSLQSAGHDLNKIMGIRLRNGPDLQLSLESLDMWQNDELFKPFFHQVGMIDCSSS  100
Py   1  MAASRAKTTVIVGGGGTIGSSTALHLLRSGYTPSNITVLDTYPIPSLGSAGNDLNKIMGIRLRNKVDLQLSLEAREMWREDELFRDFFHNTGRLDCAHG  100
Ar   1  MAASRKTTKVIVGGGGTIGSSTALHLLRSGYTATNITVLDTYPIPSAQSAGNDLNKIMGIRLRNPVDKQLSLEAQDMWCHDELFKPYFHNTGRMDCFGT  100
Cc   1  MAPSRANTSVIVGGGTIGSSTALHIVRSGYTPSNITVLDTYPIPSAQSAGNDLNKIMGIRLRNKVDLQLSLEARQMWREDDLFKEYFHNTGRLDCAHG  100
Nv   1  MTTPRKETTVLIIGGGGTIGSSTALHLLRAGYTPSNITVLDTYPIPSAQSAGNDLNKIMGIRLRNKVDLQLSLEARDMWRNDALFRPFFHNTGRLDCESS  100
Cn   1  MPPSRASTKVIVIGGGGTLGSSTALHLLRSGYTPSNITVLDTYLIPSAQSAGNDLNKIMGIRIRNPVDKQLSLEARDMWRNDEVFKPYFHNTGRLDCAHT  100
Pn   1  MAPSRANTSVIVGGGGTIGSSTALHIVRSGYTPSNVTVLDAYPIPSSQSAGNDLNKIMGVSLRNPVDLQALEARQMWNEDELFKKFFHNTGRLDCAHG  100
An   1  --MTPRANTKIIVVGGGGTLLIVGGGGTMGSSTALHLLRAGYTPSNITVLDTCPIPSAQSAGYDLNKIMSIRLRNKPDLQLSLEALDMWKNDPLFKPFFHNVGMIDVSST  99
Ul   1  MAPNRANISVIVGGGGTIGSSTALHIVRSGYTPSNITVLDTYPIPSAQSAGNDLNKIMGIRLRNKVDLQLSLEARQMWTEDDLFKEYFHKTGRLDCAHG  100
Pc   1  MAHSRESTKIVIVGGGGMGSSTALHLIRSGYTPSNITVLDVYPIPSLQSAGYDLNKIMSIRLRNGPDWQLSLEALDMWKNDPLFKPFFHNVGMLDCSSS  100
           *   :::.:*****.  ******.:****** :*   **  ***:****** **  **:.*:  *:****: :*:  :.:**.: .:.::**: . :.*

Position 129       Position 133
                                              Position 132
                                              ●●
Co  101 PEGIEDLKKQYQALHDAGAGLEKTHAWLDNEDEILSKMPLLQRDQIQGWKAIWSQDGGWLAAAKAINAIGQFLKERGVKFGFGDAGSFKQPLFDDEG--TT  199
Et  101 KEGIENLRRKYQTLLDAGIGLEKTNVWLESEDEILAKAPNFTREQVKGWKGLFCTDGGWLAAAKAINAIGIFLQDKGVKFGFGDAGTFQQPLFAADG--KT  199
Py  101 EKGINDLRQAYQTLLDANAGLEETNEWLDSEDEILARMPLLSREQIKGWKAVFSRDGGWLAAGKAINAIGEYLRKEGVKFGFGAGSFKPLFAPDG---I  197
Ar  101 EKGIAALKQQYTLLDADVGLEETTEWLDSEDAILAKMPLLERDQIKGWKAIFSQDGGWLAAAKAINAIGEELKRQGVNFGFGAGAFKKPLFAPDG--ST  199
Cc  101 EEGLADIRQAYQALLDANAGIEEEWLDREQIKGWKAVYSQDGGWLAAAKAINAIGEYLRAQGVKFGFGAGSFKQPLLAEG----V  197
Nv  101 AEGVEGLRREYQKLVEAGVGLEETHEWLDSEEAILEKAPILQREEILEKAPLLQEEILEKAPLLDRKQIKGWKAIYSEDGGWLAAAKAINSIGQVLKEKGVTFGFGSAGSFKKPLFDEDG--TT  199
Cn  101 PESIASLRKSYEAILKAGSGLEETHEWLDSEEAILDRKQIKGWKAIYSEDGGWLAAAKAINSIGQVLKEKGVTFGFGSAGSFKKPLFDEDG--TK  199
Pn  101 EKDIADLKSGYQALVDA----GLDATNEWLDSEDEILKRMPLLSRDQIKGWKAIFSKDGGWLAAAKAINAVGEYLRDQGVRFGFYGAGSFKAPLLAEG----V  195
An  100 EEGIEGLRKKYQSLLDAGIGLEKTNFMLESEDEILAKAPHFTQEQIKGWKAVFSEDGGWLAAAKAINAIGQFLKEQGVKFGFGDGGWLAAAKAINAIGRFLRDQGVKFGFGAGSFKQPLLAEG--V  199
Ul  101 EKGLADLKQAYQALLDANALEATTEWLDSEDKILEKMPLLNRDQIKGWKAVFSEDGGWLAAAKAINAIGRFLRDQGVKFGFGAGSFKQPLLAEG--V  197
Pc  101 QEGIASLRRKHQDLIDANIGLEKTNIWLESEDDILAKAPHFAREQIKGWKGLFCGDGGWLAAAKAINAIGTFLKSQGVKFGFGSAGTFKRPLFAPDG--AT  199
            . ::.* ::    .:  :.* .*.* : *::   .  ** :**:****.**   ** *: . ::.:  **:**.*. ::: ::  ..
```

Figure 1-2

```
                                                                              Position 257
                                                                                Position 256
                                                                  Position 232   Position 253             Position 262
                                          Position 231            Position 249
Co  200 CIGVETADGTKYYADKVVLAAGAWSPTLVDLEDQCCSKAWVYAHIQLTPEEAAEYKGVPVVYNGELGFFFEPDEFGVIKVCDEFPGFS--RFKEHQPYGAP  298
Et  200 CIGLETTDGTKYFADKVVLAAGAWSPTLVDLEDQCVSKAWVFAHIQLTPKEADAYKNPVVYDGEYGFFFEPDEYGVIKVCDEFPGFS---RFKLHQPYGAA  298
Py  198 CIGVETTDGTRYYADKVVLAAGAWSPALVDLEDQCVSKAWVYAHMQLTPKEAAAYKDTPVVYNGDLGFFFEPNEHGVIKVCDEFPGFT---RFKKHQPFGAR  296
Ar  200 CIGVETVDGTKYYGDKVVLAAGAWSPALVDLEEQCCSKAWVYAHIQLTPHEAAEYQGCPVVYHGDLGFFFEPNEHGVIKVCDEFPGFT---RFKQHQSYGAP  299
Cc  198 CIGVETVDGTRYYADKVVLAAGAWSPVLVDLEDQCVSKAWVYAHIQLTPEEAAEYKNVPVVYNGDVGFFFEPDEHGVIKVCDEFPGFT--RFKQHQPYGAK  296
Nv  200 CIGVETVDGTQYHADKVVLAAGAWSPALVDLEEQCCSKAWVYAHMQLTPEEAAVYKGCPVVYHGDVGFFFEPNENGVIKVCDEFPGFT--RFKQHQPYGAP  298
Cn  200 CIGVETVDGTQYFADKVVLAAGAWSPTLVDLEGQCCSKAWVYAHMQLTPEEAAEYKECPVVYNSELGFFFEPNEKGVIKVCDEFPGFT--RFKQHQPYGAS  298
Pn  196 AIGIETVDGTRYYADKVVLAAGAWSPTLVELHEQCVSKAWVYGHIQLTPEEAARYKNSPVVYNGDVGFFFEPNENGIIKVCDEFPGFT--HFKMHQPYGSP  294
An  200 CIGVETVDGTKYYADKVVLAAGAWSSTLVDLEEQCVSKAWVFAHIQLTPAEAAAYKNTPVIYDGDYGFFFEPNENGVIKVCDEFPGFT--RFKQHQPFGAS  298
Ul  198 CVGVETVDGTRYYADKVVLAAGAWSPALVDLQDQCVSKAWVYAHIQLSPSEEAAEYKNVPVVYDGEYGVIKVCDEFPGFT--RFKQHQPFGAS  296
Pc  200 CSGVETVDGTKYFADKVVLAAGAWSSTLVDLEDQCVSKAWVFAHIQLTPQESAQYKDVPVVYDGDYGFFFEPNEHGVIKVCDEFPGFS--RFKLHQPYGAT  298
          .  *:.* *****..*. ********..** ******  **..** ****.  .*:    *.  *:    * .:  ** ***. * ****:****:.**

Position 337 ● ● Position 340
Co  299 SPKRISVPRSHAKHPTDTYPDASEVSIKKAIATFLPRFQDKELFNRALCWCTDTADAALLMCEHPKWKNFILATGDSHSFKILPNVGKYVVELIEGRLP  398
Et  299 SPKMISVPRSHAKHPTDTYPDASEVTIRKAIARFLPEFKDKELFNRTMCWCTDTADANLLICEHPKWKNFILATGDSHSFKLLPNIGKYVVELLEGSLS  398
Py  297 APKRISVPRSHAKHPTDTYPHASEASIKKALAAFLPQFKDKELFNRAMCWCTDTADAALLICEHPWKNFMLATGDSGHSFKLLPNIGKHVVELIEGTLA  396
Ar  300 APTRVSVPRSHAKHPTDTYPDASEQSIRRAVAAFLPRFQSKELFNRAMCWCTDTADAALLICEHPWRNFILATGDSGHTFKLLPNIGKHVVELLEGTLA  399
Cc  297 APKRISVPRSAAKHPTDTYPDASEKSIRKAIATFLPKFTEKELFNRHLCWCTDTADAALLMCEHPEWKNFVLATGDSGHTFKLLPNIGKHVVELLEGTLA  396
Nv  299 APKPVSVPRSHAKHPTDTYPDASEESIKRAVSTFLPRFKDKPLFNRALCWCTDTADSALLICEHPRWKNFILATGDSGHSFKLLPIIGKHVVELVEGRLA  398
Cn  299 STKHISFPRSHAKHPTDTIPDESDASIRRAISAFLPRFKEKELFNRALCWCTDTADAALLICEHPEWKNFILATGDSGHSFKILPNIGKHVVELIEGTLA  398
Pn  295 APKRISVPRSHAKHPTDTIPDASDVSIRRAIATFMPQFKNKKMFNQAMCWCTDTADAALLVCEHPWKNFNDKELFNRAMCWCTDTADANLLICEHPWKNFVLATGDSGHSFKLLPNIGKHVVELLEGTLA 394
An  299 APKPISVPRSHAKHPTDTYPHASEVTIKKAINRFLPRFNDKELFNRAMCWCTDTADANLLVCEHPRWKGFYLATGDSGHTFKLLPNIGKHVVELLEERLE  398
Ul  297 APKRISVPRSAAKHPTDTYPDASEVSIRKAIATFLPKFTEKEVFNRHLCWCTDTADAALLICEHPKWKNFVLATGDSGHTFKLLPNIGKHVVELLEGTLA  396
Pc  299 SPKLISVPRSHAKHPTDTYPDSSEETIRKALARFMPRFKDKELFNRSMCWCTDTADANLLICEHPKWKNFILATGDSGHSFKVLPNIGKHVELIEGRLP  398
           :*  * ***:.*****  **  :  *:.:: :* * .*: *** :******:*:* ******* ** :.* ***.*::**:**:***::*****:***  *
```

Figure 1-3

```
Co  399 EEMAYQWRWRPG-GDALKSRRAAPPKDLADMPGWKHDPKL------------------------------- 437 (SEQ ID NO 1)
Et  399 QEMAGAWRWRPG-GDALRSRRGAPAKDLAEMPGWKHDAHL------------------------------- 437 (SEQ ID NO 34)
Py  397 ADLAHAWRWRPGIGDALQSRRAAPAKDLADMPGWNHDESPRAKL--------------------------- 440 (SEQ ID NO 35)
Ar  400 DDLAQAWRWRPGQGDALKSRRAAPAKDLADMPGWNHDGDSGNATSGTSSEHKL------------------ 452 (SEQ ID NO 36)
Cc  397 EDLAHAWRWRPGTGDALKSRRAAPAKDLADMPGWKHDDVVKSKL--------------------------- 440 (SEQ ID NO 37)
Nv  399 DDLAEAWRWRPGQGDARKSIRAAPAKDLADMPGWKHDQDSESR---------------------------- 441 (SEQ ID NO 38)
Cn  399 EDLAESWRWRPGSGDPLISRRAAPARDLADLPGWNHDEPSDDMDVKDVAVSLASVKIGENIGEKVVEDGARVGVKVLA 477 (SEQ ID NO 39)
Pn  395 DDLAHAWRWRPGSGDALKSRRSAPAKDLADMPGWNHDKPRANL---------------------------- 437 (SEQ ID NO 40)
An  399 SVFKDAWRWRPGSGDALKSRRAAPAKDLADMPGWRNEAKM------------------------------- 438 (SEQ ID NO 41)
Ul  397 DDLAHAWRWRPGTGDALKSRRAARAKDLADMPGWNHDGEAPRAKL-------------------------- 441 (SEQ ID NO 42)
Pc  399 QDLAGAWRWRPG-GDALKSKRSAPAKDLAEMPGWKHDAKL------------------------------- 437 (SEQ ID NO 43)
            ******:**.   *  *   *   * *     .:****:;:****.::
```

Co: Amadoriase from Coniochaeta sp.
Et: Amadoriase from Eupenicillium terrenum
Py: Ketoamine Oxidase from Pyrenochaeta sp.
Ar: Ketoamine Oxidase from Arthrinium sp.
Cc: Ketoamine Oxidase from Curvularia clavata
Nv: Ketoamine Oxidase from Neocosmospora vasinfecta
Cn: Fructosyl Amino Acid Oxidase from Cryptococcus neoformans
Pn: Fructosyl Peptide Oxidase from Phaeosphaeria nodorum
An: Fructosyl Amino Acid Oxidase from Aspergillus nidulans
Ul: Fructosyl Amino Acid Oxidase from Ulocladium sp.
Pc: Fructosyl Amino Acid Oxidase from Penicillium crysogenum

SEQUENCE LISTING

<160> NUMBER OF SEQ ID NOS: 74

<210> SEQ ID NO 1
<211> LENGTH: 437
<212> TYPE: PRT
<213> ORGANISM: Coniochaeta sp.

<400> SEQUENCE: 1

| | | | | | | | | | | | | | | |
|---|---|---|---|---|---|---|---|---|---|---|---|---|---|---|
| Met | Thr | Ser | Asn | Arg | Ala | Asp | Thr | Arg | Val | Ile | Val | Gly | Gly | Gly |
| 1 | | | | 5 | | | | | 10 | | | | | 15 |
| Gly | Thr | Ile | Gly | Ser | Ser | Thr | Ala | Leu | His | Leu | Val | Arg | Ser | Gly |  Tyr |
| | | | 20 | | | | | 25 | | | | | 30 | |
| Ala | Pro | Ala | Asn | Ile | Thr | Val | Leu | Asp | Thr | Phe | Glu | Ile | Pro | Ser | Ala |
| | | 35 | | | | | 40 | | | | | 45 | | |
| Gln | Ser | Ala | Gly | His | Asp | Leu | Asn | Lys | Ile | Met | Gly | Ile | Arg | Leu | Arg |
| | 50 | | | | | 55 | | | | | 60 | | | | |
| Asn | Lys | Val | Asp | Leu | Gln | Met | Ser | Leu | Glu | Ala | Arg | Gln | Met | Trp | Lys |
| 65 | | | | | 70 | | | | | 75 | | | | | 80 |
| Glu | Asp | Glu | Leu | Phe | Gln | Pro | Phe | His | Asn | Thr | Gly | Arg | Met | Asp |
| | | | | 85 | | | | | 90 | | | | | 95 |
| Cys | Glu | His | Thr | Pro | Glu | Gly | Ile | Glu | Asp | Leu | Lys | Lys | Gln | Tyr | Gln |
| | | | 100 | | | | | 105 | | | | | 110 | | |
| Ala | Leu | His | Asp | Ala | Gly | Ala | Gly | Leu | Glu | Lys | Thr | His | Ala | Trp | Leu |
| | | | 115 | | | | | 120 | | | | | 125 | | |
| Asp | Asn | Glu | Asp | Glu | Ile | Leu | Ser | Lys | Met | Pro | Leu | Leu | Gln | Arg | Asp |
| | | 130 | | | | | 135 | | | | | 140 | | | |
| Gln | Ile | Gln | Gly | Trp | Lys | Ala | Ile | Trp | Ser | Gln | Asp | Gly | Gly | Trp | Leu |
| 145 | | | | | 150 | | | | | 155 | | | | | 160 |
| Ala | Ala | Ala | Lys | Ala | Ile | Asn | Ala | Ile | Gly | Gln | Phe | Leu | Lys | Glu | Arg |
| | | | | 165 | | | | | 170 | | | | | 175 | |
| Gly | Val | Lys | Phe | Gly | Phe | Gly | Ala | Gly | Ser | Phe | Lys | Gln | Pro | Leu |
| | | | 180 | | | | | 185 | | | | | 190 | | |
| Phe | Asp | Asp | Glu | Gly | Thr | Thr | Cys | Ile | Gly | Val | Glu | Thr | Ala | Asp | Gly |
| | | 195 | | | | | 200 | | | | | 205 | | | |
| Thr | Lys | Tyr | Tyr | Ala | Asp | Lys | Val | Val | Leu | Ala | Ala | Gly | Ala | Trp | Ser |
| | 210 | | | | | 215 | | | | | 220 | | | | |
| Pro | Thr | Leu | Val | Asp | Leu | Glu | Asp | Gln | Cys | Cys | Ser | Lys | Ala | Trp | Val |
| 225 | | | | | 230 | | | | | 235 | | | | | 240 |
| Tyr | Ala | His | Ile | Gln | Leu | Thr | Pro | Glu | Glu | Ala | Ala | Glu | Tyr | Lys | Gly |
| | | | | 245 | | | | | 250 | | | | | 255 | |
| Val | Pro | Val | Val | Tyr | Asn | Gly | Glu | Phe | Gly | Phe | Phe | Phe | Glu | Pro | Asp |
| | | | 260 | | | | | 265 | | | | | 270 | | |
| Glu | Phe | Gly | Val | Ile | Lys | Val | Cys | Asp | Glu | Phe | Pro | Gly | Phe | Ser | Arg |
| | | 275 | | | | | 280 | | | | | 285 | | | |
| Phe | Lys | Glu | His | Gln | Pro | Tyr | Gly | Ala | Pro | Ser | Pro | Lys | Arg | Ile | Ser |
| | | 290 | | | | | 295 | | | | | 300 | | | |
| Val | Pro | Arg | Ser | His | Ala | Lys | His | Pro | Thr | Asp | Thr | Tyr | Pro | Asp | Ala |
| 305 | | | | | 310 | | | | | 315 | | | | | 320 |
| Ser | Glu | Val | Ser | Ile | Lys | Lys | Ala | Ile | Ala | Thr | Phe | Leu | Pro | Arg | Phe |
| | | | | 325 | | | | | 330 | | | | | 335 | |
| Gln | Asp | Lys | Glu | Leu | Phe | Asn | Arg | Ala | Leu | Cys | Trp | Cys | Thr | Asp | Thr |
| | | | 340 | | | | | 345 | | | | | 350 | | |
| Ala | Asp | Ala | Ala | Leu | Leu | Met | Cys | Glu | His | Pro | Lys | Trp | Lys | Asn | Phe |
| | | | 355 | | | | | 360 | | | | | 365 | | |

```
Ile Leu Ala Thr Gly Asp Ser Gly His Ser Phe Lys Ile Leu Pro Asn
370                 375                 380
Val Gly Lys Tyr Val Val Glu Leu Ile Glu Gly Arg Leu Pro Glu Glu
385                 390                 395                 400
Met Ala Tyr Gln Trp Arg Trp Arg Pro Gly Gly Asp Ala Leu Lys Ser
                405                 410                 415
Arg Arg Ala Ala Pro Pro Lys Asp Leu Ala Asp Met Pro Gly Trp Lys
            420                 425                 430
His Asp Pro Lys Leu
            435

<210> SEQ ID NO 2
<211> LENGTH: 1314
<212> TYPE: DNA
<213> ORGANISM: Coniochaeta sp.
<220> FEATURE:
<221> NAME/KEY: CDS
<222> LOCATION: (1)..(1314)

<400> SEQUENCE: 2 atg acg tcg aat cgt gca gat aca agg gtg att gtc gtc ggt ggc gga       48
Met Thr Ser Asn Arg Ala Asp Thr Arg Val Ile Val Val Gly Gly Gly
1               5                   10                  15 gga acg att ggt tcc tcg aca gcg ctg cat ctt gtg agg agt ggt tat       96
Gly Thr Ile Gly Ser Ser Thr Ala Leu His Leu Val Arg Ser Gly Tyr
            20                  25                  30 gct ccc gca aat atc acg gtc ttg gac aca ttt gag att cca tcg gct      144
Ala Pro Ala Asn Ile Thr Val Leu Asp Thr Phe Glu Ile Pro Ser Ala
        35                  40                  45 caa tca gcc ggc cat gat ctc aac aag atc atg gga ata cga ctg cgc      192
Gln Ser Ala Gly His Asp Leu Asn Lys Ile Met Gly Ile Arg Leu Arg
    50                  55                  60 aac aag gtg gac ctg caa atg agt cta gag gct aga cag atg tgg aag      240
Asn Lys Val Asp Leu Gln Met Ser Leu Glu Ala Arg Gln Met Trp Lys
65                  70                  75                  80 gag gat gag tta ttc cag ccc ttc ttt cac aat acc ggc aga atg gac      288
Glu Asp Glu Leu Phe Gln Pro Phe Phe His Asn Thr Gly Arg Met Asp
                85                  90                  95 tgc gaa cac acg cct gag ggt atc gag gac ctg aaa aag cag tac cag      336
Cys Glu His Thr Pro Glu Gly Ile Glu Asp Leu Lys Lys Gln Tyr Gln
            100                 105                 110 gca ctg cac gat gcc ggt gcg ggt ctg gag aag act cat gcc tgg ttg      384
Ala Leu His Asp Ala Gly Ala Gly Leu Glu Lys Thr His Ala Trp Leu
        115                 120                 125 gac aac gag gat gag atc tta tcc aag atg ccg ttg ctt caa cgt gac      432
Asp Asn Glu Asp Glu Ile Leu Ser Lys Met Pro Leu Leu Gln Arg Asp
    130                 135                 140 caa ata caa gga tgg aaa gca ata tgg agt caa gat ggc ggc tgg tta      480
Gln Ile Gln Gly Trp Lys Ala Ile Trp Ser Gln Asp Gly Gly Trp Leu
145                 150                 155                 160 gct gcg gca aag gcc atc aat gcg atc gga cag ttc ttg aaa gaa cgt      528
Ala Ala Ala Lys Ala Ile Asn Ala Ile Gly Gln Phe Leu Lys Glu Arg
                165                 170                 175 ggt gta aag ttc gga ttc ggc ggc gct gga tcc ttc aag caa ccc ctt      576
Gly Val Lys Phe Gly Phe Gly Gly Ala Gly Ser Phe Lys Gln Pro Leu
            180                 185                 190 ttc gac gat gaa ggc aca act tgc att ggc gtt gag acg gca gat ggt      624
Phe Asp Asp Glu Gly Thr Thr Cys Ile Gly Val Glu Thr Ala Asp Gly
        195                 200                 205 acc aaa tat tac gct gac aag gtg gtc tta gca gct ggc gca tgg agc      672
Thr Lys Tyr Tyr Ala Asp Lys Val Val Leu Ala Ala Gly Ala Trp Ser
```

```
                Thr Lys Tyr Tyr Ala Asp Lys Val Val Leu Ala Ala Gly Ala Trp Ser
                            210                 215                 220 cca acc ctg gtg gac ctg gaa gat caa tgt tgc tcg aag gct tgg gtg        720
Pro Thr Leu Val Asp Leu Glu Asp Gln Cys Cys Ser Lys Ala Trp Val
225                 230                 235                 240 tat gct cat att cag ttg acg cct gaa gag gcc gct gag tat aag ggt        768
Tyr Ala His Ile Gln Leu Thr Pro Glu Glu Ala Ala Glu Tyr Lys Gly
                245                 250                 255 gtc cca gtt gtg tat aat ggc gaa ttt ggc ttc ttc ttt gag cct gat        816
Val Pro Val Val Tyr Asn Gly Glu Phe Gly Phe Phe Phe Glu Pro Asp
            260                 265                 270 gag ttt ggt gta ata aag gtg tgc gac gag ttc cca gga ttc tcg cgc        864
Glu Phe Gly Val Ile Lys Val Cys Asp Glu Phe Pro Gly Phe Ser Arg
        275                 280                 285 ttc aag gaa cat caa ccc tat ggc gcc cca tct ccg aaa cgg ata tca        912
Phe Lys Glu His Gln Pro Tyr Gly Ala Pro Ser Pro Lys Arg Ile Ser
    290                 295                 300 gta cca cga tcg cac gcc aag cat ccc aca gac act tat cca gac gca        960
Val Pro Arg Ser His Ala Lys His Pro Thr Asp Thr Tyr Pro Asp Ala
305                 310                 315                 320 tcc gaa gtc agc atc aaa aaa gca atc gcg acg ttt ctc cct cga ttt       1008
Ser Glu Val Ser Ile Lys Lys Ala Ile Ala Thr Phe Leu Pro Arg Phe
                325                 330                 335 cag gac aag gag ctc ttc aat cgc gcc ttg tgc tgg tgt aca gac act       1056
Gln Asp Lys Glu Leu Phe Asn Arg Ala Leu Cys Trp Cys Thr Asp Thr
                340                 345                 350 gcg gac gct gct ctc ttg atg tgt gaa cac ccc aaa tgg aag aat ttc       1104
Ala Asp Ala Ala Leu Leu Met Cys Glu His Pro Lys Trp Lys Asn Phe
            355                 360                 365 att cta gcg acc ggc gac agc gga cac tca ttc aaa atc ttg cct aac       1152
Ile Leu Ala Thr Gly Asp Ser Gly His Ser Phe Lys Ile Leu Pro Asn
        370                 375                 380 gtc gga aaa tac gta gtc gag ttg ata gag ggc cgc ctg ccg gag gaa       1200
Val Gly Lys Tyr Val Val Glu Leu Ile Glu Gly Arg Leu Pro Glu Glu
385                 390                 395                 400 atg gct tat caa tgg agg tgg cgg cca gga ggc gat gca ctc aag tct       1248
Met Ala Tyr Gln Trp Arg Trp Arg Pro Gly Gly Asp Ala Leu Lys Ser
                405                 410                 415 aga cgt gcg gca ccg cca aaa gat ctt gca gac atg cca gga tgg aaa       1296
Arg Arg Ala Ala Pro Pro Lys Asp Leu Ala Asp Met Pro Gly Trp Lys
                420                 425                 430 cat gat ccg aaa ttg taa                                                1314
His Asp Pro Lys Leu
            435

<210> SEQ ID NO 3
<211> LENGTH: 434
<212> TYPE: PRT
<213> ORGANISM: Coniochaeta sp.

<400> SEQUENCE: 3

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Tyr Glu Ile Pro Ser Ala
            35                  40                  45

Gln Ser Ala Gly His Asp Leu Asn Lys Ile Met Gly Ile Arg Leu Arg
        50                  55                  60
```

```
                Asn Lys Val Asp Leu Gln Met Ser Leu Glu Ala Arg Gln Met Trp Lys
                 65                  70                  75                  80
                Glu Asp Glu Leu Phe Gln Pro Phe Phe His Asn Thr Gly Arg Met Asp
                                 85                  90                  95
                Cys Ala His Thr Pro Glu Gly Ile Glu Asp Leu Lys Lys Gln Tyr Gln
                            100                 105                 110
                Ala Leu His Asp Ala Gly Ala Gly Leu Glu Lys Thr His Ala Trp Leu
                        115                 120                 125
                Asp Asn Glu Asp Glu Ile Leu Ser Lys Met Pro Leu Leu Gln Arg Asp
                    130                 135                 140
                Gln Ile Gln Gly Trp Lys Ala Ile Trp Ser Gln Asp Gly Gly Trp Leu
                145                 150                 155                 160
                Ala Ala Ala Lys Ala Ile Asn Ala Ile Gly Gln Phe Leu Lys Glu Arg
                                165                 170                 175
                Gly Val Lys Phe Gly Phe Gly Asp Ala Gly Ser Phe Lys Gln Pro Leu
                            180                 185                 190
                Phe Asp Asp Glu Gly Thr Thr Cys Ile Gly Val Glu Thr Ala Asp Gly
                        195                 200                 205
                Thr Lys Tyr Tyr Ala Asp Lys Val Val Leu Ala Ala Gly Ala Trp Ser
                    210                 215                 220
                Pro Thr Leu Val Asp Leu Glu Asp Gln Cys Cys Ser Lys Ala Trp Val
                225                 230                 235                 240
                Tyr Ala His Ile Gln Leu Thr Pro Glu Glu Ala Glu Tyr Lys Gly
                                245                 250                 255
                Val Pro Val Val Tyr Asn Gly Glu Phe Gly Phe Phe Glu Pro Asp
                            260                 265                 270
                Glu Phe Gly Val Ile Lys Val Cys Asp Glu Phe Pro Gly Phe Ser Arg
                        275                 280                 285
                Phe Lys Glu His Gln Pro Tyr Gly Ala Pro Ser Pro Lys Arg Ile Ser
                    290                 295                 300
                Val Pro Arg Ser His Ala Lys His Pro Thr Asp Thr Tyr Pro Asp Ala
                305                 310                 315                 320
                Ser Glu Val Ser Ile Lys Lys Ala Ile Ala Thr Phe Leu Pro Arg Phe
                                325                 330                 335
                Gln Asp Lys Glu Leu Phe Asn Arg Ala Leu Cys Trp Cys Thr Asp Thr
                            340                 345                 350
                Ala Asp Ala Ala Leu Leu Met Cys Glu His Pro Lys Trp Lys Asn Phe
                        355                 360                 365
                Ile Leu Ala Thr Gly Asp Ser Gly His Ser Phe Lys Ile Leu Pro Asn
                    370                 375                 380
                Val Gly Lys Tyr Val Val Glu Leu Ile Glu Gly Arg Leu Pro Glu Glu
                385                 390                 395                 400
                Met Ala Tyr Gln Trp Arg Trp Arg Pro Gly Gly Asp Ala Leu Lys Ser
                                405                 410                 415
                Arg Arg Ala Ala Pro Pro Lys Asp Leu Ala Asp Met Pro Gly Trp Lys
                            420                 425                 430
                His Asp

<210> SEQ ID NO 4
<211> LENGTH: 1305
<212> TYPE: DNA
<213> ORGANISM: Coniochaeta sp.
<220> FEATURE:
<221> NAME/KEY: CDS
<222> LOCATION: (1)..(1305)
```

-continued

```
<400> SEQUENCE: 4 atg acg tcg aat cgt gca gat aca agg gtg att gtc gtc ggt ggc gga      48
Met Thr Ser Asn Arg Ala Asp Thr Arg Val Ile Val Val Gly Gly Gly
1               5                   10                  15 gga acg att ggt tcc tcg aca gcg ctg cat ctt gtg agg agt ggt tat      96
Gly Thr Ile Gly Ser Ser Thr Ala Leu His Leu Val Arg Ser Gly Tyr
            20                  25                  30 gct ccc gca aat atc acg gtc ttg gac aca tat gag att cca tcg gct     144
Ala Pro Ala Asn Ile Thr Val Leu Asp Thr Tyr Glu Ile Pro Ser Ala
        35                  40                  45 caa tca gcc ggc cat gat ctc aac aag atc atg gga ata cga ctg cgc     192
Gln Ser Ala Gly His Asp Leu Asn Lys Ile Met Gly Ile Arg Leu Arg
    50                  55                  60 aac aag gtg gac ctg caa atg agt cta gag gct aga cag atg tgg aag     240
Asn Lys Val Asp Leu Gln Met Ser Leu Glu Ala Arg Gln Met Trp Lys
65                  70                  75                  80 gag gat gag tta ttc cag ccc ttc ttt cac aat acc ggc aga atg gac     288
Glu Asp Glu Leu Phe Gln Pro Phe Phe His Asn Thr Gly Arg Met Asp
                85                  90                  95 tgc gca cac acg cct gag ggt atc gag gac ctg aaa aag cag tac cag     336
Cys Ala His Thr Pro Glu Gly Ile Glu Asp Leu Lys Lys Gln Tyr Gln
            100                 105                 110 gca ctg cac gat gcc ggt gcg ggt ctg gag aag act cat gcc tgg ttg     384
Ala Leu His Asp Ala Gly Ala Gly Leu Glu Lys Thr His Ala Trp Leu
        115                 120                 125 gac aac gag gat gag atc tta tcc aag atg ccg ttg ctt caa cgt gac     432
Asp Asn Glu Asp Glu Ile Leu Ser Lys Met Pro Leu Leu Gln Arg Asp
    130                 135                 140 caa ata caa gga tgg aaa gca ata tgg agt caa gat ggc ggc tgg tta     480
Gln Ile Gln Gly Trp Lys Ala Ile Trp Ser Gln Asp Gly Gly Trp Leu
145                 150                 155                 160 gct gcg gca aag gcc atc aat gcg atc gga cag ttc ttg aaa gaa cgt     528
Ala Ala Ala Lys Ala Ile Asn Ala Ile Gly Gln Phe Leu Lys Glu Arg
                165                 170                 175 ggt gta aag ttc gga ttc ggc gac gct gga tcc ttc aag caa ccc ctt     576
Gly Val Lys Phe Gly Phe Gly Asp Ala Gly Ser Phe Lys Gln Pro Leu
            180                 185                 190 ttc gac gat gaa ggc aca act tgc att ggc gtt gag acg gca gat ggt     624
Phe Asp Asp Glu Gly Thr Thr Cys Ile Gly Val Glu Thr Ala Asp Gly
        195                 200                 205 acc aaa tat tac gct gac aag gtg gtc tta gca gct ggc gca tgg agc     672
Thr Lys Tyr Tyr Ala Asp Lys Val Val Leu Ala Ala Gly Ala Trp Ser
    210                 215                 220 cca acc ctg gtg gac ctg gaa gat caa tgt tgc tcg aag gct tgg gtg     720
Pro Thr Leu Val Asp Leu Glu Asp Gln Cys Cys Ser Lys Ala Trp Val
225                 230                 235                 240 tat gct cat att cag ttg acg cct gaa gag gcc gct gag tat aag ggt     768
Tyr Ala His Ile Gln Leu Thr Pro Glu Glu Ala Ala Glu Tyr Lys Gly
                245                 250                 255 gtc cca gtt gtg tat aat ggc gaa ttt ggc ttc ttc ttt gag cct gat     816
Val Pro Val Val Tyr Asn Gly Glu Phe Gly Phe Phe Phe Glu Pro Asp
            260                 265                 270 gag ttt ggt gta ata aag gtg tgc gac gag ttc cca gga ttc tcg cgc     864
Glu Phe Gly Val Ile Lys Val Cys Asp Glu Phe Pro Gly Phe Ser Arg
        275                 280                 285 ttc aag gaa cat caa ccc tat ggc gcc cca tct ccg aaa cgg ata tca     912
Phe Lys Glu His Gln Pro Tyr Gly Ala Pro Ser Pro Lys Arg Ile Ser
    290                 295                 300
```

```
gta cca cga tcg cac gcc aag cat ccc aca gac act tat cca gac gca    960
Val Pro Arg Ser His Ala Lys His Pro Thr Asp Thr Tyr Pro Asp Ala
305                 310                 315                 320 tcc gaa gtc agc atc aaa aaa gca atc gcg acg ttt ctc cct cga ttt   1008
Ser Glu Val Ser Ile Lys Lys Ala Ile Ala Thr Phe Leu Pro Arg Phe
                325                 330                 335 cag gac aag gag ctc ttc aat cgc gcc ttg tgc tgg tgt aca gac act   1056
Gln Asp Lys Glu Leu Phe Asn Arg Ala Leu Cys Trp Cys Thr Asp Thr
            340                 345                 350 gcg gac gct gct ctc ttg atg tgt gaa cac ccc aaa tgg aag aat ttc   1104
Ala Asp Ala Ala Leu Leu Met Cys Glu His Pro Lys Trp Lys Asn Phe
        355                 360                 365 att cta gcg acc ggc gac agc gga cac tca ttc aaa atc ttg cct aac   1152
Ile Leu Ala Thr Gly Asp Ser Gly His Ser Phe Lys Ile Leu Pro Asn
    370                 375                 380 gtc gga aaa tac gta gtc gag ttg ata gag ggc cgc ctg ccg gag gaa   1200
Val Gly Lys Tyr Val Val Glu Leu Ile Glu Gly Arg Leu Pro Glu Glu
385                 390                 395                 400 atg gct tat caa tgg agg tgg cgg cca gga ggc gat gca ctc aag tct   1248
Met Ala Tyr Gln Trp Arg Trp Arg Pro Gly Gly Asp Ala Leu Lys Ser
                405                 410                 415 aga cgt gcg gca ccg cca aaa gat ctt gca gac atg cca gga tgg aaa   1296
Arg Arg Ala Ala Pro Pro Lys Asp Leu Ala Asp Met Pro Gly Trp Lys
                420                 425                 430 cat gat taa                                                        1305
His Asp

<210> SEQ ID NO 5
<211> LENGTH: 29
<212> TYPE: DNA
<213> ORGANISM: Artificial
<220> FEATURE:
<223> OTHER INFORMATION: primer

<400> SEQUENCE: 5
ccagttgtgt atcatggcga atttggctt                                      29

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
tcaggctcaa agaagaagcc aaattcgcc                                      29

<210> SEQ ID NO 7
<211> LENGTH: 27
<212> TYPE: DNA
<213> ORGANISM: Artificial
<220> FEATURE:
<223> OTHER INFORMATION: primer

<400> SEQUENCE: 7
gagtataagg gttgcccagt tgtgtat                                        27

<210> SEQ ID NO 8
<211> LENGTH: 29
<212> TYPE: DNA
<213> ORGANISM: Artificial
<220> FEATURE:
<223> OTHER INFORMATION: primer
```

```
<400> SEQUENCE: 8
aagccaaatt cgccattata cacaactgg                                29

<210> SEQ ID NO 9
<211> LENGTH: 27
<212> TYPE: DNA
<213> ORGANISM: Artificial
<220> FEATURE:
<223> OTHER INFORMATION: primer

<400> SEQUENCE: 9
gagtataagg gtagcccagt tgtgtat                                  27

<210> SEQ ID NO 10
<211> LENGTH: 27
<212> TYPE: DNA
<213> ORGANISM: Artificial
<220> FEATURE:
<223> OTHER INFORMATION: primer

<400> SEQUENCE: 10
gagtataagg gtaccccagt tgtgtat                                  27

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
gaagaggccg ctaaatataa gggtgtccca                               30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
gccattatac acaactggga cacccttata                               30

<210> SEQ ID NO 13
<211> LENGTH: 30
<212> TYPE: DNA
<213> ORGANISM: Artificial
<220> FEATURE:
<223> OTHER INFORMATION: primer

<400> SEQUENCE: 13
gaagaggccg ctcgttataa gggtgtccca                               30

<210> SEQ ID NO 14
<211> LENGTH: 27
<212> TYPE: DNA
<213> ORGANISM: Artificial
<220> FEATURE:
<223> OTHER INFORMATION: primer

<400> SEQUENCE: 14
ctccctcgat ttaaagacaa ggagctc                                  27

<210> SEQ ID NO 15
<211> LENGTH: 29
```

```
<212> TYPE: DNA
<213> ORGANISM: Artificial
<220> FEATURE:
<223> OTHER INFORMATION: primer

<400> SEQUENCE: 15
cacaaggcgc gattgaagag ctccttgtc                                              29

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
tttcaggaca agccgctctt caatcgcgcc                                             30

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
tgtacaccag cacaaggcgc gattgaagag                                             30

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
gacaacgagg atgcgatctt atccaagatg                                             30

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
acgttgaagc aacggcatct tggataagat                                             30

<210> SEQ ID NO 20
<211> LENGTH: 30
<212> TYPE: DNA
<213> ORGANISM: Artificial
<220> FEATURE:
<223> OTHER INFORMATION: primer

<400> SEQUENCE: 20
gacaacgagg atatgatctt atccaagatg                                             30

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21
```
gacaacgagg ataaaatctt atccaagatg                                           30

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
gtcttggaca catttccgat tccatcggct                                           30

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
atcatggccg gctgattgag ccgatggaat                                           30

<210> SEQ ID NO 24
<211> LENGTH: 27
<212> TYPE: DNA
<213> ORGANISM: Artificial
<220> FEATURE:
<223> OTHER INFORMATION: primer

<400> SEQUENCE: 24
gagtataaga aagtcccagt tgtgtat                                              27

<210> SEQ ID NO 25
<211> LENGTH: 27
<212> TYPE: DNA
<213> ORGANISM: Artificial
<220> FEATURE:
<223> OTHER INFORMATION: primer

<400> SEQUENCE: 25
gagtataagc gcgtcccagt tgtgtat                                              27

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
cagatgtgga agaaagatga gttattccag                                           30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
attgtgaaag aagggctgga ataactcatc                                           30

<210> SEQ ID NO 28
<211> LENGTH: 30
<212> TYPE: DNA
<213> ORGANISM: Artificial

<220> FEATURE:
<223> OTHER INFORMATION: primer

<400> SEQUENCE: 28
gtcttggaca catatccgat tccatcggct                              30

<210> SEQ ID NO 29
<211> LENGTH: 29
<212> TYPE: DNA
<213> ORGANISM: Artificial
<220> FEATURE:
<223> OTHER INFORMATION: primer

<400> SEQUENCE: 29
aagccaaatt cgccatgata cacaactgg                               29

<210> SEQ ID NO 30
<211> LENGTH: 30
<212> TYPE: DNA
<213> ORGANISM: Artificial
<220> FEATURE:
<223> OTHER INFORMATION: primer

<400> SEQUENCE: 30
gaagaggccg ctaaatataa gggttgccca                              30

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
gccatgatac acaactgggc aacccttata                              30

<210> SEQ ID NO 32
<211> LENGTH: 27
<212> TYPE: DNA
<213> ORGANISM: Artificial
<220> FEATURE:
<223> OTHER INFORMATION: primer

<400> SEQUENCE: 32
ctccctcgat ttaaagacaa gccgctc                                 27

<210> SEQ ID NO 33
<211> LENGTH: 29
<212> TYPE: DNA
<213> ORGANISM: Artificial
<220> FEATURE:
<223> OTHER INFORMATION: primer

<400> SEQUENCE: 33
cacaaggcgc gattgaagag cggcttgtc                               29

<210> SEQ ID NO 34
<211> LENGTH: 437
<212> TYPE: PRT
<213> ORGANISM: Eupenicillium terrenum

<400> SEQUENCE: 34

Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr

```
            20                  25                  30
Thr Pro Ser Asn Ile Thr Val Leu Asp Val Tyr Lys Thr Pro Ser Leu
            35                  40                  45
Gln Ser Ala Gly His Asp Leu Asn Lys Ile Met Gly Ile Arg Leu Arg
            50                  55                  60
Asn Gly Pro Asp Leu Gln Leu Ser Leu Glu Ser Leu Asp Met Trp Gln
 65                  70                  75                  80
Asn Asp Glu Leu Phe Lys Pro Phe His Gln Val Gly Met Ile Asp
                85                  90                  95
Cys Ser Ser Lys Glu Gly Ile Glu Asn Leu Arg Arg Lys Tyr Gln
                100                 105                 110
Thr Leu Leu Asp Ala Gly Ile Gly Leu Glu Lys Thr Asn Val Trp Leu
            115                 120                 125
Glu Ser Glu Asp Glu Ile Leu Ala Lys Ala Pro Asn Phe Thr Arg Glu
            130                 135                 140
Gln Val Lys Gly Trp Lys Gly Leu Phe Cys Thr Asp Gly Gly Trp Leu
145                 150                 155                 160
Ala Ala Ala Lys Ala Ile Asn Ala Ile Gly Ile Phe Leu Gln Asp Lys
            165                 170                 175
Gly Val Lys Phe Gly Phe Gly Asp Ala Gly Thr Phe Gln Gln Pro Leu
            180                 185                 190
Phe Ala Ala Asp Gly Lys Thr Cys Ile Gly Leu Glu Thr Thr Asp Gly
            195                 200                 205
Thr Lys Tyr Phe Ala Asp Lys Val Val Leu Ala Ala Gly Ala Trp Ser
            210                 215                 220
Pro Thr Leu Val Asp Leu Glu Asp Gln Cys Val Ser Lys Ala Trp Val
225                 230                 235                 240
Phe Ala His Ile Gln Leu Thr Pro Lys Glu Ala Asp Ala Tyr Lys Asn
            245                 250                 255
Val Pro Val Val Tyr Asp Gly Glu Tyr Gly Phe Phe Phe Glu Pro Asp
            260                 265                 270
Glu Tyr Gly Val Ile Lys Val Cys Asp Glu Phe Pro Gly Phe Ser Arg
            275                 280                 285
Phe Lys Leu His Gln Pro Tyr Gly Ala Ala Ser Pro Lys Met Ile Ser
            290                 295                 300
Val Pro Arg Ser His Ala Lys His Pro Thr Asp Thr Tyr Pro Asp Ala
305                 310                 315                 320
Ser Glu Val Thr Ile Arg Lys Ala Ile Ala Arg Phe Leu Pro Glu Phe
            325                 330                 335
Lys Asp Lys Glu Leu Phe Asn Arg Thr Met Cys Trp Cys Thr Asp Thr
            340                 345                 350
Ala Asp Ala Asn Leu Leu Ile Cys Glu His Pro Lys Trp Lys Asn Phe
            355                 360                 365
Ile Leu Ala Thr Gly Asp Ser Gly His Ser Phe Lys Leu Leu Pro Asn
            370                 375                 380
Ile Gly Lys Tyr Val Val Glu Leu Leu Glu Gly Ser Leu Ser Gln Glu
385                 390                 395                 400
Met Ala Gly Ala Trp Arg Trp Arg Pro Gly Gly Asp Ala Leu Arg Ser
            405                 410                 415
Arg Arg Gly Ala Pro Ala Lys Asp Leu Ala Glu Met Pro Gly Trp Lys
            420                 425                 430
His Asp Ala His Leu
            435
```

<210> SEQ ID NO 35
<211> LENGTH: 440
<212> TYPE: PRT
<213> ORGANISM: Pyrenochaeta sp.

<400> SEQUENCE: 35

Met Ala Ala Ser Arg Ala Lys Thr Thr Val Ile Val Gly Gly Gly
1               5                   10                  15

Gly Thr Ile Gly Ser Ser Thr Ala Leu His Leu Leu Arg Ser Gly Tyr
            20                  25                  30

Thr Pro Ser Asn Ile Thr Val Leu Asp Thr Tyr Pro Ile Pro Ser Leu
            35                  40                  45

Gly Ser Ala Gly Asn Asp Leu Asn Lys Ile Met Gly Ile Arg Leu Arg
50                  55                  60

Asn Lys Val Asp Leu Gln Leu Ser Leu Glu Ala Arg Glu Met Trp Arg
65                  70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110

Thr Leu Leu Asp Ala Asn Ala Gly Leu Glu Glu Thr Asn Glu Trp Leu
            115                 120                 125

Asp Ser Glu Asp Glu Ile Leu Ala Arg Met Pro Leu Leu Ser Arg Glu
130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Gly Ala Gly Ser Phe Gln Gln Pro Leu
            180                 185                 190

Leu Ala Glu Gly Ile Cys Ile Gly Val Glu Thr Thr Asp Gly Thr Arg
            195                 200                 205

Tyr Tyr Ala Asp Lys Val Val Leu Ala Ala Gly Ala Trp Ser Pro Ala
210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Tyr Lys Asp Thr Pro
                245                 250                 255

Val Val Tyr Asn Gly Asp Leu Gly Phe Phe Phe Glu Pro Asn Glu His
            260                 265                 270

Gly Val Ile Lys Val Cys Asp Glu Phe Pro Gly Phe Thr Arg Phe Lys
            275                 280                 285

Lys His Gln Pro Phe Gly Ala Arg Ala Pro Lys Arg Ile Ser Val Pro
290                 295                 300

Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
                325                 330                 335

Lys Glu Leu Phe Asn Arg Ala Met Cys Trp Cys Thr Asp Thr Ala Asp
            340                 345                 350

Ala Ala Leu Leu Ile Cys Glu His Pro Gln Trp Lys Asn Phe Met Leu
            355                 360                 365

Ala Thr Gly Asp Ser Gly His Ser Phe Lys Leu Leu Pro Asn Ile Gly

```
                370                 375                 380
Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415

Arg Ala Ala Pro Ala Lys Asp Leu Ala Asp Met Pro Gly Trp Asn His
                420                 425                 430

Asp Glu Ser Pro Arg Ala Lys Leu
                435                 440

<210> SEQ ID NO 36
<211> LENGTH: 452
<212> TYPE: PRT
<213> ORGANISM: Arthrinium sp.

<400> SEQUENCE: 36

Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
                20                  25                  30

Thr Ala Thr Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
50                  55                  60

Asn Pro Val Asp Lys Gln Leu Ser Leu Glu Ala Gln Asp Met Trp Cys
65                  70                  75                  80

His Asp Glu Leu Phe Lys Pro Tyr Phe His Asn Thr Gly Arg Met Asp
                85                  90                  95

Cys Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
        115                 120                 125

Asp Ser Glu Asp Ala Ile Leu Ala Lys Met Pro Leu Leu Glu Arg Asp
130                 135                 140

Gln Ile Lys Gly Trp Lys Ala Ile Phe Ser Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Ala Gly Ala Phe Lys Lys Pro Leu
            180                 185                 190

Phe Ala Pro Asp Gly Ser Thr Cys Ile Gly Val Glu Thr Val Asp Gly
        195                 200                 205

Thr Lys Tyr Tyr Gly Asp Lys Val Val Leu Ala Ala Gly Ala Trp Ser
210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
                245                 250                 255

Cys Pro Val Val Tyr His Gly Asp Leu Gly Phe Phe Phe Glu Pro Asn
            260                 265                 270

Glu His Gly Val Ile Lys Val Cys Asp Glu Phe Pro Gly Phe Thr Arg
        275                 280                 285

Phe Leu Glu Gln His Gln Ser Tyr Gly Ala Pro Ala Pro Thr Arg Val
    290                 295                 300
```

Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
            325                 330                 335

Phe Gln Ser Lys Glu Leu Phe Asn Arg Ala Met Cys Trp Cys Thr Asp
            340                 345                 350

Thr Ala Asp Ala Ala Leu Leu Ile Cys Glu His Pro Arg Trp Arg Asn
            355                 360                 365

Phe Ile Leu Ala Thr Gly Asp Ser Gly His Ser Phe Lys Leu Leu Pro
370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gly Gln Gly Asp Ala Leu
            405                 410                 415

Lys Ser Arg Arg Ala Ala Pro Ala Lys Asp Leu Ala Asp Met Pro Gly
            420                 425                 430

Trp Asn His Asp Gly Asp Ser Gly Asn Ala Thr Ser Gly Thr Ser Ser
            435                 440                 445

Glu His Lys Leu
    450

<210> SEQ ID NO 37
<211> LENGTH: 440
<212> TYPE: PRT
<213> ORGANISM: Curvularia clavata

<400> SEQUENCE: 37

Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
            115                 120                 125

Asp Ser Glu Asp Glu Ile Leu Lys Lys Met Pro Leu Leu Asp Arg Glu
130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Gly Ala Gly Ser Phe Lys Gln Pro Leu
            180                 185                 190

Leu Ala Glu Gly Val Cys Ile Gly Val Glu Thr Val Asp Gly Thr Arg
            195                 200                 205

Tyr Tyr Ala Asp Lys Val Val Leu Ala Ala Gly Ala Trp Ser Pro Val
210                 215                 220

```
Leu Val Asp Leu Glu Asp Gln Cys Val Ser Lys Ala Trp Val Tyr Ala
225                 230                 235                 240

His Ile Gln Leu Thr Pro Glu Glu Ala Ala Glu Tyr Lys Asn Val Pro
            245                 250                 255

Val Val Tyr Asn Gly Asp Val Gly Phe Phe Glu Pro Asp Glu His
            260                 265                 270

Gly Val Ile Lys Val Cys Asp Glu Phe Pro Gly Phe Thr Arg Phe Lys
            275                 280                 285

Gln His Gln Pro Tyr Gly Ala Lys Ala Pro Lys Arg Ile Ser Val Pro
            290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
            355                 360                 365

Ala Thr Gly Asp Ser Gly His Thr Phe Lys Leu Leu Pro Asn Ile Gly
            370                 375                 380

Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415

Arg Ala Ala Pro Ala Lys Asp Leu Ala Asp Met Pro Gly Trp Lys His
                420                 425                 430

Asp Asp Val Val Lys Ser Lys Leu
            435                 440

<210> SEQ ID NO 38
<211> LENGTH: 441
<212> TYPE: PRT
<213> ORGANISM: Neocosmospora vasinfecta

<400> SEQUENCE: 38

Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe Phe His Asn Thr Gly Arg Leu Asp
                85                  90                  95

Cys Glu Ser Ser Ala Glu Gly Val Glu Gly Leu Arg Arg Glu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Glu Gly Gly Trp Leu
```

Ala Ala Ala Lys Ala Ile Asn Ala Ile Gly Glu Glu Leu Gln Arg Gln
145                 150                 155                 160

Gly Val Arg Phe Gly Phe Gly Ala Gly Ser Phe Lys Arg Pro Leu
        165                 170                 175

Phe Ala Asp Asp Gly Thr Thr Cys Ile Gly Val Glu Thr Val Asp Gly
        180                 185                 190

Thr Gln Tyr His Ala Asp Lys Val Val Leu Ala Gly Ala Trp Ser
        195                 200                 205

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
        245                 250                 255

Cys Pro Val Val Tyr His Gly Asp Val Gly Phe Phe Glu Pro Asn
        260                 265                 270

Glu Asn Gly Val Ile Lys Val Cys Asp Glu Phe Pro Gly Phe Thr Arg
        275                 280                 285

Phe Lys Gln His Gln Pro Tyr Gly Ala Pro Ala Pro Lys Pro Val Ser
290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
            325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
        355                 360                 365

Ile Leu Ala Thr Gly Asp Ser Gly His Ser Phe Lys Leu Leu Pro Ile
        370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
            405                 410                 415

Ser Ile Arg Ala Ala Pro Ala Lys Asp Leu Ala Asp Met Pro Gly Trp
        420                 425                 430

Lys His Asp Gln Asp Ser Glu Ser Arg
        435                 440

<210> SEQ ID NO 39
<211> LENGTH: 477
<212> TYPE: PRT
<213> ORGANISM: Cryptococcus neoformans

<400> SEQUENCE: 39

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Arg Ile Arg
    50                  55                  60

Asn Pro Val Asp Lys Gln Leu Ser Leu Glu Ala Arg Asp Met Trp Arg
65                  70                  75                  80

```
Asn Asp Glu Val Phe Lys Pro Tyr Phe His Asn Thr Gly Arg Leu Asp
                 85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
            115                 120                 125

Ser Thr Glu Asp Glu Ile Leu Ala Arg Ala Pro Leu Leu Asp Arg Lys
            130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
            195                 200                 205

Thr Gln Tyr Phe Ala Asp Lys Val Val Leu Ala Ala Gly Ala Trp Ser
        210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
            355                 360                 365

Ile Leu Ala Thr Gly Asp Ser Gly His Ser Phe Lys Ile Leu Pro Asn
        370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Arg Asp Leu Ala Asp Leu Pro Gly Trp
            420                 425                 430

Asn His Asp Glu Pro Ser Asp Asp Met Asp Val Lys Asp Val Ala
            435                 440                 445

Val Ser Leu Ala Ser Val Lys Ile Gly Glu Asn Ile Gly Glu Lys Val
        450                 455                 460

Val Glu Asp Gly Ala Arg Val Gly Val Lys Val Leu Ala
465                 470                 475

<210> SEQ ID NO 40
<211> LENGTH: 437
<212> TYPE: PRT
```

<213> ORGANISM: Phaeosphaeria nodorum

<400> SEQUENCE: 40

```
Met Ala Pro Ser Arg Ala Asn Th

Trp Arg Trp Arg Pro Gly Ser Gly Asp Ala Leu Lys Ser Arg Ser
                405                 410                 415

Ala Pro Ala Lys Asp Leu Ala Asp Met Pro Gly Trp Asn His Asp Lys
            420                 425                 430

Pro Arg Ala Asn Leu
        435

<210> SEQ ID NO 41
<211> LENGTH: 438
<212> TYPE: PRT
<213> ORGANISM: Aspergillus nidulans

<400> SEQUENCE: 41

Met Thr Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Ser Ile Arg Leu Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Met Ile Asp Val
                85                  90                  95

Ser Ser Thr Glu Glu Gly Ile Glu Gly Leu Arg Lys Lys Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
                340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 42
<211> LENGTH: 441
<212> TYPE: PRT
<213> ORGANISM: Ulocladium sp.

<400> SEQUENCE: 42

Met Ala Pro Asn Arg Ala Asn Ile Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
    130                 135                 140

Gln Ile Lys Gly Trp Lys Ala Val Phe Ser Glu Asp Gly Gly Trp Leu
145                 150                 155                 160

Ala Ala Ala Lys Ala Ile Asn Ala Ile Gly Arg Phe Leu Arg Asp Gln
                165                 170                 175

Gly Val Lys Phe Gly Phe Gly Ala Gly Ser Phe Lys Gln Pro Leu
            180                 185                 190

Leu Ala Glu Gly Val Cys Val Gly Val Glu Thr Val Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
                245                 250                 255

Val Val Tyr Asn Gly Asp Val Gly Phe Phe Phe Glu Pro Asp Glu Tyr

```
                260                 265                 270
Gly Val Ile Lys Val Cys Asp Glu Phe Pro Gly Phe Thr Arg Phe Lys
            275                 280                 285
Gln His Gln Pro Phe Gly Ala Ser Ala Pro Lys Arg Ile Ser Val Pro
            290                 295                 300
Arg Ser Ala Ala Lys His Pro Thr Asp Thr Tyr Pro Asp Ala Ser Glu
305                 310                 315                 320
Val Ser Ile Arg Lys Ala Ile Ala Thr Phe Leu Pro Lys Phe Thr Glu
            325                 330                 335
Lys Glu Val Phe Asn Arg His Leu Cys Trp Cys Thr Asp Thr Ala Asp
            340                 345                 350
Ala Ala Leu Leu Met Cys Glu His Pro Glu Trp Lys Asn Phe Val Leu
            355                 360                 365
Ala Thr Gly Asp Ser Gly His Thr Phe Lys Leu Pro Asn Ile Gly
            370                 375                 380
Lys His Val Val Glu Leu Leu Glu Gly Thr Leu Ala Asp Asp Leu Ala
385                 390                 395                 400
His Ala Trp Arg Trp Arg Pro Gly Thr Gly Asp Ala Leu Lys Ser Arg
            405                 410                 415
Arg Ala Ala Arg Ala Lys Asp Leu Ala Asp Met Pro Gly Trp Asn His
            420                 425                 430
Asp Gly Glu Ala Pro Arg Ala Lys Leu
            435                 440

<210> SEQ ID NO 43
<211> LENGTH: 437
<212> TYPE: PRT
<213> ORGANISM: Penicillium crysogenum

<400> SEQUENCE: 43

Met Ala His Ser Arg Glu Ser Thr Lys Ile Val Ile Val Gly Gly Gly
1               5                   10                  15
Gly Thr Met Gly Ser Ser Thr Ala Leu His Leu Ile Arg Ser Gly Tyr
            20                  25                  30
Thr Pro Ser Asn Ile Thr Val Leu Asp Val Tyr Pro Ile Pro Ser Leu
            35                  40                  45
Gln Ser Ala Gly Tyr Asp Leu Asn Lys Ile Met Ser Ile Arg Leu Arg
    50                  55                  60
Asn Gly Pro Asp Trp Gln Leu Ser Leu Glu Ala Leu Asp Met Trp Lys
65                  70                  75                  80
Asn Asp Pro Leu Phe Lys Pro Phe Phe His Asn Val Gly Met Leu Asp
                85                  90                  95
Cys Ser Ser Gln Glu Gly Ile Ala Ser Leu Arg Lys His Gln
                100                 105                 110
Asp Leu Ile Asp Ala Asn Ile Gly Leu Glu Lys Thr Asn Ile Trp Leu
            115                 120                 125
Glu Ser Glu Asp Asp Ile Leu Ala Lys Ala Pro His Phe Ala Arg Glu
    130                 135                 140
Gln Ile Lys Gly Trp Lys Gly Leu Phe Cys Gly Asp Gly Gly Trp Leu
145                 150                 155                 160
Ala Ala Ala Lys Ala Ile Asn Ala Ile Gly Thr Phe Leu Lys Ser Gln
            165                 170                 175
Gly Val Lys Phe Gly Phe Gly Ser Ala Gly Thr Phe Lys Arg Pro Leu
            180                 185                 190
```

```
Phe Ala Pro Asp Gly Ala Thr Cys Ser Gly Val Glu Thr Val Asp Gly
            195                 200                 205

Thr Lys Tyr Phe Ala Asp Lys Val Val Leu Ala Ala Gly Ala Trp Ser
    210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Pro Asn
                260                 265                 270

Glu His Gly Val Ile Lys Val Cys Asp Glu Phe Pro Gly Phe Ser Arg
    275                 280                 285

Phe Lys Leu His Gln Pro Tyr Gly Ala Thr Ser Pro Lys Leu Ile Ser
    290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
                340                 345                 350

Ala Asp Ala Asn Leu Leu Ile Cys Glu His Pro Lys Trp Lys Asn Phe
            355                 360                 365

Ile Leu Ala Thr Gly Asp Ser Gly His Ser Phe Lys Val Leu Pro Asn
        370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Gly Asp Ala Leu Lys Ser
                405                 410                 415

Lys Arg Ser Ala Pro Ala Lys Asp Leu Ala Glu Met Pro Gly Trp Lys
            420                 425                 430

His Asp Ala Lys Leu
            435

<210> SEQ ID NO 44
<211> LENGTH: 1314
<212> TYPE: DNA
<213> ORGANISM: Phaeosphaeria nodorum
<220> FEATURE:
<221> NAME/KEY: CDS
<222> LOCATION: (1)..(1314)

<400> SEQUENCE: 44 atg gcc ccg tcg cgt gct aat acg tcg gtc att gtg gtt ggt ggt ggt     48
Met Ala Pro Ser Arg Ala Asn Thr Ser Val Ile Val Val Gly Gly Gly
1               5                   10                  15 ggt acg att ggc tca tct acg gct ctg cat ctg gtc cgc tca ggc tat     96
Gly Thr Ile Gly Ser Ser Thr Ala Leu His Leu Val Arg Ser Gly Tyr
            20                  25                  30 acc ccg tcg aac gtg acg gtt ctg gat gca tac ccg att ccg agc tct    144
Thr Pro Ser Asn Val Thr Val Leu Asp Ala Tyr Pro Ile Pro Ser Ser
        35                  40                  45 cag agc gct ggc aac gac ctg aat aaa atc atg ggt gtc tct ctg cgt    192
Gln Ser Ala Gly Asn Asp Leu Asn Lys Ile Met Gly Val Ser Leu Arg
    50                  55                  60 aat ccg gtg gat ctg cag ctg gct ctg gaa gcg cgc caa atg tgg aac    240
Asn Pro Val Asp Leu Gln Leu Ala Leu Glu Ala Arg Gln Met Trp Asn
65                  70                  75                  80
```

```
gaa gac gaa ctg ttc aag aag ttt ttc cat aac acc ggc cgt ctg gat        288
Glu Asp Glu Leu Phe Lys Lys Phe Phe His Asn Thr Gly Arg Leu Asp
                85                  90                  95 tgc gcg cac ggt gaa aaa gat att gcc gac ctg aag agc ggc tat cag        336
Cys Ala His Gly Glu Lys Asp Ile Ala Asp Leu Lys Ser Gly Tyr Gln
            100                 105                 110 gct ctg gtg gat gcg ggt ctg gac gcc acg aac gaa tgg ctg gat agt        384
Ala Leu Val Asp Ala Gly Leu Asp Ala Thr Asn Glu Trp Leu Asp Ser
        115                 120                 125 gaa gac gaa atc ctg aaa cgt atg ccg ctg ctg tcc cgc gat caa att        432
Glu Asp Glu Ile Leu Lys Arg Met Pro Leu Leu Ser Arg Asp Gln Ile
    130                 135                 140 aaa ggc tgg aag gcg atc ttt tca aaa gac ggt ggt tgg ctg gca gca        480
Lys Gly Trp Lys Ala Ile Phe Ser Lys Asp Gly Gly Trp Leu Ala Ala
145                 150                 155                 160 gca aag gca att aat gca gtt ggt gaa tat ctg cgt gat cag ggc gtc        528
Ala Lys Ala Ile Asn Ala Val Gly Glu Tyr Leu Arg Asp Gln Gly Val
                165                 170                 175 cgc ttc ggt ttt tac ggc gcc ggt tct ttc aaa gca ccg ctg ctg gct        576
Arg Phe Gly Phe Tyr Gly Ala Gly Ser Phe Lys Ala Pro Leu Leu Ala
            180                 185                 190 gaa ggc gtc tgc atc ggt gtc gaa acc gtg gat ggc acg cgc tat tac        624
Glu Gly Val Cys Ile Gly Val Glu Thr Val Asp Gly Thr Arg Tyr Tyr
        195                 200                 205 gca gac aaa gtg gtt ctg gct gca ggt gca tgg tcg ccg acc ctg gtt        672
Ala Asp Lys Val Val Leu Ala Ala Gly Ala Trp Ser Pro Thr Leu Val
    210                 215                 220 gaa ctg cat gaa cag tgt gtg agc aaa gcg tgg gtt tac ggc cac att        720
Glu Leu His Glu Gln Cys Val Ser Lys Ala Trp Val Tyr Gly His Ile
225                 230                 235                 240 caa ctg acg ccg gaa gaa gcc gca cgt tat aag aac agc ccg gtc gtg        768
Gln Leu Thr Pro Glu Glu Ala Ala Arg Tyr Lys Asn Ser Pro Val Val
                245                 250                 255 tac aat ggc gat gtg ggc ttt ttc ttt gaa ccg aac gaa cat ggc gtt        816
Tyr Asn Gly Asp Val Gly Phe Phe Phe Glu Pro Asn Glu His Gly Val
            260                 265                 270 atc aaa gtc tgc gat gaa ttt ccg ggt ttt acc cgc ttc aag atg cac        864
Ile Lys Val Cys Asp Glu Phe Pro Gly Phe Thr Arg Phe Lys Met His
        275                 280                 285 cag ccg ttt ggt gcc aaa gca ccg aag cgt att agt gtg ccg cgc tcc        912
Gln Pro Phe Gly Ala Lys Ala Pro Lys Arg Ile Ser Val Pro Arg Ser
    290                 295                 300 cat gcc aaa cac ccg acc gat acg atc ccg gat gca agt gac gtt tcc        960
His Ala Lys His Pro Thr Asp Thr Ile Pro Asp Ala Ser Asp Val Ser
305                 310                 315                 320 att cgt cgc gct atc gcg acc ttt atg ccg cag ttc aag aac aaa aag       1008
Ile Arg Arg Ala Ile Ala Thr Phe Met Pro Gln Phe Lys Asn Lys Lys
                325                 330                 335 atg ttc aac caa gcg atg tgc tgg tgt acc gat acg gcc gac gct gcg       1056
Met Phe Asn Gln Ala Met Cys Trp Cys Thr Asp Thr Ala Asp Ala Ala
            340                 345                 350 ctg ctg att tgt gaa cat ccg gaa tgg aaa aac ttt gtt ctg gcg acc       1104
Leu Leu Ile Cys Glu His Pro Glu Trp Lys Asn Phe Val Leu Ala Thr
        355                 360                 365 ggc gat tca ggt cat tcg ttc aaa ctg ctg ccg aat atc ggc aag cac       1152
Gly Asp Ser Gly His Ser Phe Lys Leu Leu Pro Asn Ile Gly Lys His
    370                 375                 380 gtt gtc gaa ctg ctg gag ggt acg ctg gca gat gac ctg gca cac gca       1200
Val Val Glu Leu Leu Glu Gly Thr Leu Ala Asp Asp Leu Ala His Ala
385                 390                 395                 400
```

```
tgg cgt tgg cgt ccg ggt agt ggt gat gca ctg aaa agc cgt cgc tct        1248
Trp Arg Trp Arg Pro Gly Ser Gly Asp Ala Leu Lys Ser Arg Arg Ser
            405                 410                 415 gct ccg gcg aaa gac ctg gct gat atg ccg ggc tgg aac cat gac aaa        1296
Ala Pro Ala Lys Asp Leu Ala Asp Met Pro Gly Trp Asn His Asp Lys
            420                 425                 430 ccg cgt gct aat ctg taa                                                1314
Pro Arg Ala Asn Leu
        435

<210> SEQ ID NO 45
<211> LENGTH: 1326
<212> TYPE: DNA
<213> ORGANISM: Neocosmospora vasinfecta
<220> FEATURE:
<221> NAME/KEY: CDS
<222> LOCATION: (1)..(1326)

<400> SEQUENCE: 45 atg acg acc ccg cgt aaa gaa acg acg gtc ctg att att ggt ggt ggt         48
Met Thr Thr Pro Arg Lys Glu Thr Thr Val Leu Ile Ile Gly Gly Gly
1               5                   10                  15 ggc acg att ggt agc tcg acg gct ctg cat ctg ctg cgt gcc ggc tat         96
Gly Thr Ile Gly Ser Ser Thr Ala Leu His Leu Leu Arg Ala Gly Tyr
            20                  25                  30 acc ccg tct aac att acc gtg ctg gat acg tac ccg atc ccg agt gcc        144
Thr Pro Ser Asn Ile Thr Val Leu Asp Thr Tyr Pro Ile Pro Ser Ala
        35                  40                  45 cag tcc gca ggc aac gac ctg aat aaa att atg ggt atc cgt ctg cgc        192
Gln Ser Ala Gly Asn Asp Leu Asn Lys Ile Met Gly Ile Arg Leu Arg
    50                  55                  60 aat aaa gtt gat ctg caa ctg agc ctg gaa gcc cgt gat atg tgg cgc        240
Asn Lys Val Asp Leu Gln Leu Ser Leu Glu Ala Arg Asp Met Trp Arg
65                  70                  75                  80 aac gac gca ctg ttt cgt ccg ttt ttc cat aat acc ggc cgc ctg gac        288
Asn Asp Ala Leu Phe Arg Pro Phe Phe His Asn Thr Gly Arg Leu Asp
                85                  90                  95 tgc gaa agc tct gct gaa ggc gtg gaa ggt ctg cgt cgc gaa tat cag        336
Cys Glu Ser Ser Ala Glu Gly Val Glu Gly Leu Arg Arg Glu Tyr Gln
            100                 105                 110 aaa ctg gtg gaa gca ggc gtt ggt ctg gaa gaa acg cac gaa tgg ctg        384
Lys Leu Val Glu Ala Gly Val Gly Leu Glu Glu Thr His Glu Trp Leu
        115                 120                 125 gat agc gaa gaa gct att ctg gaa aaa gcg ccg ctg ctg caa cgt gaa        432
Asp Ser Glu Glu Ala Ile Leu Glu Lys Ala Pro Leu Leu Gln Arg Glu
    130                 135                 140 gaa att gaa ggt tgg aaa gcc atc tgg tct gaa gaa ggc ggt tgg ctg        480
Glu Ile Glu Gly Trp Lys Ala Ile Trp Ser Glu Glu Gly Gly Trp Leu
145                 150                 155                 160 gcg gcc gca aaa gct att aac gcg atc ggc gaa gaa ctg cag cgt caa        528
Ala Ala Ala Lys Ala Ile Asn Ala Ile Gly Glu Glu Leu Gln Arg Gln
                165                 170                 175 ggc gtt cgc ttc ggt ttt ggc ggt gcc ggt agt ttt aaa cgc ccg ctg        576
Gly Val Arg Phe Gly Phe Gly Gly Ala Gly Ser Phe Lys Arg Pro Leu
            180                 185                 190 ttc gca gat gac ggc acc acg tgt atc ggt gtc gaa acc gtg gat ggc        624
Phe Ala Asp Asp Gly Thr Thr Cys Ile Gly Val Glu Thr Val Asp Gly
        195                 200                 205 acg cag tat cat gcg gac aaa gtg gtt ctg gct gca ggt gct tgg tca        672
Thr Gln Tyr His Ala Asp Lys Val Val Leu Ala Ala Gly Ala Trp Ser
    210                 215                 220
```

```
ccg gcg ctg gtc gat ctg gaa gaa cag tgc tgt tcg aaa gcc tgg gtg    720
Pro Ala Leu Val Asp Leu Glu Glu Gln Cys Cys Ser Lys Ala Trp Val
225                 230                 235                 240 tac gca cac atg caa ctg acc ccg gaa gaa gcc gca gtt tat aaa ggc    768
Tyr Ala His Met Gln Leu Thr Pro Glu Glu Ala Ala Val Tyr Lys Gly
                245                 250                 255 tgc ccg gtc gtg tac cac ggc gat gtc ggc ttt ttc ttt gaa ccg aac    816
Cys Pro Val Val Tyr His Gly Asp Val Gly Phe Phe Phe Glu Pro Asn
            260                 265                 270 gaa aat ggt gtt att aaa gtc tgt gac gaa ttc ccg ggt ttt acg cgt    864
Glu Asn Gly Val Ile Lys Val Cys Asp Glu Phe Pro Gly Phe Thr Arg
        275                 280                 285 ttc aaa cag cat caa ccg tat ggt gcc ccg gca ccg aaa cct gtg agt    912
Phe Lys Gln His Gln Pro Tyr Gly Ala Pro Ala Pro Lys Pro Val Ser
    290                 295                 300 gtt ccg cgc tcc cat gcg aaa cac ccg acc gat acg tac ccg gac gct    960
Val Pro Arg Ser His Ala Lys His Pro Thr Asp Thr Tyr Pro Asp Ala
305                 310                 315                 320 tca gaa gaa tcg atc aaa cgt gcc gtg agt acc ttt ctg ccg cgc ttc   1008
Ser Glu Glu Ser Ile Lys Arg Ala Val Ser Thr Phe Leu Pro Arg Phe
                325                 330                 335 aaa gat aaa ccg ctg ttt aac cgt gca ctg tgc tgg tgt acc gat acg   1056
Lys Asp Lys Pro Leu Phe Asn Arg Ala Leu Cys Trp Cys Thr Asp Thr
            340                 345                 350 gcc gac tcc gca ctg ctg att tgc gaa cac ccg cgc tgg aaa aat ttt   1104
Ala Asp Ser Ala Leu Leu Ile Cys Glu His Pro Arg Trp Lys Asn Phe
        355                 360                 365 atc ctg gcg acc ggc gat agc ggt cat tct ttc aaa ctg ctg ccg att   1152
Ile Leu Ala Thr Gly Asp Ser Gly His Ser Phe Lys Leu Leu Pro Ile
    370                 375                 380 atc ggc aaa cac gtt gtc gaa ctg gtt gaa ggt cgt ctg gcg gat gac   1200
Ile Gly Lys His Val Val Glu Leu Val Glu Gly Arg Leu Ala Asp Asp
385                 390                 395                 400 ctg gct gaa gcg tgg cgt tgg cgt ccg ggt cag ggt gat gca cgt aaa   1248
Leu Ala Glu Ala Trp Arg Trp Arg Pro Gly Gln Gly Asp Ala Arg Lys
                405                 410                 415 agc att cgc gct gcg ccg gcg aaa gac ctg gcg gat atg ccg ggc tgg   1296
Ser Ile Arg Ala Ala Pro Ala Lys Asp Leu Ala Asp Met Pro Gly Trp
            420                 425                 430 aaa cac gac caa gac tcg gaa tca cgc tga                           1326
Lys His Asp Gln Asp Ser Glu Ser Arg
        435                 440

<210> SEQ ID NO 46
<211> LENGTH: 30
<212> TYPE: DNA
<213> ORGANISM: Artificial
<220> FEATURE:
<223> OTHER INFORMATION: primer

<400> SEQUENCE: 46
catgcctggt tgaaaaacga ggatgagatc                                    30

<210> SEQ ID NO 47
<211> LENGTH: 30
<212> TYPE: DNA
<213> ORGANISM: Artificial
<220> FEATURE:
<223> OTHER INFORMATION: primer

<400> SEQUENCE: 47
```

```
cggcatcttg gataagatct catcctcgtt                              30

<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
ttggacaacg agaaagagat cttatccaag                              30

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
ctggtggacc tgaaagatca atgttgctcg                              30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
agcatacacc caagccttcg agcaacattg                              30

<210> SEQ ID NO 51
<211> LENGTH: 30
<212> TYPE: DNA
<213> ORGANISM: Artificial
<220> FEATURE:
<223> OTHER INFORMATION: primer

<400> SEQUENCE: 51
gtggacctgg aaaaacaatg ttgctcgaag                              30

<210> SEQ ID NO 52
<211> LENGTH: 30
<212> TYPE: DNA
<213> ORGANISM: Artificial
<220> FEATURE:
<223> OTHER INFORMATION: primer

<400> SEQUENCE: 52
cagttgacgc ctaaagaggc cgctgagtat                              30

<210> SEQ ID NO 53
<211> LENGTH: 30
<212> TYPE: DNA
<213> ORGANISM: Artificial
<220> FEATURE:
<223> OTHER INFORMATION: primer

<400> SEQUENCE: 53
cacaactggg acacccttat actcagcggc                              30

<210> SEQ ID NO 54
<211> LENGTH: 30
<212> TYPE: DNA
<213> ORGANISM: Artificial
```

<220> FEATURE:
<223> OTHER INFORMATION: primer

<400> SEQUENCE: 54
cacaactggg caaccettat actcagcggc                                              30

<210> SEQ ID NO 55
<211> LENGTH: 1323
<212> TYPE: DNA
<213> ORGANISM: Curvularia clavata

<400> SEQUENCE: 55
atggccccga gtcgcgctaa cacgagcgtc attgtggtgg gtggtggtgg cacgattggt            60
tcctcaacgg cactgcatct ggtccgtagc ggctataccc cgtctaacat taccgtgctg           120
gacacgtacc cgatcccgag cgcccagtct gcaggcaacg atctgaataa aattatgggt           180
atccgtctgc gcaacaaagt tgatctgcag ctgtcactgg aagcccgtca aatgtggcgc           240
gaagatgacc tgtttaaaga atacttccat aacaccggcc gtctggattg cgcacacggt           300
gaagaaggtc tggccgacct gcgccaggct taccaagcgc tgctggatgc caacgcaggt           360
ctggaagaaa ccacggaatg gctggattca gaagacgaaa ttctgaagaa aatgccgctg           420
ctggatcgtg aacagatcaa aggttggaaa gccgtgtatt cgcaagatgg cggttggctg           480
gcggccgcaa aagccattaa tgcaatcggc gaatacctgc gcgcgcaggg cgttaaattc           540
ggttttggcg gtgctggttc ctttaaacag ccgctgctgg cagaaggcgt ctgcattggt           600
gtcgaaaccg tggatggcac gcgttattac gcggacaaag tggttctggc tgcaggtgca           660
tggagtccgg tgctggttga tctggaagac cagtgtgtgt ccaaagcgtg ggtttatgcg           720
catatccaac tgaccccgga agaagccgca gaatataaaa acgtcccggt cgtgtacaat           780
ggcgatgtgg gcttttcttt tgaaccggac gaacatggcg ttattaaagt ctgcgatgaa           840
tttccgggtt ttacccgctt caaacagcac caaccgtatg cgctaaagc gccgaaacgt           900
atctcagtgc cgcgttcggc tgcaaaacac ccgaccgata cgtacccgga cgcgagtgaa           960
aaatccattc gtaaagccat cgcaaccttt ctgccgaaat tcacggaaaa agaactgttt          1020
aatcgccatc tgtgctggtg taccgatacg gccgacgccg cactgctgat gtgtgaacac          1080
ccggaatgga aaactttgt tctggcgacc ggcgatagcg gtcatacgtt caaactgctg           1140
ccgaatattg gcaaacacgt tgtcgaactg ctggaaggta ccctggcaga agacctggct          1200
catgcgtggc gttggcgtcc gggtacgggt gatgcactga atctcgtcg cgctgcgccg           1260
gcgaaagacc tggcggatat gccgggctgg aaacacgacg atgtggtgaa aagcaaactg          1320
taa                                                                       1323

<210> SEQ ID NO 56
<211> LENGTH: 30
<212> TYPE: DNA
<213> ORGANISM: Artificial
<220> FEATURE:
<223> OTHER INFORMATION: primer

<400> SEQUENCE: 56
acggaatggc tgaaatcaga agacgaaatt                                              30

<210> SEQ ID NO 57
<211> LENGTH: 30
<212> TYPE: DNA
<213> ORGANISM: Artificial
<220> FEATURE:

<223> OTHER INFORMATION: primer

<400> SEQUENCE: 57 cggcatttc ttcagaattt cgtcttctga                                30

<210> SEQ ID NO 58
<211> LENGTH: 30
<212> TYPE: DNA
<213> ORGANISM: Artificial
<220> FEATURE:
<223> OTHER INFORMATION: primer

<400> SEQUENCE: 58
ctggattcag aaaagaaat tctgaagaaa                                 30

<210> SEQ ID NO 59
<211> LENGTH: 30
<212> TYPE: DNA
<213> ORGANISM: Artificial
<220> FEATURE:
<223> OTHER INFORMATION: primer

<400> SEQUENCE: 59
gattcagaag acaaaattct gaagaaaatg                                30

<210> SEQ ID NO 60
<211> LENGTH: 30
<212> TYPE: DNA
<213> ORGANISM: Artificial
<220> FEATURE:
<223> OTHER INFORMATION: primer

<400> SEQUENCE: 60
gattcagaag acgccattct gaagaaaatg                                30

<210> SEQ ID NO 61
<211> LENGTH: 27
<212> TYPE: DNA
<213> ORGANISM: Artificial
<220> FEATURE:
<223> OTHER INFORMATION: primer

<400> SEQUENCE: 61
atccagcagc ggcattttct tcagaat                                   27

<210> SEQ ID NO 62
<211> LENGTH: 30
<212> TYPE: DNA
<213> ORGANISM: Artificial
<220> FEATURE:
<223> OTHER INFORMATION: primer

<400> SEQUENCE: 62
ctggttgatc tgaaagacca gtgtgtgtcc                                30

<210> SEQ ID NO 63
<211> LENGTH: 30
<212> TYPE: DNA
<213> ORGANISM: Artificial
<220> FEATURE:
<223> OTHER INFORMATION: primer

<400> SEQUENCE: 63
gttgatctgg aaaacagtg tgtgtccaaa                                 30

<210> SEQ ID NO 64
<211> LENGTH: 30
<212> TYPE: DNA
<213> ORGANISM: Artificial
<220> FEATURE:
<223> OTHER INFORMATION: primer

<400> SEQUENCE: 64
cgcataaacc cacgctttgg acacacactg                                      30

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65
caactgaccc cgaaagaagc cgcagaatat                                      30

<210> SEQ ID NO 66
<211> LENGTH: 30
<212> TYPE: DNA
<213> ORGANISM: Artificial
<220> FEATURE:
<223> OTHER INFORMATION: primer

<400> SEQUENCE: 66
gaccgggacg tttttatatt ctgcggcttc                                      30

<210> SEQ ID NO 67
<211> LENGTH: 30
<212> TYPE: DNA
<213> ORGANISM: Artificial
<220> FEATURE:
<223> OTHER INFORMATION: primer

<400> SEQUENCE: 67
gaagaagccg caaaatataa aaacgtcccg                                      30

<210> SEQ ID NO 68
<211> LENGTH: 30
<212> TYPE: DNA
<213> ORGANISM: Artificial
<220> FEATURE:
<223> OTHER INFORMATION: primer

<400> SEQUENCE: 68
gccattgtac acgaccggga cgttttttata                                     30

<210> SEQ ID NO 69
<211> LENGTH: 30
<212> TYPE: DNA
<213> ORGANISM: Artificial
<220> FEATURE:
<223> OTHER INFORMATION: primer

<400> SEQUENCE: 69
gaagaagccg cacgttataa aaacgtcccg                                      30

<210> SEQ ID NO 70
<211> LENGTH: 30
<212> TYPE: DNA
<213> ORGANISM: Artificial
<220> FEATURE:
<223> OTHER INFORMATION: primer

```
<400> SEQUENCE: 70
gcagaatata aaaaagtccc ggtcgtgtac                                    30

<210> SEQ ID NO 71
<211> LENGTH: 30
<212> TYPE: DNA
<213> ORGANISM: Artificial
<220> FEATURE:
<223> OTHER INFORMATION: primer

<400> SEQUENCE: 71
gcccacatcg ccattgtaca cgaccgggac                                    30

<210> SEQ ID NO 72
<211> LENGTH: 30
<212> TYPE: DNA
<213> ORGANISM: Artificial
<220> FEATURE:
<223> OTHER INFORMATION: primer

<400> SEQUENCE: 72
ctgccgaaat tcaaagaaaa agaactgttt                                    30

<210> SEQ ID NO 73
<211> LENGTH: 30
<212> TYPE: DNA
<213> ORGANISM: Artificial
<220> FEATURE:
<223> OTHER INFORMATION: primer

<400> SEQUENCE: 73
gcacagatgg cgattaaaca gttcttttc                                     30

<210> SEQ ID NO 74
<211> LENGTH: 30
<212> TYPE: DNA
<213> ORGANISM: Artificial
<220> FEATURE:
<223> OTHER INFORMATION: primer

<400> SEQUENCE: 74
ctgccgaaat tccgtgaaaa agaactgttt                                    30
```

MODIFIED AMADORIASE AND METHOD FOR PRODUCING THE SAME, AGENT FOR IMPROVING SURFACTANT RESISTANCE OF AMADORIASE AND COMPOSITION FOR MEASURING HBA1C USING THE SAME

CROSS-REFERENCE TO RELATED APPLICATIONS

This application is a National Stage application of PCT/JP2014/071036, filed Aug. 8, 2014, which claims priority from Japanese application nos. JP 2013-167005, filed Aug. 9, 2013, and JP 2013-221515, filed Oct. 24, 2013.

TECHNICAL FIELD

The present invention relates to an amadoriase excellent in surfactant resistance, which can be advantageously used as a diagnostic enzyme for diabetes and in a kit for measuring a diabetes marker, and relates to a gene and recombinant DNA thereof and a method for producing an amadoriase excellent in surfactant resistance. The present invention further relates to a stabilizer and/or a buffer for the amadoriase of the present invention and a composition containing the same.

Glycated proteins are generated by non-enzymatic covalent bonding between aldehyde groups in aldoses, such as glucose (monosaccharides potentially containing aldehyde groups and derivatives thereof), and amino groups in proteins, followed by Amadori rearrangement. Examples of amino groups in proteins include α-amino groups of the amino terminus and side chain ε-amino groups of the lysine residue in proteins. Examples of known glycated proteins generated in vivo include glycated hemoglobin resulting from glycation of hemoglobin and glycated albumin resulting from glycation of albumin in the blood.

Among such glycated proteins generated in vivo, hemoglobin A1c (HbA1c) has drawn attention as a glycemic control marker significant for diagnosis of diabetic patients and control of conditions in the field of clinical diagnosis of diabetes mellitus. The blood HbA1c level reflects the average blood glucose level for a given period of time in the past, and the measured value thereof serves as a significant indicator for diagnosis and control of diabetes conditions.

As a method for quickly and easily measuring HbA1c, an enzymatic method using an amadoriase is proposed, in which HbA1c is decomposed with e.g., a protease, and α-fructosyl valyl histidine (hereinafter referred to as "αFVH") or α-fructosyl valine (hereinafter referred to as "αFV") released from a β chain amino terminus thereof is quantified (see, for example, Patent Literatures 1 to 7). In reality, the method of cleaving βFV from HbA1c is associated with the problem in that accurate measurement values cannot be obtained since the effect of contaminants and the like is significant. To obtain accurate measurement values, a method of measuring αFVH is mainly employed in particular at present.

An amadoriase catalyzes a reaction of oxidizing iminodiacetic acid or a derivative thereof (also referred to as an "Amadori compound") in the presence of oxygen to produce glyoxylic acid or α-ketoaldehyde, an amino acid or a peptide, and hydrogen peroxide.

Amadoriases have been found in bacteria, yeast, and fungi. In particular, amadoriases having enzyme activity to αFVH and/or αFV, which are useful for measurement of HbA1c are for example, amadoriases derived from the genera *Coniochaeta, Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Debaryomyces, Corynebacterium, Agrobacterium,* and *Arthrobacter* have been reported (e.g., Patent Documents 1 and 6 to 15 and Non-Patent Documents 1 to 11).

In some of the aforementioned documents, amadoriase is occasionally referred to as, for example, ketoamine oxidase, fructosyl amino acid oxidase, fructosyl peptide oxidase, or fructosyl amine oxidase.

Regarding measurement of HbA1c, it is known that reagent compositions for measurement contain excessive amounts of amadoriase. For example, when measuring HbA1c at a final concentration of 0.36 μM, amadoriase is used at a concentration of 1.4 kU/L, which is a concentration at which 1.4 mM of a substrate per minute can be reacted with the amadoriase (see Patent Literature 16). Measuring HbA1c using an amadoriase is currently carried out using an automated analyzer in the mainstream. The amadoriase and substrate are often reacted for 5 minutes to 25 minutes and subjected to measurement therein. The reason for including excessive amounts of amadoriase is to allow the amadoriase to react sufficiently with the substrate during a short measurement time as mentioned above; and further, if a substance which has a negative effect on the reactivity and stability of the amadoriase is present in the composition for measurement, excessive amounts of amadoriase must be formulated as a countermeasure against the effect.

As a pretreatment for measuring HbA1c in whole blood or erythrocytes by using an amadoriase, blood cells are lysed with a surfactant (see for example, Patent Literatures 2, 16 to 18). When degrading HbA1c with a protease, a surfactant is used in some methods as an accelerant (see, for example, Patent Literature 19). Therefore, surfactants are indispensable when measuring HbA1c with an amadoriase; however, the possibility is extremely high for the surfactant to denature the amadoriase when an HbA1c solution, which is treated with a surfactant and a protease, is mixed with an amadoriase solution and then a quantitative reaction of HbA1c is started, as well as during storage of a surfactant-amadoriase mixture. Presently used HbA1c measurement kits contain excessive amounts of amadoriase than required, and further are formulated together with stabilizers and are able to achieve accurate measurement; however, the cost of the kit inevitably increases due to use of excessive reagents. Further, if it is possible to use a more effective surfactant than those presently used, the degradation efficiency of HbA1c with protease can be improved and it his highly possible that the measurement sensitivity of HbA1c can be improved. In addition, surfactants have solubilizing effects on insoluble peptide fragments derived from hemoglobin and HbA1c. Because of the effect, the surfactant can prevent turbidity, thereby contributing to improvement of measurement accuracy. Therefore, regarding formulating an amadoriase as an enzyme for clinically diagnosing diabetes in a kit as a reagent, one desirable property of the enzyme is to be stable in a liquid containing a surfactant.

Although individual measurement conditions vary; disclosure of the stability of various amadoriases in liquids can be found in literature known in the art: in a case where 5 mM ethylenediaminetetraacetic acid and 3% glycine are added in a solution containing an amadoriase derived from *Coniochaeta* sp. NISL 9330 strain, it is reported that a residual activity of 79% is maintained 7 days later at 30° C. (see, for example, Patent Literature 20). Further, in another case where 3% L-alanine, 3% glycine or 3% sarcosine is added in a solution containing a fructosyl amino acid oxidase derived from *Fusarium oxysporum* IFO-9972 strain, it is reported that 100% residual activity is maintained 2 days later at 37° C. (see, for example, Patent Literature 21).

However, no surfactants are added to the above solutions containing amadoriase protein and the literature is silent on reducing effects of surfactants. Furthermore, amadoriases having high surfactant resistance have not been reported. Moreover, stabilizers and buffers maintaining the residual activity of an amadoriase or lowering a reduction of the residual activity in the presence of a surfactant have not been reported.

PRIOR ART DOCUMENTS

Patent Documents

Patent Document 1: WO 2004/104203
Patent Document 2: WO 2005/49857
Patent Document 3: JP 2001-95598 A
Patent Document 4: JP H05-33997 B (1993)
Patent Document 5: JP H11-127895 A (1999)
Patent Document 6: WO 97/13872
Patent Document 7: JP 2011-229526 A
Patent Document 8: JP 2003-235585 A
Patent Document 9: JP 2004-275013 A
Patent Document 10: JP 2004-275063 A
Patent Document 11: JP 2010-35469 A
Patent Document 12: JP 2010-57474 A
Patent Document 13: WO 2010/41715
Patent Document 14: WO 2010/41419
Patent Document 15: WO 2011/15325
Patent Document 16: WO 2012/020744
Patent Document 17: WO 2005/87946
Patent Document 18: WO 2002/06519
Patent Document 19: WO 2006/120976
Patent Document 20: JP 2006-325547 A
Patent Document 21: JP 2009-000128 A Non-Patent Documents Non-Patent Document 1: Biochem. Biophys. Res. Commun. 311, 104-11, 2003
Non-Patent Document 2: Biotechnol. Bioeng. 106, 358-66, 2010
Non-Patent Document 3: J. Biosci. Bioeng. 102, 241-3, 2006
Non-Patent Document 4: Eur. J. Biochem. 242, 499-505, 1996
Non-Patent Document 5: Arch. Microbiol. 178,344-50,2002
Non-Patent Document 6: Mar. Biotechnol. 6, 625-32, 2004
Non-Patent Document 7: Biosci. Biotechnol. Biochem. 59, 487-91, 1995
Non-Patent Document 8: Appl. Microbiol. Biotechnol. 74, 813-819, 2007
Non-Patent Document 9: Biosci. Biotechnol. Biochem. 66, 1256-61, 2002
Non-Patent Document 10: Biosci. Biotechnol. Biochem. 66, 2323-29, 2002
Non-Patent Document 11: Biotechnol. Letters 27, 27-32, 2005

SUMMARY OF INVENTION

Technical Problem

As described above, amadoriases have been used excessively in the art so as to sufficiently react with the substrate during measurement. Here, the present inventors newly found that a surfactant is a component which significantly negatively effects the stability of amadoriases. Therefore, if an enzyme having more excellent surfactant resistance than conventional amadoriases can be prepared, it is expected that such an enzyme will greatly contribute to attaining convenience in distribution (circulation) of the enzyme and kit, reduce amounts of the amadoriase and stabilizers formulated in the kit, thereby lowering costs, and enable formulating strong surfactants, thereby improving measurement sensitivity of HbA1c. Therefore, an object of the present invention is to provide an amadoriase having excellent surfactant resistance compared with conventional amadoriases, as well as to provide a reagent composition by which HbA1c or a glycated peptide derived from HbA1c can be quantified even in the presence of a surfactant.

Another object of the present invention is to provide a stabilizer and/or a buffer which maintains the residual activity of the amadoriase or lowers reduction of the residual activity in the presence of a surfactant and a composition containing these.

Solution to Problem

Under the present situation where information regarding conferring surfactant resistance to enzymes are barely disclosed, the present inventors have conducted intensive studies. As a result, the present inventors have found that the above objectives can be attained by introducing a particular amino acid residue substitutions into an amadoriase derived from the genus *Coniochaeta* and further by formulating to a reagent composition an amadoriase whose activity is retained even in the presence of a surfactant. The present inventors further found that if a particular stabilizer and/or buffer is(are) used, the residual activity of the amadoriase is maintained or reduction of residual activity in the presence of a surfactant is significantly lowered. Based on the findings, the present invention has been accomplished.

More specifically, the present invention is as follows.

1. An amadoriase having improved residual activity (%) 5 minutes after a surfactant is added compared with an amadoriase having an amino acid sequence as shown in SEQ ID No: 1, 3, or 37, and having
(i) an amino acid sequence having a deletion, insertion, addition, and/or substitution of one or several amino acids in the amino acid sequence as shown in SEQ ID No: 1, 3, or 37, and/or
(ii) an amino acid sequence having an identity of at least 70% with the amino acid sequence as shown in SEQ ID No: 1, 3, or 37.
2. The amadoriase according to [1], wherein the surfactant is an ionic surfactant.
3. The amadoriase according to [1] or [2], having substitution of one or more amino acid residues at a position corresponding to an amino acid selected from the group consisting of the following (i) to (xiv):
(i) asparagine at position 262,
(ii) valine at position 257,
(iii) glutamic acid at position 249,
(iv) glutamic acid at position 253,
(v) glutamine at position 337,
(vi) glutamic acid at position 340,
(vii) aspartic acid at position 232,
(viii) aspartic acid at position 129
(ix) aspartic acid at position 132,
(x) glutamic acid at position 133,
(xi) glutamic acid at position 44

(xii) glycine at position 256, (xiii) glutamic acid at position 231, and (xiv) glutamic acid at position 81, in the amino acid sequence as shown in SEQ ID NO: 1 or 3.

4. The amadoriase according to any one of [1] to [3], wherein the amino acids of the amino acid sequence as shown in SEQ ID NO: 1 or 3 have at least one of the following substations (i) to (xiv):

(i) asparagine at position 262 is substituted with histidine;

(ii) valine at position 257 is substituted with cysteine, serine, or threonine;

(iii) glutamic acid at position 249 is substituted with lysine, or arginine;

(iv) glutamic acid at position 253 is substituted with lysine, or arginine;

(v) glutamine at position 337 is substituted with lysine, or arginine;

(vi) glutamic acid at position 340 is substituted with proline;

(vii) aspartic acid at position 232 is substituted with lysine, or arginine;

(viii) aspartic acid at position 129 is substituted with lysine, or arginine;

(ix) aspartic acid at position 132 is substituted with lysine, or arginine;

(x) glutamic acid at position 133 is substituted with alanine, methionine, lysine, or arginine;

(xi) glutamic acid at position 44 is substituted with proline;

(xii) glycine at position 256 is substituted with lysine, or arginine;

(xiii) glutamic acid at position 231 is substituted with lysine, or arginine; and (xiv) glutamic acid at position 81 is substituted with lysine, or arginine.

5. The amadoriase according to any one of [1] to [4], wherein the amino acid sequence as shown in SEQ ID NO: 1 or 3 has substitution of amino acid residues selected from the group consisting of the following (i) to (ix):

(i) substitution of an amino acid at the position corresponding to glutamic acid at position 44 with proline and substitution of an amino acid at the position corresponding to glutamic acid at position 340 with proline;

(ii) substitution of an amino acid at the position corresponding to glutamic acid at position 44 with proline, substitution of an amino acid at the position corresponding to asparagine at position 262 with histidine, and substitution of an amino acid at the position corresponding to glutamic acid at position 340 with proline;

(iii) substitution of an amino acid at the position corresponding to glutamic acid at position 44 with proline, substitution of an amino acid at the position corresponding to valine at position 257 with cysteine, substitution of an amino acid at the position corresponding to asparagine at position 262 with histidine, and substitution of an amino acid at the position corresponding to glutamic acid at position 340 with proline;

(iv) substitution of an amino acid at the position corresponding to glutamic acid at position 44 with proline, substitution of an amino acid at the position corresponding to valine at position 257 with cysteine, substitution of an amino acid at the position corresponding to asparaginic at position 262 with histidine, substitution of an amino acid at the position corresponding to glutamic acid at position 340 with proline, and substitution of an amino acid at the position corresponding to aspartic acid at position 232 with lysine;

(v) substitution of an amino acid at the position corresponding to glutamic acid at position 44 with proline, substitution of an amino-acid at the position corresponding to valine at position 257 with cysteine, substitution of an amino acid at the position corresponding to asparagine at position 262 with histidine, substitution of an amino acid at the position corresponding to glutamic acid at position 340 with proline, and substitution of an amino acid at the position corresponding to glutamic acid at position 249 with lysine;

(vi) substitution of an amino acid at the position corresponding to glutamic acid at position 44 with proline, substitution of an amino acid at the position corresponding to glutamic acid at position 253 with lysine, substitution of an amino acid at the position corresponding to valine at position 257 with cysteine, substitution of an amino acid at the position corresponding to asparagine at position 262 with histidine, and substitution of an amino acid at the position corresponding to glutamic acid at position 340 with proline;

(vii) substitution of an amino acid at the position corresponding to glutamic acid at position 44 with proline, substitution of an amino acid at the position corresponding to glutamic acid at position 253 with lysine, substitution of an amino acid at the position corresponding to valine at position 257 with cysteine, substitution of an amino acid at the position corresponding to asparagine at position 262 with histidine, substitution of an amino acid at the position corresponding to glutamic acid at position 340 with proline, and substitution of an amino acid at the position corresponding to aspartic acid at position 129 with lysine.

(viii) substitution of an amino acid at the position corresponding to glutamic acid at position 44 with praline, substitution of an amino acid at the position corresponding to glutamic acid at position 133 with alanine, substitution of an amino acid at the position corresponding to glutamic acid at position 253 with lysine, substitution of an amino acid at the position corresponding to valine at position 257 with cysteine, substitution of an amino acid at the position corresponding to asparagine at position 262 with histidine, and substitution of an amino acid at the position corresponding to glutamic acid at position 340 with proline; and (ix) substitution of an amino acid at the position corresponding to glutamic acid at position 44 with proline, substitution of an amino acid at the position corresponding to glutamic acid at position 133 with alanine, substitution of an amino acid at the position corresponding to glutamic acid at position 253 with lysine, substitution of an amino acid at the position corresponding to valine at position 257 with cysteine, substitution of an amino acid at the position corresponding to asparagine at position 262 with histidine, substitution of an amino acid at the position corresponding to glutamine at position 337 with lysine, and substitution of an amino acid at the position corresponding to glutamic acid at position 340 with proline.

6. The amadoriase according to any one of [1] to [3], wherein amino acids of the amino acid sequence as shown in SEQ ID NO: 37 have at least one of the substitutions of the following (i) to (ix)

(i) glutamic acid at position 247 is substituted with lysine, or arginine;

(ii) glutamic acid at position 251 is substituted with lysine, or arginine;

(iii) threonine at position 335 is substituted with lysine, or arginine;

(iv) aspartic acid at position 230 is substituted with lysine, or arginine;

(v) aspartic acid at position 129 is substituted with lysine, or arginine;
(vi) aspartic acid at position 132 is substituted with lysine, or arginine;
(vii) glutamic acid at position 133 is substituted with alanine, methionine, lysine, or arginine;
(viii) asparagine at position 254 is substituted with lysine, or arginine; and
(ix) glutamic acid at position 229 is substituted with lysine, or arginine.

7. The amadoriase according to any one of [1] to [3] and [6], wherein the amino acid sequence as shown in SEQ ID NO: 37 has substitution of amino acid residues selected from the group consisting of the following (i) to (iv):
(i) substitution of an amino acid at the position corresponding to glutamic acid at position 251 with lysine and substitution of an amino acid at the position corresponding to threonine at position 335 with lysine;
(ii) substitution of an amino acid at the position corresponding to aspartic acid at position 132 with lysine and substitution of an amino acid at the position corresponding to threonine at position 335 with lysine;
(iii) substitution of an amino acid at the position corresponding to glutamic acid at position 133 with alanine and substitution of an amino acid at the position corresponding to threonine at position 335 with lysine; and
(iv) substitution of an amino acid at the position corresponding to glutamic acid at position 229 with lysine and substitution of an amino acid at the position corresponding to threonine at position 335 with lysine.

8. An amadoriase gene encoding the amino acid sequence according to any one of [1] to [7].
9. A recombinant vector comprising the amadoriase gene according to [8].
10. A host cell comprising the recombinant vector according to [9].
11. A method for producing an amadoriase comprising the following steps:
(i) culturing the host cell according to [10];
(ii) expressing an amadoriase gene contained in the host cell; and
(iii) isolating the amadoriase from a culture product.
12. A composition comprising the amadoriase according to any one of [1] to [7], for use in measuring glycated hemoglobin.
13. A composition comprising one or more surfactants and an amadoriase for measuring glycated hemoglobin.
14. The composition according to [13], wherein the amadoriase
(i) has a residual activity (%) of 15% or higher 5 minutes after a surfactant is added compared with a case where no surfactant is added, and/or
(ii) exhibits a difference of 0.006 or higher between absorbance at 751 nm after a colorimetric substrate sodium N-(carboxymethylaminocarbonyl)-4,4'-bis(dimethylamino) diphenylamine (DA-64) is added and reacted for 5 minutes, and absorbance at 751 nm 5 minutes after a control solution containing ion-exchanged water in place of a glycated amino acid solution or a glycated peptide solution is added, in the presence of a 0.04% final concentration of surfactant.
15. The composition according to [13] or [14], wherein the amadoriase has an amino acid sequence having an identity of at least 70% with the amino acid sequence as shown in SEQ ID No: 1, 3, 37 or 40.
16. The composition according to any one of [13] to [15], wherein the surfactant has a critical micelle concentration of 70 mM or lower.

17. The composition according to any one of [13] to [16], wherein the surfactant is one or more ionic surfactants selected from the group consisting of a quaternary ammonium salt represented by the following general formula (I):

[Formula 1]

[wherein, $R^1$ to $R^4$, which may be the same or different, each represent a substituted or unsubstituted $C_1$ to $C_{20}$ alkyl, alkenyl, aryl or benzyl; and $Z^-$ represents a monovalent anion],
a pyridinium salt represented by the following general formula (II):

[Formula 2]

[wherein, $R^5$ represents a substituted or unsubstituted $C_1$ to $C_{20}$ alkyl, a plurality of $R^a$, which may be the same or different, each represent a hydrogen atom or a substituted or unsubstituted $C_1$ to $C_{20}$ alkyl, alkenyl, aryl or benzyl; n represents an integer of 1 to 5; and $Z^-$ represents a monovalent anion],
a phosphonium salt represented by the general formula (III),

[Formula 3]

[wherein, $R^6$ to $R^9$, which may be the same or different, each represent a substituted or unsubstituted $C_1$ to $C_{20}$ alkyl, alkenyl, aryl or benzyl; and $Z^-$ represents a monovalent anion].
and sodium dodecyl sulfate.

18. The composition according to [17], wherein the surfactant is one or more ionic surfactants selected from the group consisting of
octyltrimethylammonium chloride, octyltrimethylammonium bromide, dioctyldimethylammonium chloride, dioctyldimethylammonium bromide, decyltrimethylammonium chloride, decyltrimethylammonium bromide, dodecyltrimethylammonium chloride, dodecyltrimethylammonium bromide, tetradecyltrimethylammonium chloride, tetradecyltrimethylammonium bromide, hexadecyltrimethylammonium chloride, hexadecyltrimethylammonium bromide, octadecyltrimethylammonium chloride, octadecyltrimethylammonium bromide, eicosyltrimethylammonium chloride and eicosyltrimethylammonium bromide, benzyldodecyldimethylammonium chloride, benzyldodecyldimethylammonium bromide, benzyltetradecyldimethylammonium chloride, benzyltetradecyldimethylammonium bromide, benzylcetyldimethylammonium chloride, and benzylcetyldimethylammonium bromide, 1-decylpyridinium chloride, 1-decylpyridinium bromide, 1-dodecylpyridinium chloride, 1-dodecylpyridinium bromide, 1-tetradecylpyridinium chloride, 1-tetradecylpyridinium bromide, 1-hexadecylpyridinium chloride, 1-hexadecylpyridinium bromide, N-cetyl-2-methylpyridinium chloride, N-cetyl-2-methylpyridinium bromide, N-cetyl-3-methylpyridinium chloride, N-cetyl-3-methylpyridinium bromide, N-cetyl-4-methylpyridinium chloride, N-cetyl-4-methylpyridinium bromide, 1-octadecylpyridinium chloride, 1-octadecylpyridinium bromide, 1-eicosylpyridinium chloride and 1-eicosylpyridinium bromide, tetraethylphosphonium chloride, tetraethylphosphonium bromide, tributylmethylphosphonium chloride, tributylmethylphosphonium bromide, tributylmethylphosphonium iodide, tetrabutylphosphonium chloride, tetrabutylphosphonium bromide, tetra-n-octylphosphonium chloride, tetra-n-octylphosphonium bromide, tributyldodecylphosphonium chloride, tributyldodecylphosphonium bromide, tributylhexadecylphosphonium chloride, tributylhexadecylphosphonium bromide, methyltriphenylphosphonium chloride, methyltriphenylphosphonium bromide, methyltriphenylphosphonium iodide, tetraphenylphosphonium chloride and tetraphenylphosphonium bromide.

19. The composition according to any one of [13] to [18], wherein the surfactant contained has a final concentration of 0.01% (w/v) or higher at the time of measurement.

20. The composition for use in measuring glycated hemoglobin according to [13], further comprising one or more buffers selected from the group consisting of a borate buffer, a Tris-HCl buffer, a phosphate buffer, a citrate buffer, a fumarate butter, a glutarate buffer, a citraconate buffer, a mesaconate buffer, a malonate buffer, a tartrate buffer, a succinate buffer, an adipate buffer, ACES (N-(2-acetamido)-2-aminoethanesulfonic acid) buffer, BES (N,N-bis(2-hydroxyethyl)-2-amino-ethanesulfonic acid) buffer, Bicin (N,N-bis(2-hydroxyethyl)glycine) buffer, Bis-Tris (bis(2-hydroxyethyl)iminotris(hydroxymethyl)methane) buffer, EPPS (4-(2-hydroxyethyl)-1-piperazine-propanesulfonic acid) buffer, HEPPSO (N-(hydroxyethyl)piperazine-N'-2-hydroxypropanesulfonic acid) buffer, MES (2-(n-morpholino)ethanesulfonic acid) buffer, MOPS (3-(N-morpholino)propanesulfonic acid) buffer, MOPSO (2-hydroxy-3-morpholino-propanesulfonate) buffer, PIPES (piperazine-N,N'-bis(2-ethanesulfonic acid)) buffer, POPSO (piperazine-1,4-bis(2-hydroxypropanesulfonic acid)) buffer, TAPS (N-tris(hydroxymethyl)methyl-3-aminopropanesulfonic acid) buffer, TAPSO (3-[N-tris(hydroxymethyl)methyl-amino]-2-hydroxypropanesulfonic acid) buffer, TES (N-tris(hydroxymethyl)methyl-2-amino-ethanesulfonic acid) buffer, Tricine (N-Tris(hydroxymethyl)methylglycine) buffer and a combination thereof.

21. The composition according to [20], comprising one or more buffers selected from the group consisting of a phosphate buffer having a final concentration in the measurement solution of 100 mM or higher, a citrate buffer having a final concentration in the measurement solution of 10 mM or higher, MES (2-(n-morpholino)ethanesulfonic acid) buffer having a final concentration in the measurement solution of 150 mM or higher, MOPS (3-(n-morpholino)propanesulfonic acid) buffer having a final concentration in the measurement solution of 100 mM or higher MOPSO (2-hydroxy-3-morpholino-propanesulfonic acid) buffer having a final concentration in the measurement solution of 100 mM or higher, and ACES (N-(2-acetamido)-2-aminoethanesulfonic acid) buffer having a final concentration in the measurement solution of 200 mM or higher.

22. The composition for use in measuring glycated hemoglobin according to [13], further comprising one or more stabilizers selected from the group consisting of phosphoric acid, a tricarboxylic acid, a dicarboxylic acid, a monocarboxylic acid, a compound represented by the formula (IV)

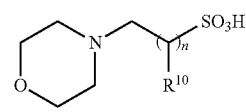

[Formula 4]

[wherein, n may be 0, 1, 2 or 3; and $R^{10}$ each independently represents H, OH, —CH$_2$OH or —COOH], ammonium sulfate and a combination thereof.

23. The composition according to [22], wherein the tricarboxylic acid is citric acid, or the dicarboxylic acid is selected from the group consisting of fumaric acid, glutaric acid, citraconic acid, mesaconic acid, malonic acid, tartaric acid, succinic acid, adipic acid, maleic acid, malic acid and combination of these; the mono-carboxylic acid is acetic acid; or the compound represented by the formula (IV) is selected from the group consisting of MES, MOPS, MOPSO and a combination thereof.

24. The composition according to [22] or [23], wherein the stabilizer is one or more stabilizers selected from the group consisting of phosphoric acid having a final concentration in the measurement solution of 2 mM or higher, citric acid having a final concentration in the measurement solution of 0.2 mM or higher, malic acid having a final concentration in the measurement solution of 2 mM or higher, maleic acid having a final concentration in the measurement solution of 2 mM or higher, citraconic acid having a final concentration in the measurement solution of 2 mM or higher, malonic acid having a final concentration in the measurement solution of 2 mM or higher, glutaric acid having a final concentration in the measurement solution of 2 mM or higher, tartaric acid having a final concentration in the measurement solution of 2 mM or higher, acetic acid having a final concentration in the measurement solution of 10 mM or higher, MES (2-(n-morpholino)ethanesulfonic acid) having a final concentration in the measurement solution of 10 mM or higher, MOPS (3-(n-morpholino)propanesulfonic acid) having a final concentration in the measurement solution of 10 mM or higher, MOPSO (2-hydroxy-3-morpholinopropanesulfonic acid) having a final concentration in the measurement solution of 10 mM or higher, ammonium sulfate having a final concentration in the measurement solution of 2 mM or higher and a combination thereof.

25. A composition for use in measuring glycated hemoglobin, comprising the buffer according to [20] or [21] and the stabilizer according to [22], [23] or [24].

26. The composition according to any one of [20] to [25], wherein the amadoriase is an amadoriase having an amino acid sequence represented by SEQ ID No: 1, SEQ ID No: 37 or SEQ ID No: 40 or the amadoriase according to any one of [1] to [7].

The specification incorporates the contents described in the specifications and/or drawings described in JP Patent Application Nos. 2013-167005 and 2013-221515, based on which the priority of this application is claimed.

Advantageous Effects of Invention

According to the present invention, it is possible to provide an amadoriase excellent in surfactant resistance which can advantageously be used as a diagnostic enzyme for diabetes in a kit for measuring a diabetes marker, as well as a gene encoding the amadoriase and the like.

Use of the amadoriase enables measurement of glycated hemoglobin even in the presence of high concentrations of surfactants. Further, use of the stabilizer and/or buffer of the present invention enables retaining the residual activity of an amadoriase or lowering reduction of the residual activity in the presence of a surfactant, as well as measuring glycated hemoglobin even in the presence of a surfactant at high concentrations.

BRIEF DESCRIPTION OF DRAWINGS

FIG. 1-1 shows alignment of amino acid sequences of various amadoriases known in the art.

FIG. 1-2 shows alignment of amino acid sequences of various amadoriases known in the art.

FIG. 1-3 shows alignment of amino acid sequences of various amadoriases known in the art.

FIG. 2 shows the measurement results of αFVH by using CFP-T7 in the presence of 0.01% CTAC in a mixture.

FIG. 3 shows the measurement results of αFVH by using CFP-T7 in the presence of 0.02% CTAC in a mixture.

DESCRIPTION OF EMBODIMENTS

Figure 2:
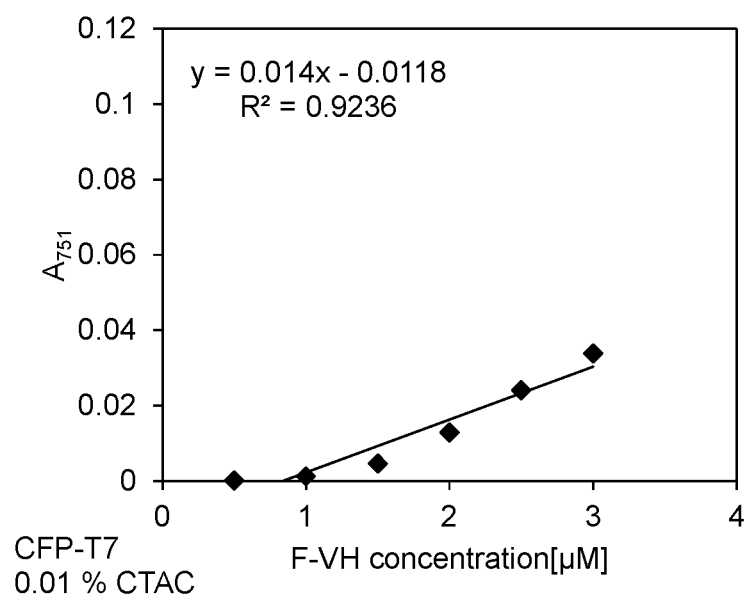

The present invention is described below in detail.
(Amadoriase)

Amadoriase, which is referred to also as e.g., ketoamine oxidase, fructosyl amino acid oxidase, fructosyl peptide oxidase or fructosyl amine oxidase, refers to an enzyme which catalyzes a reaction of oxidizing iminodiacetic acid or a derivative thereof (Amadori compound) in the presence of oxygen to generate glyoxylic acid or α-ketoaldehyde, an amino acid or a peptide and hydrogen peroxide. Amadoriases are widely distributed in nature and can be obtained by searching microorganism-, animal- or plant-derived enzymes. Regarding microorganisms, an amadoriase can be obtained from, for example, filamentous fungi, yeast or bacteria.

An aspect of the amadoriase of the present invention is directed to an amadoriase variant having improved surfactant resistance, which is produced based on an amadoriase derived from *Coniochaeta* having the amino acid sequences shown in SEQ ID NO: 1 or an amadoriase derived from *Curvularia clavata* having the amino acid sequence as shown in SEQ ID NO: 37. Examples of such variant include an amadoriase having an amino acid sequence having a high sequence identity (for example, 70% or higher, preferably 75% or higher, preferably 80% or higher, more preferably 85% or higher, further preferably 90% or higher, further preferably 95% or higher, further preferably 97% or higher, most preferably 99% or higher) with the amino acid sequence as shown in SEQ ID NO: 1 or SEQ ID No: 37; as well as an amadoriase having an amino acid sequence as shown in SEQ ID NO: 1 or SEQ ID No: 37, in which a single or several amino acids is(are) modified or mutated, in other words, deleted, substituted, added and/or inserted.

The amadoriase of the present invention may be prepared based on an amadoriase derived from any one of organism species such as the genera *Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Corynebacterium, Agrobacterium* and *Arthrobacter*. Among these, an amadoriase having surfactant resistance and/or having an amino acid sequence which has high sequence identity with that as shown in SEQ ID NO: 1 or SEQ ID No: 37, is preferable.

An amadoriase variant (modified amadoriase) having a modified surfactant resistance can be obtained by substituting, adding or deleting at least one amino acid residue of the amino acid sequence of an amadoriase.

As amino acid substitutions which provide improvement of surfactant resistance, substitutions of amino acids at the positions corresponding to the amino acids at the following positions in the amino acid sequence as shown in SEQ ID NO: 1 or 3, are mentioned.

(1) substitution of asparagine at position 262 with, e.g., histidine.

(2) substitution of valine at position 257 with, e.g., cysteine, serine, threonine.

(3) substitution of glutamic acid at position 249 with, e.g., lysine, arginine.

(4) substitution of glutamic acid at position 253 with, e.g., lysine, arginine.

(5) substitution of glutamine at position 337 with, e.g., lysine, arginine.

(6) substitution of glutamic acid at position 340 with, e.g., proline.

(7) substitution of aspartic acid at position 232 with, e.g., lysine, arginine.

(8) substitution of aspartic acid at position 129 with, e.g., lysine, arginine.

(9) substitution of aspartic acid at position 132 with, e.g., lysine, arginine.

(10) substitution of glutamic acid at position 133 with, e.g., alanine, methionine, lysine, arginine.

(11) substitution of glutamic acid at position 44 with, e.g., proline.

(12) substitution of glycine at position 256 with, e.g., lysine, arginine.

(13) substitution of glutamic acid at position 231 with, e.g., lysine, arginine.

(14) substitution of glutamic acid at position 81 with, e.g., lysine, arginine.

The amadoriase variant with improved surfactant resistance may have at least one of the above mentioned amino-acid substitutions and may have a plurality of amino-acid substitutions. The amadoriase variant has, for example, 1, 2, 3, 4, 5, 6, 7, 8, 9, 10, 11, 12, 13 or 14 of the above amino-acid substitutions.

Among such variants, those having amino-acid substitutions corresponding to the following amino acid positions are preferable.

(11)-(6) a variant having substitution of glutamic acid at position 44 and substitution of glutamic acid at position 340, for example, substitution of an amino acid at the position corresponding to glutamic acid at position 44 with proline, and substitution of an amino acid at the position corresponding to glutamic acid at position 340 with proline.

(11)-(1)-(6) a variant having substitution of glutamic acid at position 44, substitution of asparagine at position 262 and substitution of glutamic acid at position 340, for example, substitution of an amino acid at the position corresponding to glutamic acid at position 44 with proline, substitution of an amino acid at the position corresponding to asparagine at position 262 with histidine, and substitution of an amino acid at the position corresponding to glutamic acid at position 340 with proline.

(11)-(2)-(1)-(6) a variant having substitution of glutamic acid at position 44, substitution of valine at position 257, substitution of asparagine at position 262 and substitution of glutamic acid at position 340, for example, substitution of an amino acid at the position corresponding to glutamic acid at position 44 with proline, substitution of an amino acid at the position corresponding to valine at position 257 with cysteine, substitution of an amino acid at the position corresponding to asparagine at position 262 with histidine, and substitution of an amino acid at the position corresponding to glutamic acid at position 340 with proline.

(11)-(7)-(2)-(1)-(6) a variant having substitution of glutamic acid at position 44, substitution of valine at position 257, substitution of asparagine at position 262, substitution of glutamic acid at position 340 and substitution of aspartic acid at position 232, for example, substitution of an amino acid at the position corresponding to glutamic acid at position 44 with proline, substitution of an amino acid at the position corresponding to valine at position 257 with cysteine, substitution of an amino acid at the position corresponding to asparagine at position 262 with histidine, substitution of an amino acid at the position corresponding to glutamic acid at position 340 with proline, and substitution of an amino acid at the position corresponding to aspartic acid at position 232 with lysine or arginine.

(11)-(3)-(2)-(1)-(6) a variant having substitution of glutamic acid at position 44, substitution of valine at position 257, substitution of asparagine at position 262, substitution of glutamic acid at position 340 and substitution of glutamic acid at position 249, for example, substitution of an amino acid at the position corresponding to glutamic acid at position 44 with proline, substitution of an amino acid at the position corresponding to valine at position 257 with cysteine, substitution of an amino acid at the position corresponding to asparagine at position 262 with histidine, substitution of an amino acid at the position corresponding to glutamic acid at position 340 with proline, and substitution of an amino acid at the position corresponding to glutamic acid at position 249 with lysine or arginine.

(11)-(4)-(2)-(1)-(6) a variant having substitution of glutamic acid at position 44, substitution of glutamic acid at position 253, substitution of valine at position 257, substitution of asparagine at position 262 and substitution of glutamic acid at position 340, for example, substitution of an amino acid at the position corresponding to glutamic acid at position 44 with proline, substitution of an amino acid at the position corresponding to glutamic acid at position 253 with lysine or arginine, substitution of an amino acid at the position corresponding to valine at position 257 with cysteine, substitution of an amino acid at the position corresponding to asparagine at position 262 with histidine and substitution of an amino acid at the position corresponding to glutamic acid at position 340 with proline.

(11)-(8)-(4)-(2)-(1)-(6) a variant having substitution of glutamic acid at position 44, substitution of glutamic acid at position 253 substitution of valine at position 257, substitution of asparagine at position 262, substitution of glutamic acid at position 340 and substitution of aspartic acid at position 129, for example, substitution of an amino acid at the position corresponding to glutamic acid at position 44 with proline, substitution of an amino acid at the position corresponding to glutamic acid at position 253 with lysine or arginine, substitution of an amino acid at the position corresponding to valine at position 257 with cysteine, substitution of an amino acid at the position corresponding to asparagine at position 262 with histidine, substitution of an amino acid at the position corresponding to glutamic acid at position 340 with proline, and substitution of an amino acid at the position corresponding to aspartic acid at position 129 with lysine or arginine.

(11)-(10)-(4)-(2)-(1)-(6) a variant having substitution of glutamic acid at position 44, substitution of glutamic acid at position 133, substitution of glutamic acid at position 253, substitution of valine at position 257, substitution of asparagine at position 262 and substitution of glutamic acid at position 340, for example, substitution of an amino acid at the position corresponding to glutamic acid at position 44 with proline, substitution of an amino acid at the position corresponding to glutamic acid at position 133 with alanine, substitution of an amino acid at the position corresponding to glutamic acid at position 253 with lysine or arginine, substitution of an amino acid at the position corresponding to valine at position 257 with cysteine, substitution of an amino acid at the position corresponding to asparagine at position 262 with histidine, and substitution of an amino acid at the position corresponding to glutamic acid at position 340 with proline.

(11)-(10)-(4)-(2)-(1)-(5)-(6) a variant having substitution of glutamic acid at position 44, substitution of glutamic acid at position 133, substitution of glutamic acid at position 253, substitution of valine at position 257, substitution of asparagine at position 262, substitution of glutamine at position 337 with lysine, and substitution of glutamic acid at position 340, for example, substitution of an amino acid at the position corresponding to glutamic acid at position 44 with proline, substitution of an amino acid at the position corresponding to glutamic acid at position 133 with alanine, substitution of an amino acid at the position corresponding to glutamic acid at position 253 with lysine or arginine, substitution of an amino acid at the position corresponding to valine at position 257 with cysteine, substitution of an amino acid at the position corresponding to asparagine at position 262 with histidine, substitution of an amino acid at the position corresponding to glutamine at position 337 with lysine or arginine, and substitution of an amino acid at the position corresponding to glutamic acid at position 340 with proline.

The amadoriase variant excellent in surfactant resistance according to the present invention may have an amino-acid substitution(s) as mentioned above, which provides improved surfactant resistance to the amadoriase, regarding the amino acid sequence as shown in SEQ ID No: 1. The surfactant-resistant amadoriase variant of the present invention may further have a deletion, insertion, addition and/or substitution of a single or several amino acids (for example, 1 to 15 amino acids, 1 to 10 amino acids, preferably 1 to 5 amino acids, further preferably 1 to 3 amino acids, particularly preferably a single amino acid) at the positions excluding the positions of substituted amino acids. Further, the present invention encompasses an amadoriase variant with modified surfactant resistance, comprising an amino-acid substitution mutation providing improved surfactant resistance as mentioned above and an amino-acid substitution mutation providing improved properties other than surfactant resistance, such as substrate specificity and the like; wherein said variant has an amino acid sequence identity of 70% or higher, 75% or higher, 80% or higher, 90% or higher, further preferably 95% or higher, further preferably 97% or higher and particularly preferably 99% or higher, with the amino acid sequences as shown in SEQ ID NO: 1 or 3 albeit excluding those amino acids at the aforementioned amino-acid substitutions, and having an amadoriase activity.

The amadoriase having the amino acid sequence as shown in SEQ ID NO: 1 is an amadoriase (CFP-T7) derived from the genus *Coniochaeta* produced by *Escherichia coli* (deposition number: FERM BP-10593) having a recombinant plasmid designated as pKK223-3-CFP-T7 in WO2007/125779, and this is a modified amadoriase having excellent thermal stability previously found by the applicant. CFP-T7 is a triple variant obtained by sequentially introducing artificial mutations into a native amadoriase derived from the genus *Coniochaeta*, at positions 272, 302 and 388.

SEQ ID No: 3 represents the amino acid sequence of an amadoriase derived from the genus *Coniochaeta* obtained by introducing a mutation for improving substrate specificity (E98A) disclosed in WO2012/18094 and mutations for enhancing heat stability (F43Y, G184D, deletion of three amino acid residues in the carboxyl terminus) disclosed in WO 2007/125779 and WO2013/100006.

In the above amino-acid substitutions, the positions of amino acids represent the positions in the amino acid sequence of the amadoriase derived from the genus *Coniochaeta* and shown in SEQ ID No: 1. In the amino acid sequences of amadoriases derived from other species, the amino acids of the corresponding positions to the positions in the amino acid sequence as shown in SEQ ID NO: 1 are substituted. The meaning of the phrase "corresponding position(s)" will be described later.

As the amino-acid substitution providing improvement of surfactant resistance, amino-acid substitutions at the positions corresponding to amino acids at the following positions in the amino acid sequence as shown in SEQ ID No: 37 are mentioned.

(i) substitution of glutamic acid at position 247, e.g., substitution with lysine, arginine;

(ii) substitution of glutamic acid at position 251, e.g., substitution with lysine, arginine;

(iii) substitution of threonine at position 335, e.g., substitution with lysine, arginine;

(iv) substitution of aspartic acid at position 230, e.g., substitution with lysine, arginine;

(v) substitution of aspartic acid at position 129, e.g., substitution with lysine, arginine;

(vi) substitution of aspartic acid at position 132, e.g., substitution with lysine, arginine;

(vii) substitution of glutamic acid at position 133, e.g., alanine, methionine, lysine, arginine;

(viii) substitution of asparagine at position 254, e.g., substitution with lysine, arginine; and (ix) substitution of glutamic acid at position 229, e.g., substitution with lysine, arginine.

An amadoriase variant with improved surfactant resistance may have at least one of the above amino-acid substitutions or may have a plurality of amino-acid substitutions. For example, the amadoriase variant has 1, 2, 3, 4, 5, 6, 7, 8, or 9 of the above amino-acid substitutions.

Among them, variants having amino acid substitutions at the positions corresponding to the following amino acid positions are preferable; more specifically, the following (i) to (iv) in the amino acid sequence as shown in SEQ ID No: 37:

(i) a variant having substitution of an amino acid at the position corresponding to glutamic acid at position 251 with lysine and substitution of an amino acid at the position corresponding to threonine at position 335 with lysine;

(ii) a variant having substitution of an amino acid at the position corresponding to aspartic acid at position 132 with lysine and substitution of an amino acid at the position corresponding to threonine at position 335 with lysine;

(iii) a variant having substitution of an amino acid at the position corresponding to glutamic acid at position 133 with alanine and substitution of an amino acid at the position corresponding to threonine at position 335 with lysine; and (iv) a variant having substitution of an amino acid at the position corresponding to glutamic acid at position 229 with lysine and substitution of an amino acid at the position corresponding to threonine at position 335 with lysine.

(Obtaining a Gene Encoding an Amadoriase)

In order to obtain a gene in accordance with the present invention encoding these amadoriases (hereinafter, also referred to as merely "amadoriase gene"), gene cloning methods used in general can be carried out. For example, chromosomal DNA or mRNA can be extracted from a microorganism fungus body or various cells having an ability to produce an amadoriase by a conventional technique, such as a method described in "Current Protocols in Molecular Biology" (WILEY Interscience, 1989). In addition, cDNA can be synthesized using mRNA as a template. A chromosomal DNA or cDNA library can be made using the chromosomal DNA or cDNA obtained in such a manner.

Subsequently, DNA including the entire sequence of a target amadoriase gene can be obtained by a method of synthesizing an appropriate probe DNA based on the amino acid sequence of the aforementioned amadoriase and selecting an amadoriase gene from a chromosomal DNA or cDNA library using the probe DNA. Alternatively, an appropriate primer DNA may be produced based on the aforementioned amino acid sequence, a DNA including the target gene fragment encoding the amadoriase gene may be amplified by using an appropriate PCR technique, such as the 5' RACE or 3' RACE method, and the resulting DNA fragments may then be linked.

A preferable example of a gene encoding an amadoriase thus obtained is an example of an amadoriase gene derived from the genus *Coniochaeta* (JP 2003-235585 A) among others.

Such amadoriase genes are preferably linked to various vectors according to a conventional technique from the viewpoint of handleability. One example may be the recombinant plasmid pKK223-3-CFP (JP 2003-235585 A) in which the DNA encoding an amadoriase gene derived from the *Coniochaeta* sp. NISL9330 strain has been inserted into the pKK223-3 vector (GE Healthcare).

(Vector)

Vectors that can be used in the present invention are not limited to the aforementioned plasmid vectors and include, for example, any other vectors known in the art, such as bacteriophage or cosmid vectors. More specifically, for example, pBluescriptII SK+ (manufactured by Stratagene Corporation) is preferable.

(Mutation of Amadoriase Gene)

Mutation of an amadoriase gene can be performed by any known method depending on an intended form of mutation. More specifically, a method of bringing a chemical mutagen into contact with and allowing to act on an amadoriase gene or recombinant DNA comprising such gene integrated therein; an ultraviolet irradiation method; a genetic engineering technique; a method of making full use of a protein engineering technique; or various other methods can be used.

Examples of chemical mutagens used in the aforementioned mutation include hydroxyl amine, N-methyl-N'-nitro-N-nitrosoguanidine, nitrous acid, sulfurous acid, hydrazine, formic acid, and 5-bromouracil.

Various conditions for the above contact/reactions may be employed depending on the type of a drug to be used and are not particularly limited where a desired mutation can be actually induced in an amadoriase gene. In general, the desired mutation can be induced by contact/reactions performed at 20° C. to 80° C. for 10 minutes or longer, and preferably 10 to 180 minutes, with the use of the aforementioned drug at the concentration of 0.5 M to 12 M. The ultraviolet irradiation may be also performed according to a conventional technique as described above (Gendai Kagaku, pp. 24-30, June, 1989).

To take advantage of protein engineering techniques, a technique known as site-specific mutagenesis can in general be used. Examples include the Kramer method (Nucleic Acids Res., 12, 9441, 1984; Methods Enzymol., 154, 350, 1987; Gene, 37, 73, 1985), the Eckstein method (Nucleic Acids Res., 13, 8749, 1985; Nucleic Acids Res., 13, 8765, 1985; Nucleic Acids Res, 14, 9679, 1986), and the Kunkel method (Proc. Natl. Acad. Sci. U.S.A., 82, 488, 1985; Methods Enzymol., 154, 367, 1987). As examples of specific methods to convert the base sequence within DNA, commercially available kits (Transformer Mutagenesis Kit, Clonetech; EXOIII/Mung Bean Deletion Kit, Stratagene; Quick Change Site Directed Mutagenesis Kit, Stratagene and the like) can be used.

A technique known as a general PCR (Polymerase Chain Reaction) technique can also be used (Technique, 1, 11, 1989). In addition to the conventional genetic mutation technique, by an organic synthesis method or synthetic method of an enzyme, the modified amadoriase genes of interest can be also directly synthesized.

When determining or verifying the DNA nucleotide sequences of amadoriase genes obtained by the aforementioned methods, the multi-capillary DNA analysis system CEQ2000 (Beckman Coulter) and the like can, for example, be used.

(Transformation/Transduction)

The amadoriase genes obtained as described above are integrated into a vector such as a bacteriophage vector, a cosmid vector, or a plasmid vector used in transformation of a procaryotic or eucaryotic cell by a conventional technique, and a host corresponding to each vector can be transformed or transduced by a conventional technique. For example, the obtained recombinant DNA can be used on any microorganism, for example microorganism belonging to the genus *Escherichia*, specifically *E. coli* K-12 strain, preferably *E. coli* JM109 strain or *E. coli* DH5S strain (manufactured by Takara Bio Inc.) or an *E. coli* B strain, preferably *E. coli* BL21 strain (manufactured by Nippon gene Inc.) and the like to transform or transduce the same and to obtain the strain of interest.

(Identity of Amino Acid Sequences)

The identity of amino acid sequences can be obtained by calculation based on a program such as maximum matching and search homology of GENETYX Ver.11 (manufactured by GENETYX) or a program such as maximum matching and multiple alignment of DNASIS Pro (manufactured by Hitachi Software).

(Determination of the Position Corresponding to Amino Acid)

A "position corresponding to an amino acid" refers to the position present in the amino acid sequence of an amadoriase derived from other species which corresponds to the amino acid at a particular position in the amino acid sequence of the amadoriase derived from the genus *Coniochaeta* as shown in SEQ ID No: 1.

A method of identifying the "position corresponding to an amino acid" may be performed by comparing amino acid sequences using a known algorithm such as the Lipman-Pearson method to assign maximum identity to conserved amino acid residues present in the amino acid sequence of each amadoriase. The positions of the homologous amino acid residues in each of the amadoriase sequences can be determined, regardless of insertion or deletion of amino acid residue(s) in the amino acid sequences by aligning the amino acid sequences of the amadoriases by such method. Amino acid residues at homologous positions are thought to exist in similar positions in the three-dimensional structures, and amino acid residues at such homologous positions are expected to exert similar effects in terms of specificity of the amadoriase of interest.

Figure 3:
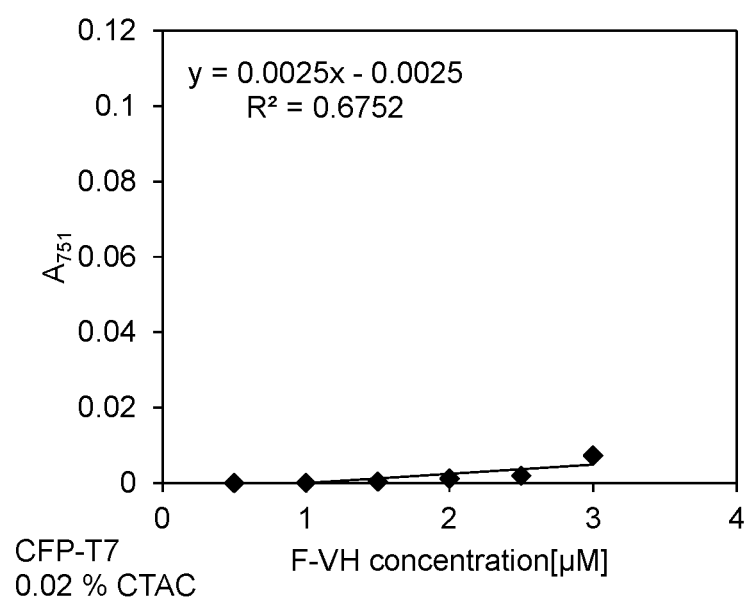

FIGS. 1-1, 1-2 and 1-3 show the sequences of amadoriases derived from various known species. The amino acid sequence as shown in SEQ ID No: 1 is shown in the uppermost stage. The sequences shown in FIG. 1 all have an identity of 70% or higher with the sequence of SEQ ID No: 1 and were aligned therewith based on a known algorithm.

In the figures, mutation points within the variants of the present invention are shown. From FIGS. 1-1, 1-2, 1-3, one can recognize the positions in the amino acid sequences of amadoriases derived from other species which correspond to the amino acid at a particular position in the amino acid sequence of the amadoriase derived from the genus *Coniochaeta*. FIGS. 1-1, 1-2 and 1-3 show the amino acid sequences of an amadoriase derived from the genus *Coniochaeta* (SEQ ID No: 1), an amadoriase derived from *Eupenicillium terrenum* (SEQ ID No: 34), a ketoamine oxidase derived from *Pyrenochaeta* sp. (SEQ ID No: 35), a ketoamine oxidase derived from *Arthrinium* sp. (SEQ ID No: 36), a ketoamine oxidase derived from *Curvularia clavata* (SEQ ID No: 37), a ketoamine oxidase derived from *Nencosmospora vasinfecta* (SEQ ID No: 38), a fructosyl amino acid oxidase derived from *Cryptococcus neoformans* (SEQ ID No: 39), a fructosyl peptide oxidase derived from *Phaeosphaeria nodorum* (SEQ ID No: 40), a fructosyl amino acid oxidase derived from *Aspergillus nidulans* (SEQ ID No: 41), a fructosyl amino acid oxidase derived from *Ulocladium* sp. (SEQ ID No: 42), and a fructosyl amino acid oxidase derived from *Penicillium crysogenum* (SEQ ID No: 43).

(Position Corresponding to Substitution Site)

In the present invention, the phrase "the position corresponding to glutamic acid at position 44 in the amino acid sequence described in SEQ ID No: 1" refers to an amino acid corresponding to glutamic acid at position 44 of an amadoriase of SEQ ID No: 1, when the identified amino acid sequence of an amadoriase is compared with the amino acid sequence of the amadoriase derived from the genus *Coniochaeta* and shown in SEQ ID No: 1. Based on this, using the method of specifying the "amino acid residue at the corresponding position", the corresponding position can be specified with reference to FIG. 1-1 in which amino acid sequences are aligned.

More specifically, the position corresponding to glutamic acid at position 44 in the amino acid sequence described in SEQ ID No: 1 is lysine at position 44 in the amadoriase derived from *Eupenicillium terrenum*, proline at position 44 in the ketoamine oxidase derived from *Pyrenochaeta* sp., proline at position 44 in the ketoamine oxidase derived from *Arthrinium* sp., proline at position 44 in the ketoamine oxidase derived from *Curvularia clavata*, proline at position 44 in the ketoamine oxidase derived from *Neocosmospora vasinfecta*, leucine at position 44 in the fructosyl amino acid oxidase derived from *Cryptococcus neoformans*, proline at position 44 in the fructosyl peptide oxidase derived from *Phaeosphaeria nodorum*, proline at position 43 in the fructosyl amino acid oxidase derived from *Aspergillus nidulans*, proline at position 44 in the fructosyl amino acid oxidase derived from *Ulocladium* sp., and proline at position 44 in the fructosyl amino acid oxidase derived from *Penicillium crysogenum*.

"The position corresponding to glutamic acid at position 81 in the amino acid sequence described in SEQ ID No: 1" refers to an amino acid corresponding to glutamic acid at position 81 of an amadoriase of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-1 in which amino acid sequences are aligned.

More specifically, the position corresponding to glutamic acid at position 81 in the amino acid sequence described in SEQ ID No: 1 is asparagine at position 81 in the amadoriase derived from *Eupenicillium terrenum*, glutamic acid at position 81 in the ketoamine oxidase derived from *Pyrenochaeta* sp., histidine at position 81 in the ketoamine oxidase derived from *Arthrinium* sp., glutamic acid at position 81 in the ketoamine oxidase derived from *Curvularia clavata*, asparagine at position 81 in the ketoamine oxidase derived from *Neocosmospora vasinfecta*, asparagine at position 81 in the fructosyl amino acid oxidase derived from *Cryptococcus neoformans*, glutamic acid at position 81 in the fructosyl peptide oxidase derived from *Phaeosphaeria nodorum*, asparagine at position 80 in the fructosyl amino acid oxidase derived from *Aspergillus nidulans*, glutamic acid at position 81 in the fructosyl amino acid oxidase derived from *Ulocladium* sp., and asparagine at position 81 in the fructosyl amino acid oxidase derived from *Penicillium crysogenum*.

"The position corresponding to glutamic acid at position 133 in the amino acid sequence described in SEQ ID No: 1" refers to an amino acid corresponding to glutamic acid at position 133 of the amino acid sequence described in SEQ ID No: 1, when the identified amino acid sequence of an amadoriase is compared with the amino acid sequence of the amadoriase derived from the genus *Coniochaeta* and shown in SEQ ID No: 1. This can be specified based on FIG. 1-1, in which amino acid sequences are aligned by the aforementioned method.

More specifically, the position corresponding to glutamic acid at position 133 in the amino acid sequence described in SEQ ID No: 1 is glutamic acid at position 133 in the amadoriase derived from *Eupenicillium terrenum*, glutamic acid at position 133 in the ketoamine oxidase derived from *Pyrenochaeta* sp., alanine at position 133 in the ketoamine oxidase derived from *Arthrinium* sp., glutamic acid at position 133 in the ketoamine oxidase derived from *Curvularia clavata*, alanine at position 133 in the ketoamine oxidase derived from *Neocosmospora vasinfecta*, glutamic acid at position 133 in the fructosyl amino acid oxidase derived from *Cryptococcus neoformans*, glutamic acid at position 131 in the fructosyl peptide oxidase derived from *Phaeosphaeria nodorum*, glutamic acid at position 132 in the fructosyl amino acid oxidase derived from *Aspergillus nidulans*, lysine at position 133 in the fructosyl amino acid oxidase derived from *Ulocladium* sp., and aspartic acid at position 133 in the fructosyl amino acid oxidase derived from *Penicillium crysogenum*.

"The position corresponding to glutamic acid at position 253 in the amino acid sequence described in SEQ ID No: 1" refers to an amino acid corresponding to glutamic acid at position 253 of amino acid sequence of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-2 in which amino acid sequences are aligned.

More specifically, the position corresponding to glutamic acid at position 253 in the amino acid sequence described in SEQ ID No: 1 is alanine at position 253 in the amadoriase derived from *Eupenicillium terrenum*, alanine at position 251 in the ketoamine oxidase derived from *Pyrenochaeta* sp., glutamic acid at position 253 in the ketoamine oxidase derived from *Arthrinium* sp., glutamic acid at position 251 in the ketoamine oxidase derived from *Curvularia clavata*, valine at position 253 in the ketoamine oxidase derived from *Neocosmospora vasinfecta*, glutamic acid at position 253 in the fructosyl amino acid oxidase derived from *Cryptococcus neoformans*, arginine at position 249 in the fructosyl peptide oxidase derived from *Phaeosphaeria nodorum*, alanine at position 253 in the fructosyl amino acid oxidase derived from *Aspergillus nidulans*, glutamic acid at position 251 in the fructosyl amino acid oxidase derived from *Ulocladium* sp., and glutamine at position 253 in the fructosyl amino acid oxidase derived from *Penicillium crysogenum*.

"The position corresponding to glycine at position 256 in the amino acid sequence described in SEQ ID No: 1" refers to an amino acid corresponding to glycine at position 256 of an amadoriase of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-2 in which amino acid sequences are aligned.

More specifically, the position corresponding to glycine at position 256 in the amino acid sequence described in SEQ ID No: 1 is asparagine at position 256 in the amadoriase derived from *Eupenicillium terrenum*, aspartic acid at position 254 in the ketoamine oxidase derived from *Pyrenochaeta* sp., glycine at position 256 in the ketoamine oxidase derived from *Arthrinium* sp., asparagine at position 254 in the ketoamine oxidase derived from *Curvularia clavata*, glycine at position 256 in the ketoamine oxidase derived from *Neocosmospora vasinfecta*, glutamic acid at position 256 in the fructosyl amino acid oxidase derived from *Cryptococcus neoformans*, asparagine at position 252 in the fructosyl peptide oxidase derived from *Phaeosphaeria nodorum*, asparagine at position 256 in the fructosyl amino acid oxidase derived from *Aspergillus nidulans*, asparagine at position 254 in the fructosyl amino acid oxidase derived from *Ulocladium* sp., and aspartic acid at position 256 in the fructosyl amino acid oxidase derived from *Penicillium crysogenum*.

"The position corresponding to valine at position 257 in the amino acid sequence described in SEQ ID No: 1" refers to an amino acid corresponding to valine at position 257 of an amadoriase of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-2 in which amino acid sequences are aligned.

More specifically, the position corresponding to valine at position 257 in the amino acid sequence described in SEQ ID No: 1 is valine at position 257 in the amadoriase derived from *Eupenicillium terrenum*, threonine at position 255 in the ketoamine oxidase derived from *Pyrenochaeta* sp., cysteine at position 257 in the ketoamine oxidase derived from *Arthrinium* sp., valine at position 255 in the ketoamine oxidase derived from *Curvularia clavata*, cysteine at position 257 in the ketoamine oxidase derived from *Neocosmospora vasinfecta*, cysteine at position 257 in the fructosyl amino acid oxidase derived from *Cryptococcus neoformans*, serine at position 253 in the fructosyl peptide oxidase derived from *Phaeosphaeria nodorum*, threonine at position 257 in the fructosyl amino acid oxidase derived from *Aspergillus nidulans*, valine at position 255 in the fructosyl amino acid oxidase derived from *Ulocladium* sp., and valine at position 257 in the fructosyl amino acid oxidase derived from *Penicillium crysogenum*.

"The position corresponding to asparagine at position 262 in the amino acid sequence described in SEQ ID No: 1" refers to an amino acid corresponding to asparagine at position 262 of an amadoriase of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-2 in which amino acid sequences are aligned.

More specifically, the position corresponding to asparagine at position 262 in the amino acid sequence described in SEQ ID No: 1 is aspartic acid at position 262 in the amadoriase derived from *Eupenicillium terrenum*, asparagine at position 260 in the ketoamine oxidase derived from *Pyrenochaeta* sp., histidine at position 262 in the ketoamine oxidase derived from *Arthrinium* sp., asparagine at position 260 in the ketoamine oxidase derived from *Curvularia clavata*, histidine at position 262 in the ketoamine oxidase derived from *Neocosmospora vasinfecta*, asparagine at position 262 in the fructosyl amino acid oxidase derived from *Cryptococcus neoformans*, asparagine at position 258 in the fructosyl peptide oxidase derived from *Phaeosphaeria nodorum*, aspartic acid at position 262 in the fructosyl amino acid oxidase derived from *Aspergillus nidulans*, asparagine at position 260 in the fructosyl amino acid oxidase derived from *Ulocladium* sp., and aspartic acid at position 262 in the fructosyl amino acid oxidase derived from *Penicillium crysogenum*.

"The position corresponding to glutamine at position 337 in the amino acid sequence described in SEQ ID No: 1" refers to an amino acid corresponding to glutamine at position 337 of an amadoriase of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-2 in which amino acid sequences are aligned.

More specifically, the position corresponding to glutamine at position 337 in the amino acid sequence described in SEQ ID No: 1 is lysine at position 337 in the amadoriase derived from *Eupenicillium terrenum*, lysine at position 335 in the ketoamine oxidase derived from *Pyrenochaeta* sp., glutamine at position 338 in the ketoamine oxidase derived from *Arthrinium* sp., threonine at position 335 in the ketoamine oxidase derived from *Curvularia clavata*, lysine at position 337 in the ketoamine oxidase derived from *Neocosmospora vasinfecta*, lysine at position 337 in the fructosyl amino acid oxidase derived from *Cryptococcus neoformans*, lysine at position 333 in the fructosyl peptide oxidase derived from *Phaeosphaeria nodorum*, asparagine at position 337 in the fructosyl amino acid oxidase derived from *Aspergillus nidulans*, threonine at position 335 in the fructosyl amino acid oxidase derived from *Ulocladium* sp., and lysine at position 337 in the fructosyl amino acid oxidase derived from *Penicillium crysogenum*.

"The position corresponding to glutamic acid at position 340 in the amino acid sequence described in SEQ ID No: 1" refers to an amino acid corresponding to glutamic acid at position 340 of an amadoriase of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-2 in which amino acid sequences are aligned.

More specifically, the position corresponding to glutamic acid at position 340 in the amino acid sequence described in SEQ ID No: 1 is glutamic acid at position 340 in the amadoriase derived from *Eupenicillium terrenum*, glutamic acid at position 338 in the ketoamine oxidase derived from *Pyrenochaeta* sp., glutamic acid at position 341 in the ketoamine oxidase derived from *Arthrinium* sp., glutamic acid at position 338 in the ketoamine oxidase derived from *Curvularia clavata*, proline at position 340 in the ketoamine oxidase derived from *Neocosmospora vasinfecta*, glutamic acid at position 340 in the fructosyl amino acid oxidase derived from *Cryptococcus neoformans*, lysine at position 336 in the fructosyl peptide oxidase derived from *Phaeosphaeria nodorum*, glutamic acid at position 340 in the fructosyl amino acid oxidase derived from *Aspergillus nidulans*, glutamic acid at position 338 in the fructosyl amino acid oxidase derived from *Ulocladium* sp., and glutamic acid at position 340 in the fructosyl amino acid oxidase derived from *Penicillium crysogenum*.

"The position corresponding to aspartic acid at position 129 in the amino acid sequence described in SEQ ID No: 1" refers to an amino acid corresponding to aspartic acid at position 129 of an amadoriase of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-1 in which amino acid sequences are aligned.

More specifically, the position corresponding to aspartic acid at position 129 in the amino acid sequence described in SEQ ID No: 1 is glutamic acid at position 129 in the amadoriase derived from *Eupenicillium terrenum*, aspartic acid at position 129 in the ketoamine oxidase derived from *Pyrenochaeta* sp., aspartic acid at position 129 in the ketoamine oxidase derived from *Arthrinium* sp., aspartic acid at position 129 in the ketoamine oxidase derived from *Curvularia clavata*, aspartic acid at position 129 in the ketoamine oxidase derived from *Neocosmospora vasinfecta*, serine at position 129 in the fructosyl amino acid oxidase derived from *Cryptococcus neoformans*, aspartic acid at position 127 in the fructosyl peptide oxidase derived from *Phaeosphaeria nodorum*, glutamic acid at position 128 in the fructosyl amino acid oxidase derived from *Aspergillus nidulans*, aspartic acid at position 129 in the fructosyl amino acid oxidase derived from *Ulocladium* sp., and glutamic acid at position 129 in the fructosyl amino acid oxidase derived from *Penicillium crysogenum*.

"The position corresponding to aspartic acid at position 132 in the amino acid sequence described in SEQ ID No: 1" refers to an amino acid corresponding to aspartic acid at position 132 of an amadoriase of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-1 in which amino acid sequences are aligned.

More specifically, the position corresponding to aspartic acid at position 132 in the amino acid sequence described in SEQ ID No: 1 is aspartic acid at position 132 in the amadoriase derived from *Eupenicillium terrenum*, aspartic acid at position 132 in the ketoamine oxidase derived from *Pyrenochaeta* sp., aspartic acid at position 132 in the ketoamine oxidase derived from *Arthrinium* sp., aspartic acid at position 132 in the ketoamine oxidase derived from *Curvularia clavata*, glutamic acid at position 132 in the ketoamine oxidase derived from *Neocosmospora vasinfecta*, aspartic acid at position 132 in the fructosyl amino acid oxidase derived from *Cryptococcus neoformans*, aspartic acid at position 130 in the fructosyl peptide oxidase derived from *Phaeosphaeria nodorum*, aspartic acid at position 131 in the fructosyl amino acid oxidase derived from *Aspergillus nidulans*, aspartic acid at position 132 in the fructosyl amino acid oxidase derived from *Ulocladium* sp., and aspartic acid at position 132 in the fructosyl amino acid oxidase derived from *Penicillium crysogenum*.

"The position corresponding to glutamic acid at position 231 in the amino acid sequence described in SEQ ID) No: 1" refers to an amino acid corresponding to glutamic acid at position 231 of an amadoriase of SEQ ID No: 1, when the identified amino acid sequence of an amadoriase is compared with the amino acid sequence of the amadoriase derived from the genus *Coniochaeta* and shown in SEQ ID) No: 1. This can be also specified by the aforementioned method with reference to FIG. 1-2 in which amino acid sequences are aligned.

More specifically, the position corresponding to glutamic acid at position 231 in the amino acid sequence described in SEQ ID No: 1 is glutamic acid at position 231 in the amadoriase derived from *Eupenicillium terrenum*, glutamic acid at position 229 in the ketoamine oxidase derived from *Pyrenochaeta* sp., glutamic acid at position 231 in the ketoamine oxidase derived from *Arthrinium* sp., glutamic acid at position 229 in the ketoamine oxidase derived from *Curvularia clavata*, glutamic acid at position 231 in the ketoamine oxidase derived from *Neocosmospora vasinfecta*, glutamic acid at position 231 in the fructosyl amino acid oxidase derived from *Cryptococcus neoformans*, histidine at position 227 in the fructosyl peptide oxidase derived from *Phaeosphaeria nodorum*, glutamic acid at position 231 in the fructosyl amino acid oxidase derived from *Aspergillus nidulans*, glutamine at position 229 in the fructosyl amino acid oxidase derived from *Ulocladium* sp., and glutamic acid at position 231 in the fructosyl amino acid oxidase derived from *Penicillium crysogenum*.

"The position corresponding to aspartic acid at position 232 in the amino acid sequence described in SEQ ID No: 1" refers to an amino acid corresponding to aspartic acid at position 232 of an amadoriase of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-2 in which amino acid sequences are aligned.

More specifically, the position corresponding to aspartic acid at position 232 in the amino acid sequence described in SEQ ID No: 1 is aspartic acid at position 232 in the amadoriase derived from *Eupenicillium terrenum*, aspartic acid at position 230 in the ketoamine oxidase derived from *Pyrenochaeta* sp., glutamic acid at position 232 in the ketoamine oxidase derived from *Arthrinium* sp., aspartic acid at position 230 in the ketoamine oxidase derived from *Curvularia clavata*, glutamic acid at position 232 in the ketoamine oxidase derived from *Neocosmospora vasinfecta*, glycine at position 232 in the fructosyl amino acid oxidase derived from *Cryptococcus neoformans*, glutamic acid at position 228 in the fructosyl peptide oxidase derived from *Phaeosphaeria nodorum*, glutamic acid at position 232 in the fructosyl amino acid oxidase derived from *Aspergillus nidulans*, aspartic acid at position 230 in the fructosyl amino acid oxidase derived from *Ulocladium* sp., and aspartic acid at position 232 in the fructosyl amino acid oxidase derived from *Penicillium crysogenum*.

"The position corresponding to glutamic acid at position 249 in the amino acid sequence described in SEQ ID No: 1" refers to an amino acid corresponding to glutamic acid at position 249 of an amadoriase of SEQ ID No: 1, when the identified amino acid sequence of an amadoriase is compared with the amino acid sequence of the amadoriase derived from the genus *Coniochaeta* and shown in SEQ ID No: 1. This can be also specified by the aforementioned method with reference to FIG. 1-2 in which amino acid sequences are aligned.

More specifically, the position corresponding to glutamic acid at position 249 in the amino acid sequence described in SEQ ID No: 1 is lysine at position 249 in the amadoriase derived from *Eupenicillium terrenum*, lysine of position 247 in the ketoamine oxidase derived from *Pyrenochaeta* sp., histidine at position 249 in the ketoamine oxidase derived from *Arthrinium* sp., glutamic acid at position 247 in the ketoamine oxidase derived from *Curvularia clavata*, glutamic acid at position 249 in the ketoamine oxidase derived from *Neocosmospora vasinfecta*, glutamic acid at position 249 in the fructosyl amino acid oxidase derived from *Cryptococcus neoformans*, glutamic acid at position 245 in the fructosyl peptide oxidase derived from *Phaeosphaeria nodorum*, alanine at position 249 in the fructosyl amino acid oxidase derived from *Aspergillus nidulans*, serine at position 247 in the fructosyl amino acid oxidase derived from *Ulocladium* sp., and glutamine at position 249 in the fructosyl amino acid oxidase derived from *Penicillium crysogenum*.

(Production of the Amadoriase of the Present Invention)

In order to use a strain having the ability to produce an amadoriase having excellent resistance to detergents obtained as described above and produce said amadoriase, the strain may be cultured by a conventional solid culture method, although liquid culture is preferable where possible.

Examples of media to culture the aforementioned strains include media prepared by adding one or more inorganic salts, such as sodium chloride, monopotassium phosphate, dipotassium phosphate, magnesium sulfate, magnesium chloride, ferric chloride, ferric sulfate, and manganese sulfate, to one or more nitrogen sources, such as a yeast extract, tryptone, peptone, a meat extract, a corn steep liquor, and a leaching solution of soybean or wheat bran, and further adding saccharine materials, vitamins, and the like thereto, where necessary.

Incidentally, it is appropriate to adjust the initial pH of the media as from 7 to 9.

Further, culture can be performed under any condition and, for example, culture can be performed at 20° C. to 42° C., and more preferably at about 30° C. for 4 to 24 hours, and further preferably at about 30° C. for 8 to 16 hours, by, for example, aeration spinner submerged culture, shake culture, or stationary culture.

Following the completion of culture, amadoriases may be collected from the culture products with conventional enzyme collecting means. For example, a strain may be subjected to ultrasonic disintegration treatment or grinding treatment by a conventional method, the enzyme may be extracted using a lytic enzyme such as lysozyme, or bacteriolysis may be performed via shaking or still standing in the presence of toluene to excrete the enzyme from the microorganism body. The solution is filtered or centrifuged to remove solid content, and according to need, nucleic acid is removed with the aid of streptomycin sulfate, protamine sulfate, or manganese sulfate, and to this ammonium sulfate, alcohol, or acetone is added to the solution so as to fractionate the solution, and sediments are then collected to obtain the crude enzymes of the amadoriases.

The purified amadoriase enzyme preparation can be obtained from: the crude enzyme of the aforementioned amadoriase by a method appropriately selected from gel filtration methods using Sephadex, Superdex, or Ultrogel; adsorption-elution methods using ion exchange carriers; electrophoretic methods using polyacrylamide gels, etc.; adsorption-elution methods using hydroxyapatite; sedimentation methods such as sucrose density-gradient centrifugation; affinity chromatographic methods; and fractionation methods using a molecular sieve membrane, a hollow-fiber membrane, etc. Alternatively, the aforementioned methods can adequately be performed in combination. The amadoriase having improved substrate specificity of interest can thus be obtained.

(Surfactant of the Present Invention)

The surfactant of the present invention is not particularly limited so long as a method of measuring HbA1c of the present invention can be carried out in the presence of the surfactant, and a nonionic surfactant and an ionic surfactant such as a cationic surfactant, an anionic surfactant and an amphoteric surfactant, can be mentioned and particularly, a cationic surfactant and an anionic surfactant are preferable. The expression surfactant when mentioned in the present specification encompasses one or more surfactants unless otherwise indicated.

The surfactant of the present invention can be a surfactant having a critical micelle concentration (CMC) of 70 mM or lower, 50 mM or lower, 20 mM or lower, 10 mM or lower, 7 mM or lower, 6 mM or lower, 5 mM or lower, 4.5 mM or lower, 4 mM or lower, 3.5 mM or lower, 3 mM or lower, 2.5 mM or lower, 2 mM or lower, 1.5 mM or lower, 1.3 mM or lower, or 1 mM or lower. In an embodiment, the critical micelle concentration of the surfactant of the present invention can be 0.1 mM or 0.01 mM or higher, preferably 50 mM or lower, more preferably 20 mM or lower, more preferably 10 mM or lower, more preferably 7 mM or lower, more preferably 6 mM or lower, and most preferably 5 mM or lower. The critical micelle concentration refers to the critical concentration above which micelles of a surfactant are formed in a solution and below which micelles are not formed. In general, the lower the critical micelle concentration, the lower the concentration of a surfactant forming micelles and the stronger the surfactant action. A person skilled in the art can determine the critical micelle concentration of a desired surfactant by conventional methods. For example, a commercially available kit, which measures a critical micelle concentration of a surfactant based on a change in fluorescence of a fluorescent reagent interacting with the surfactant, can be used (for example, Detergent Critical Micelle Concentration (CMC) Assay Kit manufactured by PFP Inc.).

For example, the CMC of octyltrimethylammonium bromide (C8, OTAB) is about 140 mM; the CMC of decyltrimethylammonium chloride (C10) is about 65 mM; the CMC of decyltrimethylammonium bromide (C10) is about 70 mM; the CMC of dodecyltriethylammonium chloride (C12) is about 20 mM; the CMC of dodecyltriethylammonium bromide (C12, DTAB) is about 16 mM; the CMC of tetradecyltrimethylammonium chloride (C14, TTAC) is about 4.5 mM; the CMC of tetradecyltrimethylammonium bromide (C14, TTAB) is about 5 mM; the CMC of hexadecyltrimethylammonium chloride (C16, CTAC) is about 1.3 mM; the CMC of hexadecyltrimethylammonium bromide (C16) is about 1 mM; the CMC of octadecyltrimethylammonium chloride (C18, STAC) is about 0.3 mM; and the CMC of octadecyltrimethylammonium bromide (C18, STAB) is about 0.3 mM (for example, see J. PHYS. COLLIDE. CHEM., 52, 130 (1948); J. PHYS. CHEM., 66, 1839 (1962); J. AM. OIL. CHEMISTS. SOC., 30, 74 (1953); J. PHARM. SCI., 54,436 (1965); KONINKI. NED. AKAD. WETEN. PROC. SER B, 58, 97 (1955); J. PHYS. CHEM., 65, 1807 (1961); J. AM. CHEM. SOC., 65, 692 (1943); J. AM. CHEM. SOC., 69, 2095 (1947); J. COLLIDE. INTERFACE. SCI., 22, 430 (1966); and J. AM. CHEM. SOC., 70, 3803 (1948)). The numerals within parentheses indicate the number of carbon atoms of the longest substituent.

For example, the CMC of 1-dodecylpyridinium bromide (C12) is about 12 mM; the CMC of 1-dodecylpyridinium chloride (C12, 1-DPC) is about 14 mM; the CMC of 1-tetradecylpyridinium bromide (C14) is about 2.9 mM; the CMC of 1-hexadecylpyridinium chloride (C16, 1-CPC) is about 0.6 mM; the CMC of 1-hexadecylpyridinium bromide (C16, 1-CPB) is about 0.9 mM; the CMC of N-cetyl-4-methylpyridinium chloride (C16, 4Me-1-CPC) is about 1.9 mM; the CMC of 1-octadecylpyridinium bromide is about 0.6 mM; and the CMC of 1-octadecylpyridinium chloride is about 0.24 mM (see, for example, J. COLLIDE. INTERFACE. SCI., 21, 522 (1966); J. PHARM. SCI., 54, 436 (1965); TRANS. FARADAY. SOC., 62, 3244 (1966); J. AM. CHEM. SOC., 70, 3803 (1948); REV. CHIM. AC. REP. POP. ROUM., 6, 309 (1961); and J. AM. CHEM. SOC., 70, 3049 (1948)).

The CMC of benzyldodecyldimethylammonium chloride is about 2.8 mM; the CMC of benzyltetradecyldimethylammonium chloride (C14, BDTAC) is about 0.37 mM; and the CMC of benzylcetyldimethylammonium chloride (C16, BCDAC) is about 0.042 mM (see, for example, surfactant handbook, 131 (1960), J. COLLIDE. INTERFACE. SCI., 22, 430 (1966); and J. COLLIDE. SCI., 8, 385 (1953)).

Examples of the non-ionic surfactant include a polyoxyethylene alkyl ether, a sorbitan fatty acid ester, an alkyl polyglucoside, a fatty acid diethanol amide and an alkyl monoglyceryl ether.

Examples of the cationic surfactant include an alkyltrimethylammonium salt, a dialkyldimethylammonium salt, an alkylbenzyldimethyl ammonium salt, a pyridinium salt such as an alkylpyridinium salt, a phosphonium salt such as an alkylphosphonium salt, an imidazolium salt such as an alkylimidazolium salt, and an isoquinolinium salt such as an alkylisoquinolinium salt.

Examples of the cationic surfactant of the present invention include a quaternary ammonium salt (I), a pyridinium salt (11) and a phosphonium salt (III) represented by the following general formulae.

[Formula 5]

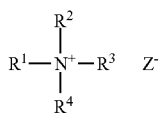

[wherein, $R^1$ to $R^4$, which may be the same or different, each represent a substituted or unsubstituted $C_1$ to $C_{20}$ alkyl, alkenyl, aryl or benzyl; and $Z^-$ represents a monovalent anion].

[Formula 6]

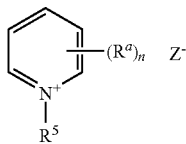

[wherein, $R^5$ represents a substituted or unsubstituted $C_1$ to $C_{20}$ alkyl; each $R^a$, which may be the same or different, represents a hydrogen atom or a substituted or unsubstituted $C_1$ to $C_{20}$ alkyl, alkenyl, aryl or benzyl; n represents an integer of 1 to 5 and $Z^-$ represents a monovalent anion].

[Formula 7]

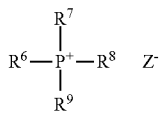

[wherein, $R^6$ to $R^9$, which may be the same or different, each represent a substituted or unsubstituted $C_1$ to $C_{20}$ alkyl, alkenyl, aryl or benzyl; and $Z^-$ represents a monovalent anion].

Examples of the quaternary ammonium salt include octyltrimethylammonium chloride (OTAC), octyltrimethylammonium bromide (OTAB), decyltrimethylammonium chloride, decyltrimethylammonium bromide (DTAB), dodecyltrimethylammonium chloride, dodecyltrimethylammonium bromide, tetradecyltrimethylammonium chloride (TTAC), tetradecyltrimethylammonium bromide (TTAB), hexadecyltrimethylammonium chloride (CTAC), hexadecyltrimethylammonium bromide, octadecyltrimethylammonium chloride, octadecyltrimethylammonium bromide (STAB), eicosyltrimethylammonium chloride, eicosyltrimethylammonium bromide, benzyldodecyldimethylammonium chloride, benzyldodecyldimethylammonium bromide (BDDAB), benzyltetradecyldimethylammonium chloride (BDTAC), benzyltetradecyldimethyl ammonium bromide, benzylcetyldimethyl ammonium chloride (BCDAC), benzylcetyldimethylammonium bromide, dioctyldimethylammonium chloride and dioctyldimethylammonium bromide.

Examples of the pyridinium salt include 1-decylpyridinium chloride, 1-decylpyridinium bromide, 1-dodecylpyridinium chloride (1-DPC), 1-dodecylpyridinium bromide, 1-tetradecylpyridinium chloride, 1-tetradecylpyridinium bromide, 1-hexadecylpyridinium chloride (1-CPC), 1-hexadecylpyridinium bromide (1-CPB), N-cetyl-2-methylpyridinium chloride, N-cetyl-3-methylpyridinium chloride, N-cetyl-4-methylpyridinium chloride (4Me-1-CPC), 1-octadecylpyridinium chloride, 1-octadecylpyridinium bromide, 1-eicosylpyridinium chloride and 1-eicosylpyridinium bromide.

Examples of the phosphonium salt include tetraethylphosphonium chloride, tetraethylphosphonium bromide, tributylmethylphosphonium chloride, tributylmethylphosphonium bromide, tributylmethylphosphonium iodide, tetrabutylphosphonium chloride, tetrabutylphosphonium bromide, tetra-n-octylphosphonium chloride, tetra-n-octylphosphonium bromide, tributyldodecylphosphonium chloride, tributyldodecylphosphonium bromide, tributylhexadecylphosphonium chloride, tributylhexadecylphosphonium bromide (TBCPB), methyltriphenylphosphonium chloride, methyltriphenylphosphonium bromide, methyltriphenylphosphonium iodide, tetraphenylphosphonium chloride and tetratetraphenylphosphonium bromide.

Anion $Z^-$ to be pair up with a cationic surfactant, can, for example, be $Cl^-$, $Br^-$ or $I^-$.

Examples of the anionic surfactant include a linear alkylbenzene sulfonate, an alkyl sulfate, an alpha-olefin sulfonate, a polyoxyethylene alkyl ether sulfate, an α-sulfo fatty acid ester salt and an alkali metal salt of a natural fatty acid. Examples of such a surfactant include sodium dodecyl sulfate (SDS).

Examples of the amphoteric surfactant include an alkyl dimethyl amine oxide and alkylcarboxybetaine.

(Kit Containing an Amadoriase and Surfactant of the Present Invention)

The present invention provides a kit for measuring glycated hemoglobin, containing an amadoriase and a surfactant. The surfactant can be a nonionic or ionic surfactant. The amadoriase and the surfactant can be contained as a mixture or discrete components. When an amadoriase and a surfactant are contained as a mixture in a kit, it is generally preferable that the surfactant is contained at a concentration at which the amadoriase is not inactivated. When the amadoriase and surfactant are contained as discrete components in the kit, a stock solution containing a surfactant at a higher concentration than the final concentration used for measurement may be used as the surfactant. This stock solution is appropriately diluted to prepare the solution for used in measurement.

The kit containing an amadoriase and a surfactant of the present invention can further contain a reagent for measuring αFVH, a protease or peptidase for cleaving αFVH and other components, i.e., a stabilizer and a buffer solution known in the art. Techniques used in kits for measuring αFVH can be appropriately used for producing a kit containing an amadoriase of the present invention and a surfactant. More specifically, the present invention provides a method for producing a kit containing an amadoriase and a surfactant comprising the step of preparing an appropriate amadoriase and surfactant. In this case, the amadoriase and surfactant can be prepared as a mixture or discrete components. When the amadoriase and surfactant are provided as discrete components in a kit, they can be mixed immediately before measurement of αFVH.

The amadoriase contained in the kit of the present invention preferably exhibits a residual activity (%) of preferably 13% or higher, more preferably 15% or higher, most preferably 19% or higher, (for example, 20% or higher, 30% or higher, 40% or higher, 50% or higher, 60% or higher, 70% or higher, 80% or higher, 90% or higher, 95% or higher or 99% or higher) 5 minutes after a surfactant solution controlled to have a final concentration is added, compared with the amadoriase to which the surfactant solution is not added. The residual activity will be described below.

The amadoriase contained in the kit of the present invention has a final concentration of 110 µg/ml or lower (for example, 100 µg/ml or lower, 70 µg/ml or lower, or 50 µg/ml or lower) per surfactant of 0.01% (w/v) preferably at the time of measurement. The surfactant contained in the kit has a final concentration at the time of measurement of 0.01% (w/v) or higher (for example, 0.02% (w/v) or higher, 0.04% (w/v) or higher, 0.05% (w/v) or higher, 0.06% (w/v) or higher, 0.07% (w/v) or higher, 0.08% (w/v) or higher, 0.09% (w/v) or higher, 0.1% (w/v) or higher, 0.15% (w/v) or higher, 0.2% (w/v) or higher, 0.25% (w/v) or higher, or 0.3% (w/v) or higher). The final concentration at the time of measurement herein refers to the concentration of the component finally diluted and used for measuring glycated hemoglobin. Accordingly, the kit may contain a stock solution having a higher concentration than the final concentration at the time of measurement.

The amadoriase contained in the kit of the present invention can be an amadoriase having the amino acid sequence as shown in SEQ ID No: 1 or SEQ ID NO: 37 or a variant prepared based on the same with improved surfactant resistance. The variant may have an amino acid sequence having an sequence identity of, for example, 70% or higher, 75% or higher, 80% or higher, 85% or higher, 90% or higher, 95% or higher, 97% or higher, or 99% or higher, with SEQ ID No: 1 or SEQ ID No: 37 or an amino acid sequence prepared by modifying or altering one or several amino acids in the amino acid sequence as shown in SEQ ID No: 1 or SEQ ID No: 37 or deleting, substituting, adding and/or inserting a single to several amino acids in the amino acid sequence.

The amadoriase contained in the kit of the present invention can be a naturally occurring amadoriase derived from the genara *Eupenicillium, Pyrenochaeta, Arthrinium, Curvularia, Neocosmospora, Cryptococcus, Phaeosphaeria, Aspergillus. Emericella, Ulocladium, Penicillium. Fusarium, Achaetomiella, Achaetomium, Thielavia, Chaetomium, Gelasinospora, Microascus, Leptosphaeria, Ophiobolus, Pleospora. Coniochaetidium, Pichia, Corynebacterium, Agrobacterium* and *Arthrobacter* or a variant thereof. Such variant may have one or more amino-acid substitutions at the position corresponding to an amino acid selected from the group consisting of asparagine at position 262, valine at position 257, glutamic acid at position 253, glutamine at position 337, glutamic acid at position 340, glutamic acid at position 133, glutamic acid at position 44, glycine at position 256, glutamic acid at position 81, aspartic acid at aspartic acid at position 129 at position 132, glutamic acid at position 231, aspartic acid at position 232 and glutamic acid at position 249 in the amino acid sequence as shown in SEQ ID NO: 1 or 3. A person skilled in the art can readily confirm whether or not an amadoriase or a variant thereof can be used in the kit of the present invention, more specifically, whether or not an amadoriase has desired surfactant resistance, by e.g., using the test method described later or the evaluation method in Example 7.

(Buffer)

To the kit or composition of the present invention, a buffer or a buffer solution having a buffer capacity within the range of pH5.0 to pH10.0, preferably pH6.0 to pH8.0 which is a range in which amadoriase is not inactivated, can appropriately be added. The term buffer as mentioned in the present specification is defined to include one or more buffers unless otherwise indicated. The term buffer solution refers to a solution having a buffer action (buffer capacity) of maintaining the pH of a solution within a constant range; whereas the term buffer (buffer agent) refers to an agent which confers buffer action to a solution. A buffer, if a weak acid is taken as an example, is composed of a weak acid and a salt thereof. In this case, the salt is referred to as a conjugate salt. For example, if a buffer is composed of a phosphoric acid and a potassium salt thereof, since a base compound is a phosphoric acid, such a buffer is sometimes referred to as a phosphate buffer in the present specification for convenience. The concentration of a buffer refers to the concentration of the base compound, which is a total of the compound alone serving as a base of the buffer and the conjugate salt form thereof. For example, the expression 100 mM of phosphate buffer means the total phosphoric-acid concentration, which is a total of the phosphoric acid and conjugate salt thereof (for example, potassium phosphate) contained in the solution at final concentration, is 100 mM.

Among buffers (buffer solutions), in particular, those which maintain the residual activity of an amadoriase in the presence of a surfactant or which alleviate reduction of residual activity, are preferable. In the present specification, such preferable buffer may be particularly referred to as a buffer having an amadoriase stabilizing effect or the buffer of the present invention. For example, HEPES does not have an amadoriase stabilizing effect on an amadoriase derived from the genus *Coniochaeta* (CFP-T7, SEQ ID No: 1), even if it is used in a concentration of 500 mM (pH 7.0). Thus, HEPES does not fall under a buffer having an amadoriase stabilizing effect of the present invention. As can be seen, not all buffers have amadoriase stabilizing effects. Thus, the buffer having the amadoriase stabilizing effect of the present invention not only maintains the pH of a solution at a constant level but also has the effect of stabilizing an amadoriase in buffering pH. The amadoriase stabilizing effect of the buffer of the present invention herein refers to an action of maintaining the residual activity of an amadoriase in the presence of a surfactant, or an action of alleviating reduction of residual activity. Such amadoriase stabilizing effect (action) can be evaluated by comparing the residual amadoriase activity of a solution which does not contain any buffer or a solution using a buffer which does not have amadoriase stabilizing effect of the present invention with the residual amadoriase activity of a solution using the buffer of the present invention, in the presence of a surfactant.

Examples of the buffer (buffer solution) which can be used in the kit (composition) of the present invention include a borate buffer containing boric acid and/or a salt thereof; a Tris-hydrochloride buffer; a phosphate buffer containing phosphoric acid and/or a salt thereof such as a potassium phosphate buffer or a sodium phosphate buffer; an organic acid buffer containing an organic acid buffer and/or a salt thereof such as a tricarboxylate buffer containing tricarboxylic acid (buffer) and/or a salt thereof, a citrate buffer containing citric acid and/or a salt thereof; a monocarboxylate buffer containing a monocarboxylic acid (buffer) and/or a salt thereof such as an acetate buffer containing an acetic acid (buffer) and/or a salt thereof. Examples of the buffer to be used in e.g., the kit of the present invention include Good's buffers including e.g., ACES (N-(2-acetamido)-2-aminoethanesulfonic acid), BES (N,N-bis(2-hydroxyethyl)-2-aminoethanesulfonic acid), Bicin (N,N-bis(2-hydroxyethyl)glycine), Bis-Tris (bis(2-hydroxyethyl)iminotris (hydroxymethyl) methane), CHES (N-cyclohexyl-2-aminoethane sulfonic acid), EPPS (4-(2-hydroxyethyl)-1-piperazine-propanesulfonic acid), HEPES (4-2-hydroxyethyl-1-piperazine-ethanesulfonic acid), HEPPSO (N-(hydroxyethyl)piperazine-N'-2-hydroxy-propanesulfonic acid), MES (2-(N-morpholino)ethanesulfonic acid), MOPS (3-(N-morpholino)propanesulfonic acid), MOPSO (2-hydroxy-3-morpholino-propanesulfonic acid), PIPES (piperazine-N,N'-bis(2-ethanesulfonic acid)), POPSO (piperazine-1,4-bis(2-hydroxypropanesulfonic acid)), TAPS (N-tris(hydroxymethyl)methyl-3-aminopropanesulfonic acid), TAPSO (3-[N-tris(hydroxymethyl)methylamino]-2-hydroxypropanesulfonic acid), TES (N-tris(hydroxymethyl)methyl-2-aminoethanesulfonic acid), Tricine (N-tris(hydroxymethyl)methylglycine) and/or salts thereof. Furthermore, a buffer containing a compound represented by the following formula (IV):

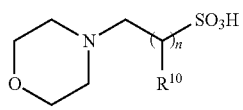

[Formula 8]

[where n may be 0, 1, 2 or 3; each $R^{10}$ independently represents H, OH, —CH$_2$OH or —COOH], and/or a salt thereof, may be mentioned. Moreover, a buffer based on a dicarboxylic acid may be mentioned, including a phthalate buffer containing phthalic acid and/or a salt thereof; a maleate buffer containing maleic acid and/or a salt thereof; a fumarate buffer containing fumaric acid and/or a salt thereof; a glutarate buffer containing glutaric acid and/or a salt thereof; a citraconate buffer containing citraconic acid and/or a salt thereof; a mesaconate buffer containing mesaconic acid and/or a salt thereof; a malonate buffer containing malonic acid and/or a salt thereof; a tartrate buffer containing tartaric acid and/or a salt thereof; a succinate buffer containing succinic acid and/or a salt thereof; an adipate buffer containing adipic acid and/or a salt thereof; and a malate buffer containing malic acid and/or a salt thereof. These, excluding HEPES and CHES, may serve as a buffer having the amadoriase stabilizing effect of the present invention. Examples of a preferable buffer having the amadoriase stabilizing effect of the present invention include, but not limited to, a phosphate buffer, an ACES buffer, a citrate buffer, a malate buffer, an acetate buffer, a maleate buffer, a citraconate buffer, a malonate buffer, a glutarate buffer, a tartrate buffer, and a buffer represented by formula (IV) such as MES buffer, MOPS buffer, and MOPSO buffer. These may be used alone or in combination of two or more. The buffer having the amadoriase stabilizing effect of the present invention may be used in combination with a substance (e.g., a buffer not having an amadoriase stabilizing effect) other than the above buffers. Examples of the salt include, but are not limited to, a sodium salt, a potassium salt, a magnesium salt, a calcium salt and an ammonium salt of a base compound.

The buffer of the present invention can be used in an appropriate concentration in the kit or composition of the present invention. In general, the amount of buffer of the present invention to be added in the kit or composition of the present invention can be calculated based on the final concentration in a measurement solution. In one embodiment, the final concentration of the buffer of the present invention in a measurement solution is the concentration at which a pH change that can occur in the measurement solution is sufficiently buffered. In another embodiment, the final concentration of the buffer of the present invention in a measurement solution is the concentration at which the residual activity of an amadoriase in a solution containing a surfactant becomes 20% or higher, preferably 40% or higher, preferably 60% or higher, and preferably 80% or higher. The final concentration of the buffer of the present invention can be, for example, 1 mM or higher, 5 mM or higher, 10 mM or higher, 20 mM or higher, for example 50 mM or higher, 1M or lower, 500 mM or lower, 400 mM or lower, 300 mM or lower, 200 mM or lower, 100 mM or lower, for example 1 mM to 1M, 5 mM to 500 mM, 10 mM to 300 mM, for example 50 mM to 100 mM. When a phosphate buffer is used as the buffer having the amadoriase stabilizing effect of the present invention, the concentration thereof can be 50 mM to 500 mM, for example, 50 mM to 300 mM and preferably 100 mM to 300 mM. When a citrate buffer, a malate buffer, maleic acid, a citraconate buffer, a malonate buffer, a glutarate buffer or a tartrate buffer is used as the buffer of the present invention, the concentration thereof can be 5 mM to 500 mM, preferably 10 mM to 200 mM, for example, 10 mM to 100 mM. When a buffer represented by formula (IV) such as MES buffer, MOPS buffer or MOPSO buffer is used as the buffer of the present invention, the concentration thereof can be 10 mM to 500 mM, for example, 100 mM to 500 mM, for example 150 mM to 300 mM. When an ACES buffer is used as the buffer of the present invention, the concentration thereof can be 200 mM to 1M, for example, 200 mM to 500 mM. As the buffer of the present invention, a plurality of buffers may be used in combination. The amount of buffer of the present invention to be used in a composition, if a stabilizer is also added to the composition, may vary depending upon the amount of stabilizer.

(Stabilizer)

To the kit or composition of the present invention, a stabilizer, which maintains the residual activity of an amadoriase or lowers a reduction of the residual activity in the presence of a surfactant, can be appropriately added. In the present specification, the stabilizer refers to a substance, which maintains the residual activity of an amadoriase or lowers a reduction of the residual activity in the presence of a surfactant. In the present specification, the expression stabilizer encompasses one or more stabilizers, unless otherwise indicated. Examples of the stabilizer to be contained in the kit or composition of the present invention include phosphoric acid, tricarboxylic acid (for example, citric acid), dicarboxylic acid (for example, malic acid, maleic acid, citraconic acid, malonic acid, glutaric acid, tartaric acid), monocarboxylic acid (for example, acetic acid), a compound represented by formula (TV) (for example, MES, MOPS, MOPSO), ammonium sulfate, salts of these and any combination thereof.

The stabilizer of the present invention can be used in an appropriate concentration in the kit or composition of the present invention. In general, the amount of stabilizer to be added to the kit or composition of the present invention is calculated based on the final concentration in the measurement solution. In one embodiment, the amount of stabilizer added is the amount at which the residual activity of an amadoriase in a solution containing a surfactant is 35% or higher, 37.5% or higher, preferably 40% or higher, 45% or higher, 50% or higher, 55% or higher, preferably 60% or higher, 65% or higher, 70% or higher, 75% or higher, preferably 80% or higher, 85% or higher, 90% or higher or 95% or higher. The stabilizer of the present invention can be added to the kit or composition such that the final concentration in the measurement solution becomes, for example, 0.1 mM to 100 mM, 0.2 mM to 100 mM, 0.5 mM to 50 mM, 1 mM to 30 mM, 2 mM to 30 mM, 5 mM to 20 mM or 10 mM to 20 mM. If a buffer is also added to the composition of the present invention, the amount of a stabilizer may vary depending on the amount of buffer. For example, to prevent pH change when a stabilizer is added, the type and amount of a buffer to be added may be appropriately selected and adjusted, or the pH of the stabilizer solution may appropriately be adjusted.

Among the buffers of the present invention, in particular, a phosphate buffer, a citrate buffer and MES buffer, when they are used in a concentration, at which the pH of the solution can be kept at a constant level, more specifically, e.g., 100 mM for a phosphate buffer, e.g., 50 mM for a citrate buffer, and e.g., 150 mM for MES buffer, an amadoriase stabilizing effect was observed. However, if the concentration of phosphoric acid and/or a potassium salt thereof, citric acid and/or a sodium salt thereof or MES and/or a sodium salt thereof to be added to the composition are further reduced while maintaining the pH of the solution within a constant range by use of HEPES having no amadoriase stabilizing effect as a pH buffer, the stabilization action of the residual activity of an amadoriase in the presence of a surfactant was observed. The stabilization action was observed even at a lower concentration than those at which phosphoric acid and/or a potassium salt thereof, citric acid and/or a sodium salt thereof and MES and/or a sodium salt thereof effectively exert a buffer action, more specifically, 5 mM for phosphoric acid, 0.5 mM for citric acid and 20 mM for MES. From this, it was confirmed that phosphoric acid and/or a potassium salt thereof, citric acid and/or a sodium salt thereof and MES and/or a sodium salt thereof have a stabilizing effect to maintain amadoriase activity apart from an amadoriase stabilizing effect as a buffer of the present invention. Such action may be referred to herein as the amadoriase stabilizing effect of the stabilizer of the present invention, for convenience, in order to distinguish this from the amadoriase stabilizing effect of the buffer of the present invention. Thus, phosphoric acid and/or a potassium salt thereof, citric acid and/or a sodium salt thereof and MES and/or a sodium salt thereof have the amadoriase stabilizing effect of the buffer of the present invention as well as the amadoriase stabilizing effect of the stabilizer of the present invention. In other words, phosphoric acid and/or a potassium salt thereof, citric acid and/or a sodium salt thereof and MES and/or a sodium salt thereof fall under not only the buffer of the present invention but also the stabilizer of the present invention.

Further, it was observed that maleic acid, citraconic acid, malonic acid, glutaric acid, tartaric acid, MOPS and MOPSO having amadoriase stabilizing effect exert an amadoriase stabilizing effect at concentrations lower than the concentration at which a buffer action is effectively exerted, such as 10 mM or 20 mM. These are compounds that can exert a buffer action at higher concentrations (e.g., 50 mM, 100 mM, 150 mM). Thus, maleic acid, citraconic acid, malonic acid, glutaric acid, tartaric acid, MOPS, MOPSO and the compound represented by formula (IV) also fall under not only the buffer of the present invention but also the stabilizer of the present invention.

When the kit or composition of the present invention comprises an amadoriase, a surfactant, a stabilizer and/or a buffer, these may be added in any order to the kit or composition. Preferably, a stabilizer and/or buffer (if they are contained) are added and then a surfactant is added to alleviate reduction of the residual activity of the amadoriase.

(Improvement of Surfactant Resistance of an Amadoriase of the Present Invention)

The amadoriase of the present invention obtained by the aforementioned means has a mutation in its amino acid sequence by e.g., genetic modification, with the result that the amadoriase has improved surfactant resistance, compared with an amadoriase prior to the modification. More specifically, the residual activity (%) of the modified amadoriase is improved 5 minutes after a particular surfactant treatment, for example, after 0.01% (w/v) hexadecyltrimethylammonium chloride (hereinafter referred to as, "CTAC") is added at 30° C., in the reaction conditions described in the activity measurement method and surfactant resistance evaluation method in the present specification, compared with the activity of an amadoriase prior to modification. The residual activity (%) herein refers to the ratio (%) of activity after surfactant treatment relative to the activity before the surfactant treatment (regarded as 100). When the concentration of a surfactant in the present specification is expressed by percentage, the percentage means % (w/v), unless indicated otherwise.

The degree of improvement of the residual activity (%) of a modified amadoriase of the present invention is not limited; however, for example, the present invention encompasses a modified amadoriase having a residual activity (%) of preferably 13% or higher, more preferably 15% or higher, most preferably 19% or higher, for example, 20% or higher, 30% or higher, 40% or higher, 50% or higher, 60% or higher, 70% or higher, 80% or higher, 90% or higher, 95% or higher or 99% or higher when it is measured before and after a mutation of the present invention is introduced and subjected to a surfactant treatment. When amadoriases before and after a mutation of the present invention is introduced are subjected to a surfactant treatment and then the numerical values of residual activity (%) are compared, a modified amadoriase having a residual activity improved by 2% or higher, preferably 9% or higher, most preferably 19% or higher, for example 20% or higher, 30% or higher, 40% or higher, 50% or higher, 60% or higher, 70% or higher, 80% or higher, 90% or higher, 95% or higher or 99% or higher, is encompassed by the present invention.

According to one embodiment, when a surfactant treatment is applied to an amadoriase before a mutation of the present invention is introduced, the amadoriase may completely lose its activity. In such a case, to evaluate improvement of the residual activity of an amadoriase (%) of the present invention to which a mutation of the present invention is introduced, an amadoriase which will not completely lose its activity even by a surfactant treatment is used and the residual activity of an amadoriase serving as a reference after a surfactant treatment may be compared with the residual activity of an amadoriase having a mutation introduced therein after the surfactant treatment.

In situations, it may be difficult to evaluate the absolute surfactant resistance of variants merely based on whether numerical values of the residual activity (%) and residual activity ratio are large or small, since relative evaluation results may differ depending on not only temperature conditions during measurement but also the degree of surfactant resistance of an amadoriase before introduction of a mutation. However, it is possible to absolutely evaluate the surfactant resistance of variants by following the conditions of Examples of the present invention. Further, in order to readily select the amadoriase of the present invention, by selecting surfactant treatment conditions in which the residual activity of an amadoriase (%) before introduction of a mutation is calculated to be sufficiently low, in general, the degree of improvement of the residual activity (%) and the residual activity ratio tend to be calculated to be high.

For example, when the amadoriase of the present invention produced by *Escherichia coli* JM109 (pKK223-3-CFP-T7/253K) strain encompassed by the present invention is mixed with 0.01% CTAC and subjected to a treatment at 30° C. for 5 minutes, then the residual activity of amadoriase, CFP-T7, before introduction of the mutation of the present invention is 69.9%; whereas, the residual activity thereof after introduction of the mutation of the present invention is higher than 72%. When the amadoriase of the present invention produced by *Escherichia coli* JM109 JM109 (pKK223-3-CFP-D7) strain is mixed with 0.04% CTAC and subjected to a treatment at 30° C. for 5 minutes, then the residual activity of amadoriase, CFP-D, before introduction of the mutation of the present invention is 12.7%; whereas, the residual activity thereof after introduction of the mutation of the present invention is higher than 15%. Likewise, an amadoriase improved in surfactant resistance is significantly improved in storage property in e.g., enzyme-containing products, also, improves protease degradation efficiency of HbA1c, and increases measurement sensitivity. Because of this, the amadoriase is stable when a strong surfactant is used and thus very useful from the perspective of the industry.

(Method of Measuring Activity of Amadoriase)

The activity of an amadoriase can be measured by various methods. An example of the method of measuring the activity of an amadoriase as used herein is described below.

(Method of Measuring Activity of Amadoriase)

Examples of major methods for measuring the enzyme activity of the amadoriase of the present invention include a method of measuring the amount of hydrogen peroxide generated by enzyme reactions and a method of measuring the amount of oxygen consumed in enzyme reactions. An example of the method of measuring the amount of hydrogen peroxide is described below.

Hereinafter, when the activity of an amadoriase is measured in the present invention, fructosyl valine is used as a substrate, unless otherwise specified. The titer of enzyme is defined such that, when using fructosyl valine as a substrate in measurement, the amount of enzyme which generates 1 μmol of hydrogen peroxide per minute is (defined as) 1 U. A glycated amino acid such as fructosyl valine and a glycated peptide such as fructosyl-valyl histidine can be synthesized and purified based on the method of Sakagami et al. (see, JP Patent Publication (Kokai) No. 2001-95598).

A. Preparation of Reagent (1) Reagent 1: POD-4-AA Solution

Peroxidase (4.0 kU, manufactured by Kikkoman Corporation) and 100 mg of 4-aminoantipyrine (manufactured by Tokyo Kasei Kogyo Co., Ltd.) are dissolved in 0.1 M potassium phosphate buffer (pH7.0) and the volume of the solution is fixed at 1 L.

(2) Reagent 2: TOOS Solution

TOOS (500 mg, sodium N-ethyl-N-(2-hydroxy-3-sulfopropyl)-m-toluidine, manufactured by Dojindo Laboratories) was dissolved in ion-exchanged water and the volume of the solution is fixed at 100 ml.

(3) Reagent 3: Substrate Solution (150 mM; Final Concentration: 5 mM)

Fructosyl valine (417 mg) is dissolved in ion-exchanged water and the volume of the solution is fixed at 10 ml.

B. Measurement Method

Reagent 1 (2.7 ml), reagent 2 (100 μl) and reagent 3 (100 μl) were mixed and preheated at 37° C. for 5 minutes. Then, to the mixture, an enzyme solution (100 μl) was added and thoroughly mixed. Thereafter, the absorbance of the mixture at 555 nm is measured by a spectrophotometer (U-3010, manufactured by Hitachi High-Technologies). Measurement is performed at 555 nm from one minute to three minutes and an absorbance change per minute is specified as the measurement value. A control solution is prepared in the same manner as above except that ion-exchanged water (100 μl) is used in place of reagent 3 (100 μl). The number of micromoles of hydrogen peroxide generated per minute at 37° C. is specified as the activity unit (U) of the enzyme solution and calculated in accordance with the following equation:

$$\text{Activity (U/ml)} = \{(\Delta As - \Delta A0) \times 3.0 \times df\} \div (39.2 \times 0.5 \times 0.1)$$

$\Delta As$: change in absorbance of reaction solution per minute $\Delta_0$: change in absorbance of control solution per minute 39.2: millimole absorbance index ($mM^{-1} \cdot cm^{-1}$) of quinoneimine dye generated by reaction 0.5: number of moles of quinoneimine dye generated by 1 mol hydrogen peroxide df: dilution factor (Method for Measuring Surfactant Resistance)

An amadoriase crude enzyme solution or an amadoriase purified sample is diluted with a 30 mM MES/21 mM Tris buffer solution (pH6.5) so as to have a concentration of about 1.0 U/ml. To this, CTAC (for example, manufactured by Tokyo Kasei Kogyo Co., Ltd.) is added so as to obtain a final concentration 0.01% (w/v) or 0.04%. The resultant mixture is heated at 30° C. for 5 minutes. After heating, the mixture is diluted double with a 10 mM phosphate buffer (pH7.0) containing 0.15% BSA to prepare a sample. The enzyme activities of the sample before and after a surfactant treatment are measured by the method described in Section B above. The ratio of activity of the sample after the surfactant treatment relative to the activity of the sample before the surfactant treatment (regarded as 100), i.e., the residual activity (%), is obtained. In this manner, surfactant resistance is evaluated.

(Method for Evaluating Buffer)

In the above surfactant resistance measuring method, the residual activity of an amadoriase is measured by using various buffers in place of a 30 mM MES/21 mM Tris buffer solution. In this manner, the contribution of the buffer to the amadoriase residual activity can be evaluated. For example, in place of the 30 mM MES/21 mM Tris buffer solution (pH 6.5), e.g., a phosphate buffer solution (pH 7.0), a citrate buffer solution (pH 6.0), a HEPES buffer solution (pH 7.0) or an ACES buffer solution (pH 7.0) can be used. Other conditions and procedure can be the same as in the above surfactant resistance measuring method.

(Method for Evaluating Stabilizer)

In the above surfactant resistance measuring method, various stabilizers are added and the residual activity of an amadoriase is measured in order to evaluate the effect of the stabilizers. In order to evaluate the amadoriase stabilizing effect independently of contribution of the compound (due to the buffer action) to the amadoriase residual activity when the stabilizers to be evaluated are compounds also having a buffer action, a buffer having no amadoriase stabilizing effect is used at a concentration sufficient to provide a buffer capacity to a solution (for example, HEPES (pH 7.0) is used at 500 mM); while at the same time, stabilizers can be used at low concentrations insufficient to provide buffer capacity to the solution. The concentration sufficient to provide a buffer capacity to a solution refers to the concentration at which pH is maintained within a predetermined range (for example pH5 to 10, pH6 to 8) without having pH change due to other reagents added to the solution. A concentration insufficient to provide a buffer capacity to a solution refers to the concentration at which pH changes by addition of other reagents to the solution and pH falls outside a particular range. These concentrations vary depending upon the type and amount of other reagents to be added to a solution; however, a person skilled in the art can appropriately determine the concentration by conventional methods. Other conditions and procedure can be the same as in the above surfactant resistance measuring method.

(Action by Combined Use)

In order to evaluate the amadoriase stabilization action of a combined use of the buffer of the present invention and the stabilizer of the present invention, the stabilizer and buffer can appropriately be added while adjusting the concentrations thereof to a solution containing the amadoriase of the present invention and a surfactant, and then the residual activity of the amadoriase can be measured. Other conditions and procedure can be the same as in the above surfactant resistance measuring method.

The present invention will be more specifically described below with reference to Examples. However, these Examples are not intended in any way to limit the technical scope of the present invention.

EXAMPLE 1

[Mutation(s) for Improved Surfactant Resistance]
(1) Preparation of Recombinant Plasmid pKK223-3-CFP-T7 DNA

*Escherichia coli* strain JM109 (pKK223-3-CFP-T7) having a recombinant plasmid containing CFP-T7 gene (SEQ ID NO: 2) (see International Publication No. WO 2007/125779) was inoculated in 2.5 ml of LB-amp medium [1% (w/v) bactotrypton, 0.5% (w/v) peptone, 0.5% (w/v) NaCl, and 50 µg/ml ampicillin] and subjected to shake culture at 37° C. for 20 hours and a culture product was obtained.

The culture product was centrifuged at 7,000 rpm for 5 minutes to collect strains. Then the recombinant plasmid pKK223-3-CFP-T7 was extracted and purified therefrom using the QIAGEN tip-100 kit (QIAGEN), and 2.5 µg DNA of the recombinant plasmid pKK223-3-CFP-T7 was obtained.

(2) Site-directed Modification Operation of DNA of Recombinant Plasmid pKK223-3-CFP-T7

PCR was carried out under conditions described below using obtained DNA of the recombinant plasmid pKK223-3-CFP-T7 as the template, synthetic oligonucleotides of SEQ ID NOs: 5 and 6, and KOD-Plus- (Toyobo Co., Ltd.).

That is, 5 µl of 10×KOD-Plus- buffer, 5 µl of a dNTPs mixture in which each dNTP was adjusted at 2 mM, 2 µl of a 25 mM $MgSO_4$ solution, 50 ng of DNA of pKK223-3-CFP-T7 as a template. 15 µmol each of the synthetic oligonucleotides, and 1 unit of KOD-Plus were mixed, and sterilized water was added thereto in order to bring the total amount of the solution to 50 µl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 6 minutes was then repeated 30 times.

A portion of the reaction solution was electrophoresed on 1.0% agarose gel, and the specific amplification of about 6,000 bp DNA was confirmed. The DNA thus obtained was treated with a restriction enzyme, DpnI (from New England Biolabs Co., Ltd.); after cleaving the remaining template DNA, *Escherichia coli* JN109 was transformed therewith; and the resultant transformants were spread on LB-amp agar medium. The grown colonies were inoculated into LB-amp medium and subjected to shake culture, and plasmid DNA was isolated in the same manner as in (1) above. The nucleotide sequence of DNA encoding an amadoriase in the plasmid was determined using a multi-capillary DNA analysis system, Applied Biosystems 3130×I Genetic Analyzer (from Life Technologies Co., Ltd.); as a result, a recombinant plasmid encoding a modified amadoriase in which asparagine at position 262 in the amino acid sequence described in SEQ ID NO: 1 was substituted with histidine (pKK223-3-CFP-T7-262H) was obtained.

Subsequently, to substitute valine at position 257 in the amino acid sequence described in SEQ ID NO: 1 with cysteine, PCR reaction was carried out under the same conditions as those described above using a recombinant plasmid, pKK223-3-CFP-T7 DNA, as a template, the synthetic oligonucleotides of SEQ ID NOS: 7 and 8, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which valine at position 257 in the amino acid sequence described in SEQ ID NO: 1 was substituted with cysteine (pKK223-3-CFP-T7-257C) was obtained.

Subsequently, to substitute valine at position 257 in the amino acid sequence described in SEQ ID NO: 1 with serine, PCR reaction was carried out under the same conditions as those described above using a recombinant plasmid pKK223-3-CFP-T7 DNA as a template, the synthetic oligonucleotides of SEQ ID NOS: 8 and 9, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which valine at position 257 in the amino acid sequence described in SEQ ID NO: 1 was substituted with serine (pKK223-3-CFP-T7-257S) was obtained.

Subsequently, to substitute valine at position 257 in the amino acid sequence described in SEQ ID NO: 1 with threonine, PCR reaction was carried out under the same conditions as those described above using a recombinant plasmid pKK223-3-CFP-T7 DNA as a template, synthetic oligonucleotides of SEQ ID NOS: 8 and 10, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which valine at position 257 in the amino acid sequence described in SEQ ID NO: 1 was substituted with threonine (pKK223-3-CFP-T7-257T) was obtained.

Subsequently, to substitute glutamic acid at position 253 in the amino acid sequence described in SEQ ID NO: 1 with lysine, PCR reaction was carried out under the same conditions as those described above using a recombinant plasmid pKK223-3-CFP-T7 DNA as a template, the synthetic oligonucleotides of SEQ ID NOS: 11 and 12, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glutamic acid at position 253 in the amino acid sequence described in SEQ ID NO: 1 was substituted with lysine (pKK223-3-CFP-T7-253K) was obtained.

Subsequently, to substitute glutamic acid at position 253 in the amino acid sequence described in SEQ ID NO: 1 with arginine, PCR reaction was carried out under the same conditions as those described above using a recombinant plasmid pKK223-3-CFP-T7 DNA as a template, the synthetic oligonucleotides of SEQ ID NOS: 12 and 13, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glutamic acid at position 253 in the amino acid sequence described in SEQ ID NO: 1 was substituted with arginine (pKK223-3-CFP-T7-253R) was obtained.

Subsequently, to substitute glutamine at position 337 in the amino acid sequence described in SEQ ID NO: 1 with lysine, PCR reaction was carried out under the same conditions as those described above using a recombinant plasmid pKK223-3-CFP-T7-H1 DNA as a template, the oligonucleotides of SEQ ID NOS: 14 and 15, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glutamine at position 337 in the amino acid sequence described in SEQ ID NO: 1 was substituted with lysine (pKK223-3-CFP-T7-337K) was obtained.

Subsequently, to substitute glutamic acid at position 340 in the amino acid sequence described in SEQ ID NO: 1 with proline, PCR reaction was carried out under the same conditions as those described above using a recombinant plasmid pKK223-3-CFP-T7 DNA as a template, the oligonucleotides of SEQ ID NOS: 16 and 17, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glutamic acid at position 340 in the amino acid sequence described in SEQ ID NO: 1 was substituted with proline (pKK223-3-CFP-T7-340P) was obtained.

Subsequently, to substitute glutamic acid at position 133 in the amino acid sequence described in SEQ ID NO: 1 with alanine, PCR reaction was carried out under the same conditions as those described above using a recombinant plasmid pKK223-3-CFP-T7 DNA as a template, the synthetic oligonucleotides of SEQ ID NOS: 18 and 19, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glutamic acid at position 133 in the amino acid sequence described in SEQ ID NO: 1 was substituted with alanine (pKK223-3-CFP-T7-133A) was obtained.

Subsequently, to substitute glutamic acid at position 133 in the amino acid sequence described in SEQ ID NO: 1 with methionine, PCR reaction was carried out under the same conditions as those described above using a recombinant plasmid pKK223-3-CFP-T7 DNA as a template, the synthetic oligonucleotides of SEQ ID NOS: 19 and 20, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glutamic acid at position 133 in the amino acid sequence described in SEQ ID NO: 1 was substituted with methionine (pKK223-3-CFP-T7-133M) was obtained.

Subsequently, to substitute glutamic acid at position 133 in the amino acid sequence described in SEQ ID NO: 1 with lysine, PCR reaction was carried out under the same conditions as those described above using a recombinant plasmid pKK223-3-CFP-T7-H1 DNA as a template, the synthetic oligonucleotides of SEQ ID NOS: 19 and 21, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glutamic acid at position 133 in the amino acid sequence described in SEQ ID NO: 1 was substituted with lysine (pKK223-3-CFP-T7-133K) was obtained.

Subsequently, to substitute glutamic acid at position 44 in the amino acid sequence described in SEQ ID NO: 1 with proline, PCR reaction was carried out under the same conditions as those described above using a recombinant plasmid pKK223-3-CFP-T7 DNA as a template, the synthetic oligonucleotides of SEQ ID NOS: 22 and 23, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glutamic acid at position 44 in the amino acid sequence described in SEQ ID NO: 1 was substituted with proline (pKK223-3-CFP-T7-44P) was obtained.

Subsequently, to substitute glycine at position 256 in the amino acid sequence described in SEQ ID NO: 1 with lysine, PCR reaction was carried out under the same conditions as those described above using a recombinant plasmid pKK223-3-CFP-T7 DNA as a template, the synthetic oligonucleotides of SEQ ID NOS: 8 and 24, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glycine at position 256 in the amino acid sequence described in SEQ ID NO: 1 was substituted with lysine (pKK223-3-CFP-T7-256K) was obtained.

Subsequently, to substitute glycine at position 256 in the amino acid sequence described in SEQ ID NO: 1 with arginine, PCR reaction was carried out under the same conditions as those described above using a recombinant plasmid pKK223-3-CFP-17 DNA as a template, the synthetic oligonucleotides of SEQ ID NOS: 8 and 25, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glycine at position 256 in the amino acid sequence described in SEQ ID NO: 1 was substituted with arginine (pKK223-3-CFP-17-256R) was obtained.

Subsequently, to substitute glutamic acid at position 81 in the amino acid sequence described in SEQ ID NO: 1 with lysine, PCR reaction was carried out under the same conditions as those described above using a recombinant plasmid pKK223-3-CFP-T7 DNA as a template, the synthetic oligonucleotides of SEQ ID NOS: 26 and 27, and KOD-Plus- (from Toyobo Co., Ltd.) and the transformation of *Escherichia coli* JM109 and the determination of the nucleotide sequence of DNA encoding an amadoriase in the plasmid DNA carried on grown colonies were performed. As a result, a recombinant plasmid encoding a modified amadoriase in which glutamic acid at position 81 in the amino acid sequence described in SEQ ID NO: 1 was substituted with lysine (pKK223-3-CFP-T7-81K) was obtained.

Subsequently, to substitute aspartic acid at position 129 in the amino acid sequence described in SEQ ID NO: 1 with lysine, PCR reaction was carried out under the same conditions as those described above using a recombinant plasmid pKK223-3-CFP-T7 DNA as a template, the synthetic oligonucleotides of SEQ ID NOS: 46 and 47, and KOD-Plus- (from Toyobo Co., Ltd.) and the transformation of Escherichia coli JM109 and the determination of the nucleotide sequence of DNA encoding an amadoriase in the plasmid DNA carried on grown colonies were performed. As a result, a recombinant plasmid encoding a modified amadoriase in which aspartic acid at position 129 in the amino acid sequence described in SEQ ID NO: 1 was substituted with lysine (pKK223-3-CFP-T7-129K) was obtained.

Subsequently, to substitute aspartic acid at position 132 in the amino acid sequence described in SEQ ID NO: 1 with lysine, PCR reaction was carried out under the same conditions as those described above using a recombinant plasmid pKK223-3-CFP-T7 DNA as a template, the synthetic oligonucleotides of SEQ ID NOS: 19 and 48, and KOD-Plus- (from Toyobo Co., Ltd.) and the transformation of Escherichia coli JM109 and the determination of the nucleotide sequence of DNA encoding an amadoriase in the plasmid DNA carried on grown colonies were performed. As a result, a recombinant plasmid encoding a modified amadoriase in which aspartic acid at position 132 in the amino acid sequence described in SEQ ID NO: 1 was substituted with lysine (pKK223-3-CFP-T7-132K) was obtained.

Subsequently, to substitute glutamic acid at position 231 in the amino acid sequence described in SEQ ID NO: 1 with lysine, PCR reaction was carried out under the same conditions as those described above using a recombinant plasmid pKK223-3-CFP-T7 DNA as a template, the synthetic oligonucleotides of SEQ ID NOS: 49 and 50, and KOD-Plus- (from Toyobo Co., Ltd.) and the transformation of Escherichia coli JM109 and the determination of the nucleotide sequence of DNA encoding the asparagine in the plasmid DNA carried on grown colonies were performed. As a result, a recombinant plasmid encoding a modified amadoriase in which glutamic acid at position 231 in the amino acid sequence described in SEQ ID NO: 1 was substituted with lysine (pKK223-3-CFP-T7-231K) was obtained.

Subsequently, to substitute aspartic acid at position 232 in the amino acid sequence described in SEQ ID NO: 1 with lysine, PCR reaction was carried out under the same conditions as those described above using a recombinant plasmid pKK223-3-CFP-T7 DNA as a template, the synthetic oligonucleotides of SEQ ID NOS: 50 and 51, and KOD-Plus- (from Toyobo Co., Ltd.) and the transformation of Escherichia coli JM109 and the determination of the nucleotide sequence of DNA encoding an amadoriase in the plasmid DNA carried on grown colonies were performed. As a result, a recombinant plasmid encoding a modified amadoriase in which aspartic acid at position 232 in the amino acid sequence described in SEQ ID NO: 1 was substituted with lysine (pKK223-3-CFP-T7-232K) was obtained.

Subsequently, to substitute glutamic acid at position 249 in the amino acid sequence described in SEQ ID NO: 1 with lysine, PCR reaction was carried out under the same conditions as those described above using a recombinant plasmid pKK223-3-CFP-T7 DNA as a template, the synthetic oligonucleotides of SEQ ID NOS: 52 and 53, and KOD-Plus- (from Toyobo Co., Ltd.) and the transformation of Escherichia coli JM109 and the determination of the nucleotide sequence of DNA encoding the amadoriase in the plasmid DNA carried on grown colonies were performed. As a result, a recombinant plasmid encoding a modified amadoriase in which glutamic acid at position 249 in the amino acid sequence described in SEQ ID NO: 1 was substituted with lysine (pKK223-3-CFP-T7-249K) was obtained.

(3) Production of Various Modified Amadoriase

Escherichia coli strain JM109 holding each of the above recombinant plasmids obtained by the above procedures was cultured at 30° C. for 16 hours in 3 ml of LB-amp medium containing 0.1 mM IPTG. Then, the bacterial bodies of each strain were washed with a 0.01 M phosphate buffer solution (pH 7.0), ultrasonically disintegrated, and centrifuged at 15,000 rpm for 10 minutes, and 1.5 ml of each crude enzyme solution was prepared.

(4) Evaluation of Surfactant Resistance of Various Modified Amadoriase

Using each crude enzyme solution thus prepared as a sample, the final concentration of CTAC was set at 0.01% to evaluate the surfactant resistance of each of the modified amadoriases according to the above measurement method for surfactant resistance. The results are shown in Table 1-1. In this respect, it was confirmed that when the warmed sample was again measured for activity 30 minutes after 2-fold dilution in a BSA solution, there was no change in the activity value. In Table 1-1, CFP-T7 indicates an amadoriase derived from Escherichia coli strain JM109 (pKK223-3-CFP-T7). Since CFP-T7 as an amadoriase derived from Escherichia coli strain JM109 (pKK223-3-CFP-T7) was used as the enzyme to which mutations were introduced, the mutation points already introduced into CFP-T7 are not included in the description of the "Amino Acid Mutation" described in the table.

TABLE 1-1

| Plasmid | Enzyme | Amino Acid Mutation | Residual Activity (%) |
|---|---|---|---|
| pKK223-3-CFP-T7 | CFP-T7 | None | 69.9 |
| pKK223-3-CFP-T7/262H | CFP-T7/262H | N262H | 94.6 |
| pKK223-3-CFP-T7/257C | CFP-T7/257C | V257C | 72.8 |
| pKK223-3-CFP-T7/257S | CFP-T7/257S | V257S | 84.9 |
| pKK223-3-CFP-T7/257T | CFP-T7/257T | V257T | 86.4 |
| pKK223-3-CFP-T7/253K | CFP-T7/253K | E253K | 99.2 |
| pKK223-3-CFP-T7/253R | CFP-T7/253R | E253R | 94.5 |
| pKK223-3-CFP-T7/337K | CFP-T7/337K | Q337K | 89.7 |
| pKK223-3-CFP-T7/340P | CFP-T7/340P | E340P | 93.6 |
| pKK223-3-CFP-T7/133A | CFP-T7/133A | E133A | 79.0 |
| pKK223-3-CFP-T7/133M | CFP-T7/133M | E133M | 72.7 |
| pKK223-3-CFP-T7/133K | CFP-T7/133K | E133K | 97.5 |
| pKK223-3-CFP-T7/44P | CFP-T7/44P | E44P | 76.0 |
| pKK223-3-CFP-T7/256K | CFP-T7/256K | G256K | 85.2 |
| pKK223-3-CFP-T7/256R | CFP-T7/256R | G256R | 96.6 |
| pKK223-3-CFP-T7/81K | CFP-T7/81K | E81K | 72.2 |
| pKK223-3-CFP-T7/129K | CFP-T7/129K | D129K | 97.1 |
| pKK223-3-CFP-T7/132K | CFP-T7/132K | D132K | 97.1 |
| pKK223-3-CFP-T7/231K | CFP-T7/231K | E231K | 96.6 |
| pKK223-3-CFP-T7/232K | CFP-T7/232K | D232K | 96.6 |
| pKK223-3-CFP-T7/249K | CFP-T7/249K | E249K | 100 |

As shown in Table 1-1, the residual activity of CFP-T7 was 69.9% under the conditions of this Example. In contrast, the residual activity was enhanced to 72% or more (79% or more in notable instances and 89% or more in more notable instances) in the 15 variants obtained by the introduction of site-specific mutation, i.e., amadoriases in each of which asparagine at position 262 in CFP-T7 is mutated to histidine, valine at position 257 to cysteine, serine, or threonine, glutamic acid at position 253 to lysine or arginine, glutamine at position 337 to lysine, glutamic acid at position 340 to proline, glutamic acid at position 44 to proline, glutamic acid at position 133 to alanine, methionine, or lysine, glycine at position 256 to lysine or arginine, glutamic acid at position 81 to lysine, aspartic acid at position 129 to lysine, aspartic acid at position 132 to lysine, glutamic acid at position 231 to lysine, aspartic acid at position 232 to lysine, or glutamic acid at position 249 to lysine. Thus, these mutation points are each confirmed to be a mutation point for enhancing the surfactant resistance of an amadoriase.

The substitution of the amino acid at each of positions 253 and 256 in CFP-T7 with each of basic amino acid residues lysine and arginine was observed to enhance surfactant resistance. Thus, it is believed that the substitution of the amino acid at each of positions 81, 129, 132, 133, 231, 232, 249, and 337 with arginine which is a basic amino acid residue will enhance surfactant resistance, as is the case with lysine.

(5) CcFX Derived from *Curvularia clavata*

SEQ ID NO: 37 is the amino acid sequence of a ketoamine oxidase derived from *Curvularia clavata* (hereinafter referred to as CcFX) (International Publication No. WO 2004/104203). A gene (SEQ ID NO: 55) encoding the amino acid sequence of SEQ ID NO: 37 was obtained by totally synthesizing cDNA by PCR of a gene fragment as a conventional method (the stop codon TAA is contained). At this time, an EcoRI site and a HindIII site were added to the 5'-end and the 3'-end of SEQ ID NO: 55, respectively. The full-length amino acid sequence deduced based on the cloned gene sequence was confirmed to be consistent with the sequence of CcFX in FIG. 1. Subsequently, to express the gene of SEQ ID NO: 55 obtained in *Escherichia coli*, the following procedures were performed. The gene totally synthesized above was first treated with two restriction enzymes for the EcoRI site and the HindIII site (from Takara Bio Inc.) and inserted into the EcoRI-HindIII site of the pKK-223-3 vector (from GE Healthcare Co., Ltd.) to provide a recombinant plasmid, pKK223-3-CcFX. This plasmid was transformed into *Escherichia coli* strain JM109 under the same conditions as those described above to provide *Escherichia coli* strain JM109 (pKK223-3-CcFX).

Then, mutations for enhancing surfactant resistance were introduced into CcFX. More specifically, mutation was introduced into positions 129, 132, 133, 229, 230, 247, 251, 254, and 335 in CcFX as positions corresponding to positions 129, 132, 133, 231, 232, 249, 253, 256, and 337 in the amadoriase derived from the genus *Coniochaeta* (CFP-T7).

Using a recombinant plasmid containing CcFX gene (SEQ ID NO: 55) as a starting plasmid, various variants were produced as in the procedures described in (1) and (2) above in *Escherichia coli* strain JM109 (pKK223-3-CcFX) having the plasmid. The sequences of primers used for the mutation introduction are as shown in SEQ ID NOS: 56 to 74. Then, modified amadoriases were produced by the procedure described in (3) above. Subsequently, the surfactant resistance of the modified amadoriases was evaluated according to the measurement method for surfactant resistance described in (4) although under surfactant treatment conditions in which the amadoriases were each diluted in a 20 mM potassium phosphate buffer solution (pH 7.0) and mixed with 0.01% CTAC. The results are shown in Table 1-2. In this respect, it was confirmed that when the warmed sample was again measured for activity 30 minutes after 2-fold dilution in a BSA solution, there was no change in the activity value.

TABLE 1-2

| Plasmid | Enzyme | Amino Acid Mutation | SEQ ID NO of Oligonucleotide Used | Residual Activity (%) |
|---|---|---|---|---|
| pKK223-3-CcFX | CcFX | None | None | 27.4 |
| pKK223-3-CcFX/129K | CcFX/129K | D129K | 56.57 | 37.6 |
| pKK223-3-CcFX/132K | CcFX/132K | D132K | 58.61 | 34.8 |
| pKK223-3-CcFX/133K | CcFX/133K | E133K | 59.61 | 92.4 |
| pKK223-3-CcFX/133A | CcFX/133A | E133A | 60.61 | 43.0 |
| pKK223-3-CcFX/229K | CcFX/229K | E229K | 62.64 | 56.4 |
| pKK223-3-CcFX/230K | CcFX/230K | D230K | 63.64 | 44.1 |
| pKK223-3-CcFX/247K | CcFX/247K | E247K | 65.66 | 88.0 |
| pKK223-3-CcFX/251K | CcFX/251K | E251K | 67.68 | 64.3 |
| pKK223-3-CcFX/251R | CcFX/251R | E251R | 68.69 | 41.6 |
| pKK223-3-CcFX/254K | CcFX/254K | N254K | 70.71 | 63.8 |
| pKK223-3-CcFX/335K | CcFX/335K | T335K | 72.73 | 58.3 |
| pKK223-3-CcFX/335R | CcFX/335R | T335R | 73.74 | 38.5 |

As shown in Table 1-2, the residual activity of CcFX was 27.4% under the conditions of this Example. In contrast, the residual activity was enhanced to 34% or more (56% or more in notable instances and 64% or more in more notable instances) in the 12 variant amadoriases obtained by the introduction of site-specific mutation.

As above, when the mutation confirmed to enhance surfactant resistance for CFP-T7 was introduced into the corresponding positions in CcFX, similar improvements of surfactant resistance were confirmed as described above. Thus, the effect of the introduction of these mutations is not limited to amadoriases derived from a specific species and the introduction also has the effect of improving the surfactant resistance of various amadoriases by introducing mutation at the corresponding positions.

Incidentally, the amadoriase derived from the genus *Coniochaeta* has about 80% amino acid sequence identity to the ketoamine oxidase derived from *Curvularia clavata*. Hence, amadoriases derived from other species having 80% or more amino acid sequence identity to the amadoriase derived from the genus *Coniochaeta* or ketoamine oxidase derived from *Curvularia clavata* are thought to have improved (enhanced) surfactant resistance by the introduction of mutation into positions corresponding to the above positions.

The substitution of the amino acid at each of positions 251 and 335 in CcFX with lysine or arginine was observed to enhance surfactant resistance. From these results, surfactant resistance is thought to be enhanced by the substitution of the amino acid at each of positions 81, 129, 132, 133, 229, 230, 247, 251, 254, and 335 in CcFX with lysine or arginine which are basic amino acid residues. The same applies to various other amadoriases.

The substitution of the amino acid at position 133 in CFP-T7 with alanine or methionine or the substitution of the amino acid at position 133 in CcFX with alanine was observed to enhance surfactant resistance. From these results, surfactant resistance is thought to be enhanced by the substitution of the amino acid at each of position 133 in CFP-T7 and position 133 in CcFX to alanine, methionine, valine, isoleucine, leucine, phenylalanine, tryptophan, or proline as a hydrophobic amino acid residue. The same applies to various other amadoriases.

Without wishing to be being bound by any particular theory, the mechanism by which the variant amadoriase of the present invention becomes resistant to a surfactant is thought, for example, to be as follows. That is, the substitution of an acidic amino acid in an amadoriase with a hydrophobic amino acid or a basic amino acid is considered to reduce the affinity between the amadoriase and a cationic surfactant and protect the amadoriase from the denaturing action of the surfactant. In particular, the introduction of lysine or arginine, which are basic amino acid residues, is considered to cause the basic amino acid residue to repel a cationic surfactant to further protect an amadoriase from the denaturing action of a surfactant.

These mutation points of the present invention not only are effective in single mutation, but also are expected to contribute to creating variants having practical advantages by combining with various known mutations or combining the mutations of the present invention with each other.

EXAMPLE 2

[Accumulation of Mutation for Improved Surfactant Resistance]

Based on the findings of mutations for enhancing surfactant resistance obtained in Example 1, multiple variants (a double variant, a triple variant, a quadruple variant, a quintuple variant, a sextuple variant, or a septuple variant) were tested to combine and accumulate these mutations in order to obtain an amadoriase having further increased surfactant resistance.

SEQ ID NO: 3 is the amino acid sequence of an amadoriase derived from the genus *Coniochaeta* into which a mutation for improving substrate specificity (E98A) and mutations for enhancing heat stability (F43Y, G184D, deletion of 3 carboxy-terminal amino acid residues) were introduced (hereinafter indicated with "CFP-D"), and is encoded by the gene of SEQ ID NO: 4. Mutations for enhancing surfactant resistance were accumulated using plasmid DNA in which CFP-D gene was inserted into pKK223-3 vector as a template. PCR reaction was carried out under the same conditions as those in (2) above using the synthetic oligonucleotides of SEQ ID NOS: 5, 6, 7, 16, 17, 18, 19, 23, 28, 29, 30, 31, 32, 33, 46, 47, 50, 51, 52, and 54, and KOD-Plus- (from Toyobo Co., Ltd.) and the transformation of *Escherichia coli* strain JM109 and the determination of the nucleotide sequence of DNA encoding the amadoriase in the plasmid DNA carried on grown colonies were performed.

These procedures provided pKK223-3-CFP-D1 as a variant (mutant) in which glutamic acid at position 44 was substituted with proline; pKK223-3-CFP-D2 as a double variant in which glutamic acid at position 44 was substituted with proline and glutamic acid at position 340 was substituted with proline; pKK223-3-CFP-D3 as a triple variant in which glutamic acid at position 44 was substituted with proline, asparagine at position 262 was substituted with histidine, and glutamic acid at position 340 was substituted with proline: pKK223-3-CFP-D4 as a quadruple variant in which glutamic acid at position 44 was substituted with proline, valine at position 257 was substituted with cysteine, asparagine at position 262 was substituted with histidine, and glutamic acid at position 340 was substituted with proline; pKK223-3-CFP-D4/232K as a quintuple variant in which glutamic acid at position 44 was substituted with proline, valine at position 257 was substituted with cysteine, asparagine at position 262 was substituted with histidine, glutamic acid at position 340 was substituted with proline, and asparagine at position 232 was substituted with lysine; pKK223-3-CFP-D4/249K as a quintuple variant in which glutamic acid at position 44 was substituted with proline, valine at position 257 was substituted with cysteine, asparagine at position 262 was substituted with histidine, glutamic acid at position 340 was substituted with proline, and glutamic acid at position 249 was substituted with lysine; pKK223-3-CFP-D5 as a quintuple variant in which glutamic acid at position 44 was substituted with proline, glutamic acid at position 253 was substituted with lysine, valine at position 257 was substituted with cysteine, asparagine at position 262 was substituted with histidine, and glutamic acid at position 340 was substituted with proline; pKK223-3-CFP-D5/129K as a sextuple variant in which glutamic acid at position 44 was substituted with proline, glutamic acid at position 253 was substituted with lysine, valine at position 257 was substituted with cysteine, asparagine at position 262 was substituted with histidine, glutamic acid at position 340 was substituted with proline, and aspartic acid at position 129 was substituted with lysine; a pKK223-3-CFP-D6 as a sextuple variant in which glutamic acid at position 44 was substituted with proline, glutamic acid at position 133 was substituted with alanine, glutamic acid at position 253 was substituted with lysine, valine at position 257 was substituted with cysteine, asparagine at position 262 was substituted with histidine, and glutamic acid at position 340 was substituted with proline; and pKK223-3-CFP-D7 as a septuple variant in which glutamic acid at position 44 was substituted with proline, glutamic acid at position 133 was substituted with alanine, glutamic acid at position 253 was substituted with lysine, valine at position 257 was substituted with cysteine, asparagine at position 262 was substituted with histidine, glutamine at position 337 was substituted with lysine, and glutamic acid at position 340 was substituted with proline.

Then, *Escherichia coli* strain JM109 was transformed under the same conditions as those described above and *Escherichia coli* strain JM109 (pKK223-3-CFP-D), *Escherichia coli* strain JM109 (pKK223-3-CFP-D1), *Escherichia coli* strain JM109 (pKK223-3-CFP-D2), *Escherichia coli* strain JM109 (pKK223-3-CFP-D3), *Escherichia coli* strain JM109 (pKK223-3-CFP-D4), *Escherichia coli* strain JM109 (pKK223-3-CFP-D4/232K), *Escherichia coli* strain JM109 (pKK223-3-CFP-D4/249K), *Escherichia coli* strain JM109 (pKK223-3-CFP-D5), *Escherichia coli* strain JM109 (pKK223-3-CFP-D5/129K), *Escherichia coli* strain JM109 (pKK223-3-CFP-D6), and *Escherichia coli* strain JM109 (pKK223-3-CFP-D7) were obtained.

The *Escherichia coli* strains having the ability to produce modified amadoriases obtained as described above, i.e., *Escherichia coli* strain JM109 (pKK223-3-CFP-T7), *Escherichia coli* strain JM109 (pKK223-3-CFP-D), *Escherichia coli* strain JM109 (pKK223-3-CFP-D1), *Escherichia coli* strain JM109 (pKK223-3-CFP-D2), *Escherichia coli* strain JM109 (pKK223-3-CFP-D3), *Escherichia coli* strain JM109 (pKK223-3-CFP-D4), *Escherichia coli* strain JM109 (pKK223-3-CFP-D4/232K), *Escherichia coli* strain JM109 (pKK223-3-CFP-D4/249K), *Escherichia coli* strain JM109 (pKK223-3-CFP-D5), *Escherichia coli* strain JM109 (pKK223-3-CFP-D5/129K), *Escherichia coli* strain JM109 (pKK223-3-CFP-D6), and *Escherichia coli* strain JM109 (pKK223-3-CFP-D7), were cultured by the above method to prepare 1.5 ml of a crude enzyme solution of each of the modified amadoriases. Using the resultant crude enzyme solutions as samples, the surfactant resistance of the modified amadoriases was evaluated according to the measurement method for surfactant resistance described in (4) above although under more stringent surfactant treatment conditions in which treatment was altered to be mixing with 0.04% CTAC. The results are shown in Table 2-1. In this respect, it was confirmed that when the warmed sample was again measured for activity 30 minutes after 2-fold dilution in a BSA solution, there was no change in the activity value.

was 98.1% and was significantly enhanced compared to that of CFP-T7, and there was almost no inactivation of the amadoriase due to CTAC.

TABLE 2-1

| Plasmid | Plasmid as Template | Enzyme | Amino Acid Mutation | SEQ ID NO of Oligonucleotide Used | Residual Activity (%) |
|---|---|---|---|---|---|
| pKK223-3-CFP-T7 | None | CFP-T7 | None | None | 2.27 |
| pKK223-3-CFP-D | None | CFP-D | None | None | 12.7 |
| pKK223-3-CFP-D1 | pKK223-3-CFP-D | CFP-D1 | E44P | 23.28 | 15.2 |
| pKK223-3-CFP-D2 | pKK223-3-CFP-D1 | CFP-D2 | E44P/E340P | 16.17 | 37.1 |
| pKK223-3-CFP-D3 | pKK223-3-CFP-D2 | CFP-D3 | E44P/N262H/E340P | 5.6 | 51.4 |
| pKK223-3-CFP-D4 | pKK223-3-CFP-D3 | CFP-D4 | E44P/V257C/N262H/E340P | 7.29 | 60.7 |
| pKK223-3-CFP-D4/232K | pKK223-3-CFP-D3 | CFP-D4/232K | E44P/V257C/N262H/E340P/D232K | 50.51 | 66.2 |
| pKK223-3-CFP-D4/249K | pKK223-3-CFP-D3 | CFP-D4/249K | E44P/V257C/N262H/E340P/E249K | 52.54 | 91.0 |
| pKK223-3-CFP-D5 | pKK223-3-CFP-D4 | CFP-D5 | E44P/E253K/V257C/N262H/E340P | 30.31 | 95.6 |
| pKK223-3-CFP-D5/129K | pKK223-3-CFP-D4 | CFP-D5/129K | E44P/E253K/V257C/N262H/E340P/D129K | 46.47 | 98.1 |
| pKK223-3-CFP-D6 | pKK223-3-CFP-D5 | CFP-D6 | E44P/E133A/E253K/V257C/N262H/E340P | 18.19 | 99.2 |
| pKK223-3-CFP-D7 | pKK223-3-CFP-D6 | CFP-D7 | E44P/E133A/E253K/V257C/N262H/Q337K/E340P | 32.33 | 100 |

As shown in Table 2-1, the residual activity of CFP-T7 was merely 2.27% under the conditions of this Example. It was confirmed that conventional amadoriases virtually lost almost all activity under such harsh conditions.

In contrast, all of the multiple variants prepared by the various combinations of the single mutations identified in Example 1 had significantly enhanced residual activities. In particular, the residual activity of the double variant in which glutamic acid at position 44 was substituted with proline and glutamic acid at position 340 was substituted with proline was 37.1% and was enhanced compared to that of CFP-T7. The residual activity of the triple variant in which asparagine at position 262 was substitutes by histidine in addition to the prior mutation was 51.4% and was further enhanced compared to that of CFP-T7. The residual activity of the quadruple variant in which valine at position 257 was substituted with cysteine in addition to the prior mutation was 60.7% and significantly enhanced compared to that of CFP-T7. The residual activity of the quintuple variant in which glutamic acid at position 253 was substituted with lysine in addition to the prior mutation was 95.6%; the residual activity of the sextuple variant in which glutamic acid at position 133 was substituted with alanine in addition to the prior mutation was 99.2%; the residual activity of the septuple variant in which glutamine at position 337 was substituted with lysine in addition to the prior mutation was 100% and was significantly enhanced compared to CFP-T7, and there was almost no inactivation of the amadoriase due to CTAC. The residual activity of the quintuple variant in which aspartic acid at position 232 in the quadruple variant CFP-D4 was further substituted with lysine was 66.2%; the residual activity of the quintuple variant in which glutamic acid at position 249 in the quadruple variant CFP-D4 was substituted with lysine was 91.0%; the residual activity of the sextuple variant in which aspartic acid at position 129 in the quintuple variant CFP-D5 was substituted with lysine In addition, each time mutations were accumulated into CFP-D, the surfactant resistance of the resultant further multiple variant was incrementally enhanced, demonstrating that the mutation points of the present invention identified in Example 1 could appropriately be combined to produce an amadoriase having further excellent surfactant resistance.

Next, mutations for enhancement of surfactant resistant were accumulated using a plasmid DNA in which CcFX gene was inserted into pKK223-3 vector as a template. The procedures were carried out as described above except for the point that the CcFX gene was used instead of the CFP-D gene. PCR reaction was carried out under the same conditions as those in (2) above using synthetic oligonucleotides (SEQ ID NOS: 72 and 73) and KOD-Plus- (from Toyobo Co., Ltd.) and the transformation of Escherichia coli strain JM109 and the determination of the nucleotide sequence of DNA encoding the amadoriase in the plasmid DNA carried on grown colonies were performed.

These procedures provided pKK223-3-CcFX/132K/335K as a variant in which aspartic acid at position 132 was substituted with lysine and threonine at position 335 was substituted with lysine; pKK223-3-CcFX/133A/335K as a variant in which glutamic acid at position 133 was substituted with alanine and threonine at position 335 was substituted with lysine; pKK223-3-CcFX/229K/335K as a variant in which glutamic acid at position 229 was substituted with lysine and threonine at position 335 was substituted with lysine; and pKK223-3-CcFX/251K/335K as a variant in which glutamic acid at position 251 was substituted with lysine and threonine at position 335 was substituted with lysine. Then, Escherichia coli strain JM109 was transformed under the same conditions as those described above; the resultant transformant strains were cultured by the above method; and 1.5 ml each of the crude enzyme solutions of the modified amadoriases were prepared. Using the resultant crude enzyme solutions as samples, the surfactant resistance of the modified amadoriases was evaluated according to the measurement method for surfactant resistance described in (4) although under surfactant treatment conditions in which the amadoriases were each diluted in a 20 mM potassium phosphate buffer solution (pH 7.0) and mixed with 0.01% CTAC. The results are shown in Table 2-2. In this respect, it was confirmed that when the warmed sample was again measured for activity 30 minutes after 2-fold dilution in a BSA solution, there was no change in the activity value.

TABLE 2-2

| Plasmid | Plasmid as Template | Enzyme | Amino Acid Mutation | SEQ ID NO of Oligonucleotide Used | Residual Activity (%) |
|---|---|---|---|---|---|
| pKK223-3-CcFX/132K/335K | pKK223-3-CcFX/132K | CcFX/132K/335K | D132K/T335K | 72.73 | 82.8 |
| pKK223-3-CcFX/133A/335K | pKK223-3-CcFX/133A | CcFX/133A/335K | E133A/T335K | | 86.0 |
| pKK223-3-CcFX/229K/335K | pKK223-3-CcFX/229K | CcFX/229K/335K | E229K/T335K | | 65.3 |
| pKK223-3-CcFX/251K/335K | pKK223-3-CcFX/251K | CcFX/251K/335K | E251K/T335K | | 90.5 |

As shown in Tables 1-2 and 2-2, the residual activity of CcFX was 27.4% under the conditions of this Example, whereas all of the double variants prepared by combining the single mutations identified in Example 1 had significantly enhanced residual activities. The surfactant resistance of the double variants of CcFX also was enhanced compared to that of the single variants of CcFX in Table 1-2, also confirming that regardless of the type of an amadoriase enzyme, the effect of mutation was accumulated.

EXAMPLE 3-1

Evaluation for Surfactant TTAC

Tetradecyltrimethylammonium chloride (hereinafter indicated with "TTAC") was used in place of the surfactant CTAC used in Example 2 to evaluate the stability of CFP-D. The surfactant resistance of various modified amadoriases was evaluated in accordance with a measurement method for surfactant resistance according to Example 1, although under surfactant treatment conditions in which the amadoriases were each diluted in a 20 mM potassium phosphate buffer solution (pH 7.0) and mixed with 0.04% TTAC. The results are shown in Table 3-1. In this respect, it was confirmed that when the warmed sample was again measured for activity 30 minutes after 2-fold dilution in a BSA solution, there was no change in the activity value.

TABLE 3-1

| Plasmid | Plasmid as Template | Enzyme | Amino Acid Mutation | SEQ ID NO of Oligonucleotide Used | Residual Activity (%) |
|---|---|---|---|---|---|
| pKK223-3-CFP-D | None | CFP-D | None | None | 29.2 |
| pKK223-3-CFP-D1 | pKK223-3-CFP-D | CFP-D1 | E44P | 23.28 | 43.2 |
| pKK223-3-CFP-D2 | pKK223-3-CFP-D1 | CFP-D2 | E44P/E340P | 16.17 | 69.9 |
| pKK223-3-CFP-D3 | pKK223-3-CFP-D2 | CFP-D3 | E44P/N262H/E340P | 5.6 | 85.3 |
| pKK223-3-CFP-D4 | pKK223-3-CFP-D3 | CFP-D4 | E44PA/257C/N262H/E340P | 7.29 | 91.1 |
| pKK223-3-CFP-D5 | pKK223-3-CFP-D4 | CFP-D5 | E44P/E253K/V257C/N262H/E340P | 30.31 | 94.9 |
| pKK223-3-CFP-D6 | pKK223-3-CFP-D5 | CFP-D6 | E44P/E133A/E253K/V257C/N262H/E340P | 18.19 | 96.4 |
| pKK223-3-CFP-D7 | pKK223-3-CFP-D6 | CFP-D7 | E44P/E133A/E253K/V257C/N262H/Q337K/E340P | 32.33 | 100 |

As shown in Table 3-1, the residual activity of CFP-D was 29.2% under the conditions of this Example.

In contrast, all of the multiple variants prepared in Example 2 had significantly enhanced residual activities. More specifically, the residual activity of the double variant in which glutamic acid at position 44 was substituted with proline and glutamic acid at position 340 was substituted with proline was 69.9% and was enhanced compared to that of CFP-D. The residual activity of the triple variant in which asparagine at position 262 was substitutes by histidine in addition to the prior mutation was 85.3% and was further enhanced compared to that of CFP-D. The residual activity of the quadruple variant in which valine at position 257 was substituted with cysteine in addition to the prior mutation was 91.1% and significantly enhanced compared to that of CFP-D. The residual activity of the quintuple variant in which glutamic acid at position 253 was substituted with lysine in addition to the prior mutation was 94.9%; the residual activity of the sextuple variant in which glutamic acid at position 133 was substituted with alanine in addition to the prior mutation was 96.4%; and the residual activity of the septuple variant in which glutamine at position 337 was substituted with lysine in addition to the prior mutation was 100% and was significantly enhanced compared to CFP-D, and there was almost no inactivation of the amadoriase due to TTAC.

Thus, these amino acid substitutions were shown to enhance the resistance of the amadoriases to TTAC.

EXAMPLE 3-2

[Purification of CFP-T7, CFP-D2, and CFP-D7]

Crude enzyme solutions prepared using the crude enzymes CFP-T7, CFP-D2, and CFP-D7 obtained in Examples 1 and 2 were each adsorbed to 4 ml of Q Sepharose Fast Flow resin (from GE Healthcare Co., Ltd.) equilibrated in a 20 mM potassium phosphate buffer solution (pH 8.0); the resin was then washed with 80 ml of the same buffer solution; the protein adsorbed to the resin was subsequently eluted using a 20 mM potassium phosphate buffer solution containing 100 mM NaCl (pH 8.0); and a fraction showing amadoriase activity was recovered.

The obtained fractions exhibiting amadoriase activity were concentrated using Amicon Ultra-15, 30K NMWL (from Millipore Co., Ltd.). Then, the concentrates were applied to HiLoad 26/60 Superdex 200 μg (from GE Healthcare Co., Ltd.) equilibrated in a 20 mM potassium phosphate buffer solution containing 150 mM NaCl (pH 7.0) for elution with the same buffer solution to recover fractions showing amadoriase activity to provide purified preparations of the wild-type and modified amadoriases. SDS-PAGE analysis confirmed that the resultant purified preparations had been purified to single bands.

(Evaluation of for Various Surfactants)

Using various surfactants, the stability of the purified enzymes CFP-T7, CFP-D2, and CFP-D7 obtained as described above was evaluated. The surfactant resistance of the modified amadoriases was evaluated in accordance with a measurement method for surfactant resistance according to Example 1 although under surfactant treatment conditions in which the amadoriases were each diluted in a 20 mM potassium phosphate buffer solution (pH 7.0) and mixed with any of various concentrations of the surfactants. The results are shown in Table 3-2. In this respect, it was confirmed that when the warmed sample was again measured for activity 30 minutes after 2-fold dilution in a BSA solution, there was no change in the activity value.

TABLE 3-2

| Name of Surfactant | Abbreviated Name | Carbon Chain | Addition Concentration | Residual Activity (%) | | |
| --- | --- | --- | --- | --- | --- | --- |
| | | | | CFP-T7 | D2 | D7 |
| Octyltrimethylammonium Bromide | OTAB | 8 | 0.80% | 87.7 | 93.8 | 101.5 |
| Dodecyltrimethylammonium Bromide | DTAB | 12 | 0.30% | 12.2 | 78.1 | 106.1 |
| Tetradecyltrimethylammonium Bromide | TTAB | 14 | 0.04% | 31.7 | 103.1 | 96.6 |
| Octadecyltrimethylammonium Bromide | STAB | 18 | 0.01% | 59.7 | 99.2 | 94.5 |
| Octyltrimethylammonium Chloride | OTAC | 8 | 1.20% | 94.1 | — | 100.0 |
| Tetradecyltrimethylammonium Chloride | TTAC | 14 | 0.04% | 4.1 | 69.9 | 100.0 |
| Hexadecyltrimethylammonium Chloride | CTAC | 16 | 0.04% | 2.3 | 37.1 | 100.0 |
| Octadecyltrimethylammonium Chloride | STAC | 18 | 0.02% | 49.3 | 96.1 | 85.2 |
| Hexadecylpyridinium Bromide | 1-CPB | 16 | 0.04% | 0.7 | 39.6 | 95.3 |
| Dodecylpyridinium Chloride | 1-DPC | 12 | 0.16% | 3.4 | 92.2 | 109.2 |
| Hexadecylpyridinium Chloride | 1-CPC | 16 | 0.04% | 1.4 | 32.4 | 93.1 |
| N-Cetyl-4-methylpyridinium Chloride | 4Me-1-CPC | 16 | 0.04% | 1.5 | 32.5 | 96.9 |
| Benzyldodecyldimethyl ammonium Bromide | BDDAB | 12 | 0.10% | 1.4 | 94.1 | 105.5 |
| Benzyltetradecyldimethyl ammonium Chloride | BDTAC | 14 | 0.04% | 0.7 | 12.1 | 80.0 |
| Benzylcetyldimethyl ammonium Chloride | BCDAC | 16 | 0.04% | 1.4 | 76.8 | 88.3 |
| Tributylhexadecyl phosphonium Bromide | TBCPB | 16 | 0.04% | 3.1 | 83.1 | 76.7 |

As shown in Table 3-2, the activity of CFP-T7 before introducing mutation was drastically reduced by most surfactants except when OTAB and OTAC were used as surfactants. In contrast, the double variant CFP-D2 had more excellent surfactant resistance to all types of the surfactants tested than CFP-T7. The septuple variant CFP-D7 also had more excellent surfactant resistance to all types of the surfactants tested than CFT-T7, and, in most cases, had enhanced surfactant resistance compared to that of the double variant CFP-D2.

As shown in Table 3-2, when OTAB (C8), DTAB (C12), TTAB (C14), and STAB (C18) having carbon chains different in length were used as surfactants, D2 as well as D7 had enhanced surfactant resistance. As such, it is believed that the same applies for surfactants, such as decyltrimethylammonium bromide, whose carbon chain has 10 carbon atoms, and hexadecyltrimethylammonium bromide, whose carbon chain has 16 carbon atoms. The same also applies for OTAC (C8), TTAC (C14), CTAC (C16), and STAC (C18) as chlorides corresponding to the bromides, and the amadoriases of the present invention are believed to have resistance to decyltrimethylammonium chloride, whose carbon chain has 10 carbon atoms, and dodecyltriethylammonium chloride, whose carbon chain has 12 carbon atoms.

As shown in Table 3-2, both D2 and D7 had surfactant resistance, whether the counter ion (Z) was a chloride ion or bromide ion.

As shown in Table 3-2, both D2 and D7 had resistance to not only ammonium ion surfactants but also pyridinium ion surfactants and phosphonium ion surfactants, showing that the surfactant resistance was against cationic surfactants.

Summarizing the above results, the surfactant-resistant amadoriase of the present invention was demonstrated to have a wide surfactant resistance spectrum irrespective of the type of the counter ion of a surfactant, irrespective of chain length, and irrespective of the basic structure of a cationic surfactant.

Summarizing the names and structures of the surfactants used is as follows.

TABLE 3-3

| Surfactant | R1 | R2 | R3 | R4 | Structure |
|---|---|---|---|---|---|
| Octyltrimethylammonium Bromide | 8 | 1 | 1 | 1 | Formula I |
| Dodecyltrimethylammonium Bromide | 12 | 1 | 1 | 1 | |
| Tetradecyltrimethylammonium Bromide | 14 | 1 | 1 | 1 | |
| Octadecyltrimethylammonium Bromide | 18 | 1 | 1 | 1 | |
| Octyltrimethylammonium Chloride | 8 | 1 | 1 | 1 | |

TABLE 3-3-continued

| Tetradecyltrimethylammonium Chloride | 14 | 1 | 1 | 1 | |
|---|---|---|---|---|---|
| Hexadecyltrimethylammonium Chloride | 16 | 1 | 1 | 1 | |
| Octadecyltrimethylammonium Chloride | 18 | 1 | 1 | 1 | |

| Surfactant | R5 | $R^{a1}$ | $n^1$ | $R^{a2}$ | $n^2$ | Structure |
|---|---|---|---|---|---|---|
| Hexadecylpyridinium Bromide | 16 | H | 5 | — | — | Formula II |
| Dodecylpyridinium Chloride | 12 | H | 5 | — | — | |
| Hexadecylpyridinium Chloride | 16 | H | 5 | — | — | |
| N-cetyl-4-methylpyridinium Chloride | 16 | H | 4 | 1 | 1 | |

| Surfactant | R1 | R2 | R3 | R4 | Structure |
|---|---|---|---|---|---|
| Benzyldodecyldimethyl-ammonium Bromide | 12 | 1 | Bn | 1 | Formula I |
| Benzyltetradecyldimethyl-ammonium Chloride | 14 | 1 | Bn | 1 | |
| Benzylcetyldimethyl-ammonium Chloride | 16 | 1 | Bn | 1 | |

| Surfactant | R6 | R7 | R8 | R9 | Structure |
|---|---|---|---|---|---|
| Tributylhexadecyl-phosphonium Bromide | 16 | 4 | 4 | 4 | Formula III |

H represents a hydrogen atom and Bn represents a benzyl group.
The numeral character indicates the carbon chain length of the alkyl group.

EXAMPLE 4

[Evaluation for Surfactant SDS]

The stability of CFP-D was evaluated using sodium dodecyl sulfate (hereinafter indicated with "SDS") in place of the surfactant CTAC used in Example 2. The surfactant resistance of the modified amadoriases was evaluated in accordance with a measurement method for surfactant resistance according to Example 1 although under surfactant treatment conditions in which the amadoriases were each diluted in a 30 mM MES/21 mM Tris buffer solution (pH 6.5) and mixed with 0.04% SDS. The results are shown in Table 4. In this respect, it was confirmed that when the warmed sample was again measured for activity 30 minutes after 2-fold dilution in a BSA solution, there was no change in the activity value.

TABLE 4

| Plasmid | Plasmid as Template | Enzyme | Amino Acid Mutation | SEQ ID NO of Oligonucleotide Used | Residual Activity (%) |
|---|---|---|---|---|---|
| pKK223-3-CFP-T7 | None | CFP-T7 | None | None | 2.76 |
| pKK223-3-CFP-D | None | CFP-D | None | None | 11.3 |
| pKK223-3-CFP-D1 | pKK223-3-CFP-D | CFP-D1 | E44P | 23.28 | 11.1 |
| pKK223-3-CFP-D2 | pKK223-3-CFP-D1 | CFP-D2 | E44P/E340P | 16.17 | 19.2 |
| pKK223-3-CFP-D3 | pKK223-3-CFP-D2 | CFP-D3 | E44P/N262H/E340P | 5.6 | 11.3 |
| pKK223-3-CFP-D4 | pKK223-3-CFP-D3 | CFP-D4 | E44P/V257C/N262H/E340P | 7.29 | 17.1 |
| pKK223-3-CFP-D5 | pKK223-3-CFP-D4 | CFP-D5 | E44P/E253K/V257C/N262H/E340P | 30.31 | 5.07 |
| pKK223-3-CFP-D6 | pKK223-3-CFP-D5 | CFP-D6 | E44P/E133A/E253K/V257C/N262H/E340P | 18.19 | 3.62 |
| pKK223-3-CFP-D7 | pKK223-3-CFP-D6 | CFP-D7 | E44P/E133A/E253K/V257C/N262H/Q337K/E340P | 32.33 | 3.92 |

As shown in Table 4, the residual activity of CFP-T7 was 2.76% under the conditions of this Example.

In contrast, all of the multiple variants prepared in Example 2 had significantly enhanced residual activities. More specifically, the residual activity of the double variant in which glutamic acid at position 44 was substituted with proline and glutamic acid at position 340 was substituted with proline was 19.2% and was enhanced compared to that of CFP-T7. The residual activity of the triple variant in which asparagine at position 262 was substitutes by histidine in addition to the prior mutation was 11.3% and was further enhanced compared to that of CFP-T7. The residual activity of the quadruple variant in which valine at position 257 was substituted with cysteine in addition to the prior mutation was 17.1% and enhanced compared to that of CFP-T7. The residual activity of the quintuple variant in which glutamic acid at position 253 was substituted with lysine in addition to the prior mutation was 5.07%; the residual activity of the sextuple variant in which glutamic acid at position 133 was substituted with alanine in addition to the prior mutation was 3.62%; the residual activity of the septuple variant in which glutamine at position 337 was substituted with lysine in addition to the prior mutation was 3.92% and was enhanced compared to CFP-T7.

Thus, these amino acid substitutions were shown to enhance the resistance of the amadoriases to SDS.

EXAMPLE 5

Measurement of Fructosyl Peptide Sample Under Mixing of Surfactant

The purified enzyme of CFP-T7 and CFP-D7 obtained in Example 3-2 was used to measure a sample as shown below. The activity values of CFP-T7 and CFP-D7 were determined using (reagent 1) adjusted to pH 7.0 with αFVH at a final concentration of 5 mM as a substrate according to the method for measuring amadoriase activity.

(11) Preparation of Fructosyl Peptide Sample (Reagent 4) αFVH (125 mg) was dissolved in ion-exchanged water, the volume of the solution was fixed to 10 ml, and thereby a 30 mM substrate solution was obtained. In addition, the resultant was diluted by 1/714 with a CTAC solution to provide a 42 μM αFVH/0% to 0.2% CTAC solution.

(12) Measurement of Fructosyl Peptide Sample (Reagent 5)

0.21 mM DA-64 sodium (N-(Carboxymethylaminocarbonyl)-4,4'-bis(dimethylamino)diphenylamine, from Wako Pure Chemical Industries Ltd.

20 mM Potassium phosphate buffer solution (pH 7.0)

(Reagent 6)

6.7 U/ml CFP-T7 or CFP-D7

19 U/ml Peroxidase (from Kikkoman Corporation)

20 mM Potassium phosphate buffer solution (pH 7.0)

(Reagent 6) (50 μl) was added to a mixed solution of 135 μl of (reagent 5) warmed at 37° C. for 5 minutes in advance and 25 μl of the sample prepared in (11) above to start reaction, and absorbance at a wavelength of 751 nm after reaction at 37° C. for 5 minutes was measured using an automated analyzer, Bio Majesty JCA-BM1650 (from JEOL Ltd.). Absorbance (reagent blank) at a wavelength of 751 nm measured by a similar operation for (reagent 4) prepared using ion-exchanged water in place of the substrate solution was used as a control to calculate the amount of change in absorbance (difference) when each sample was measured, using the following equation. The final concentration of a colorimetric substrate, DA-64, was 0.15 mM; the final concentration of αFVH in the case of the presence of a substrate was 5 μM; and the length (optical path) of the cell used for absorbance measurement was 1 cm.

Amount of change in absorbance=$\Delta Aes - Ae0$ $\Delta Aes$: absorbance after a lapse of 5 minutes from reaction initiation $Ae0$: absorbance after a lapse of 5 minutes from reaction initiation when the control solution was added The amount of change in absorbance when αFVH/0% to 0.2% CTAC were used as samples was calculated. The results are shown in Table 5.

TABLE 5

Amount of Change in Absorbance at Wavelength of 751 nm under Mixing of Each Concentration of CTAC

| | Mixing of CTAC (%) | | | | | | | | |
|---|---|---|---|---|---|---|---|---|---|
| | 0 | 0.005 | 0.01 | 0.02 | 0.04 | 0.06 | 0.08 | 0.1 | 0.14 | 0.2 |
| Enzyme CFP-T7 | 0.150 | 0.111 | 0.077 | 0.031 | 0.005 | (Not carried out) | | | | |
| Enzyme CFP-D7 | 0.150 | 0.152 | 0.147 | 0.140 | 0.131 | 0.091 | 0.083 | 0.073 | 0.068 | 0.069 |

As shown in Table 5, under the conditions of this Example, the amount of change in the absorbance of CFP-T7 under the mixing of 0% CTAC was 0.150 and the amount of change in the absorbance of CFP-T7 under the mixing of 0.005% CTAC was 0.111. In addition, the amount of change in the absorbance of CFP-T7 under the mixing of 0.01% CTAC was 0.077; the amount of change in the absorbance of CFP-T7 under the mixing of 0.02% CTAC was 0.031; and the amount of change in the absorbance of CFP-T7 under the mixing of 0.04% CTAC decreased to 0.005, showing that a higher concentration of CTAC decreased the amount of change in absorbance.

In contrast, the amount of change in the absorbance of CFP-D7 under the mixing of 0.02% CTAC was 0.140 and the amount of change in the absorbance of CFP-D7 under the mixing of 0.2% CTAC was 0.069. That is, whereas the mixing of more CTAC decreased the amount of change in the absorbance of CFP-T7, it suppressed a decrease in the amount of change in the absorbance of CFP-D7; the presence of 0.1% or more CTAC made the amount of change in the absorbance of CFP-D7 constant. The diminution in the amount of change in absorbance was large until the CTAC concentration reached 1.3 mM (0.04%) as the critical micelle concentration thereof; however, the concentration exceeding the critical micelle concentration decreased a change in effect on the amadoriase. Thus, CFP-D7 was found to be stably present under the mixing of a high concentration of CTAC, enabling the measurement of αFVH.

EXAMPLE 6

[Quantification of Fructosyl Peptide Sample Under Mixing of Surfactant]

Using the purified enzymes of CFP-T7 and CFP-D7, the linearity of αFVH measurement values was compared in the range of 0.5 to 3 μM under the mixing of CTAC.

Figure 4:
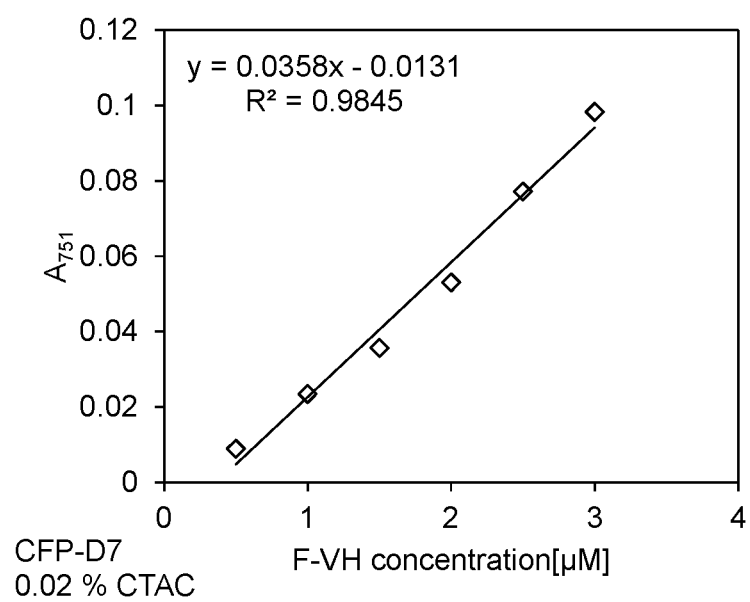
FIG. 4 shows the measurement results of αFVH by using CFP-D7 in the presence of 0.02% CTAC in a mixture.
Figure 5:
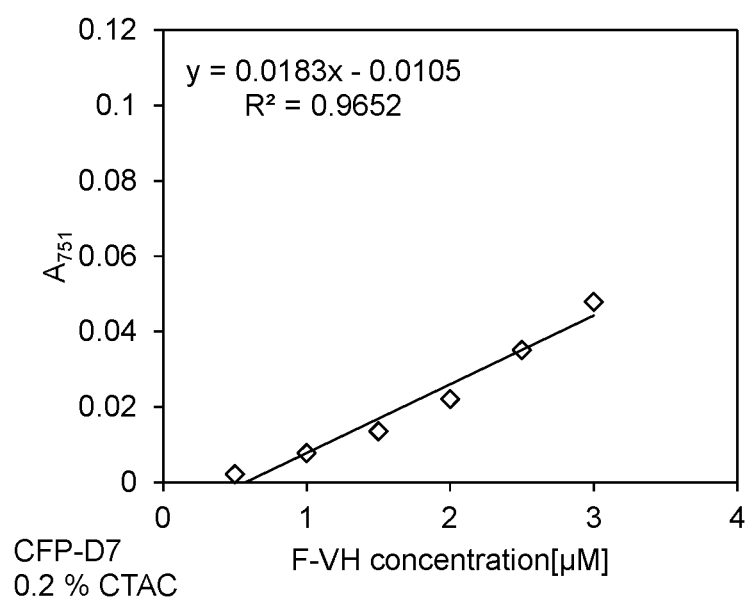
FIG. 5 shows the measurement results of αFVH by using CFP-D7 in the presence of 0.2% CTAC in a mixture.

For CFP-T7, the amount of change in absorbance was measured as in Example 5 under conditions of mixing 0.01% or 0.02% CTAC and further using αFVH at 4.2 μM, 8.4 μM, 13 μM, 17 μM, 21 μM, or 25 μM, i.e., at a final concentration of 0.5 μM, 1.0 μM, 1.5 μM, 2.0 μM, 2.5 M, or 3.0 μM to calculate a correlation coefficient. Similarly, for CFP-D7, the amount of change in absorbance was measured as in Example 5 under conditions of mixing 0.02% or 0.2% CTAC and using the same concentrations of αFVH to calculate a correlation coefficient. The results are shown in Table 6, and the correlation data are shown in FIGS. 2, 3, 4, and 5. FIG. 2 shows the results of measuring αFVH using CFP-T7 under the mixing of 0.01% CTAC; FIG. 3 shows the results of measuring αFVH using CFP-T7 under the mixing of 0.02% CTAC; FIG. 4 shows the results of measuring αFVH using CFP-D7 under the mixing of 0.02% CTAC; and FIG. 5 shows the results of measuring αFVH using CFP-D7 under the mixing of 0.2% CTAC.

TABLE 6

Correlation Coefficient under Mixing of Each Concentration of CTAC

| Mixing of CTAC (%) | 0.01 | 0.02 | 0.2 |
|---|---|---|---|
| Enzyme CFP-T7 | 0.924 | 0.675 | (Not carried out) |
| Enzyme CFP-D7 | (Not carried out) | 0.985 | 0.965 |

As shown in Table 6, under the conditions of this Example, the correlation coefficient of 0.5 µM to 3.0 µM αFVH for CFP-T7 was as high as 0.924 under the mixing of 0.01% CTAC but as low as 0.625 under the mixing 0.02% CTAC. In contrast, when CFP-D7 was used, the correlation coefficient of 0.5 µM to 3.0 µM αFVH indicated a linearity as high as 0.965 even under the mixing of 0.2% CTAC.

According to the package insert of sank HbA1c (from Ark Ray Inc.) as a HbA1c measurement kit for an enzyme method, a whole blood specimen is reacted in a state diluted by 1/416 with an amadoriase. For example, when the HbA1c with an NGSP value is 6.5%, the whole Hb concentration is 141 to 150 g/l, and the blood sample is measured by dilution by 1/416, the concentration of αFVH excised by protease is 0.50 to 0.53 µM. The actual border line of the HbA1c value for diabetic diagnosis is 6.5% (NGSP). Thus, CFP-D7 can be sufficiently used in the actual measurement of HbA1c, and can be said to be capable of being used in combination with, for example, CTAC to increase measurement sensitivity.

EXAMPLE 7

[Evaluation of Surfactant Resistance of Various Amadoriases]

To provide a composition for measuring glycated hemoglobin, containing an amadoriase capable of having activity remaining even in the presence of a surfactant, preferably an ionic surfactant, an amadoriase derived from the genus *Coniochaeta* was modified as described above to enhance the surfactant resistance thereof. It is not known whether or not HbA1c can be measured in the presence of an ionic surfactant for an amadoriase other than the amadoriase derived from the genus *Coniochaeta*. Accordingly, the measurement of αFVH was attempted by combining a fructosyl peptide oxidase derived from *Phaeosphaeria nodorum* or a ketoamine oxidase derived from *Neocosmospora vasinfecta* with an ionic surfactant.

1. Production and Purification of Fructosyl Peptide Oxidase Derived from *Phaeosphaeria* nodorum SEQ ID NO: 40 shows the amino acid sequence of fructosyl peptide oxidase derived from *Phaeosphaeria nodorum* (hereafter referred to as "PnFX") (see Biotechnology and Bioengineering, 106, 358-366, 2010). The gene (SEQ ID NO: 44) encoding the amino acid sequence as shown in SEQ ID NO: 40 was obtained via total synthesis of cDNA by a conventional technique of PCR of a gene fragment. The NdeI site and the BamHI were added to the 5' terminus and the 3' terminus of SEQ ID NO: 40, respectively. Further, the full-length amino acid sequence that is deduced based on the cloned gene sequence was confirmed to be consistent with the PnFX sequence as shown in FIG. 1. Subsequently, in order to express the gene shown in SEQ ID NO: 44 in *E. coli*, the following procedures were performed. The gene fully synthesized above was treated with two types of restriction enzymes, NdeI and BamHI (manufactured by Takara Bio Inc.) and inserted into the NdeI-BamHI site of the pET-22b(+) vector (manufactured by Novagen, Inc.). Thus, the recombinant plasmid pET22b-PnFX was obtained. Strains of *E. coli* BL21 (DE3) were transformed under the conditions as described above to obtain a strain of *E. coli* (DE3) (pET22b-PnFX).

The strains of *E. coli* BL21 (DE3) (pET22b-PnFX) capable of producing PnFX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The prepared crude enzyme solution containing PnFX was purified in accordance with the method described in the non-patent document (Biotechnology and Bioengineering, 106, 358-366, 2010). More specifically, the crude enzyme solution was fractionated with ammonium sulfate, dialyzed against a 10 mM potassium phosphate buffer (pH8.0), purified via anion-exchange chromatography (Q Sepharose Fast Flow was used in Example 2), and then purified via gel filtration chromatography (HiLoad 26/600 Sueprdex 200 was used in Example 2). The obtained fraction was analyzed by SDS-PAGE to confirm that the fraction was sufficiently purified, so that no other contaminating proteins were present therein. The fraction was designated to be a purified sample of PnFX.

2. Production and Purification of Ketoamine Oxidase Derived from *Neocosmospora vasinfecta*

SEQ ID NO: 38 is the amino acid sequence of a ketoamine oxidase derived from *Neocosmospora vasinfecta* (NvFX), and the activity of NvFX has been identified by expressing a recombinant plasmid, pET22b-NvFX, into which the gene (SEQ ID NO: 45) encoding the amino acid sequence of SEQ ID NO: 38 is inserted, in *Escherichia coli* (see International Publication No. WO 2012/18094). *Escherichia coli* strain BL21 (DE3) was transformed as in Example 1, and the obtained *Escherichia coli* strain BL21 (DE3) (pET22b-NvFX) was used and cultured by the above method and a crude enzyme solution of NvFX was prepared.

The prepared crude enzyme solution was allowed to adsorb to Q Sepharose Fast Flow resin (manufactured by GE Healthcare) equilibrated with a 10 mM potassium phosphate buffer (pH8.0), the resin was washed with a 10 mM potassium phosphate buffer (pH8.0) containing 20 mM NaCl, and NvFX adsorbed to the resin was then eluted and collected with the aid of a 10 mM potassium phosphate buffer (pH8.0) containing 300 mM NaCl.

The obtained crude enzyme solution of NvFX was applied to HiLoad 26/60 Superdex 200 column equilibrated in a 20 mM MES-NaOH buffer solution containing 150 mM NaCl (pH 7.0) to elute NvFX with the same buffer solution to recover a fraction showing fructosyl amino acid oxidase activity (amadoriase activity). The resultant fraction was analyzed by SDS-PAGE to confirm that the fraction was sufficiently purified, so that no other contaminating proteins were present therein, and was used as a purified preparation of NvFX.

The purified preparations of amadoriases obtained as described above were used as samples to measure αFVH under the mixing of CTAC using PnFX and NvFX as in Example 5. The results are shown in Table 7.

TABLE 7

Amount of Change in Absorbance at Wavelength of 751 nm under Mixing of Each Concentration of CTAC

| | Mixing of CTAC (%) | | | | | |
|---|---|---|---|---|---|---|
| | 0 | 0.01 | 0.02 | 0.04 | 0.06 | 0.1 | 0.2 |
| Enzyme CFP-T7 | 0.150 | 0.077 | 0.031 | 0.005 | (Not carried out) | | |
| Enzyme PnFX | 0.173 | 0.115 | 0.084 | 0.026 | 0.008 | 0.003 | 0.001 |
| Enzyme NvFX | 0.118 | 0.013 | 0.013 | 0.007 | 0.004 | 0.003 | 0.001 |

As shown in Table 7, under the conditions of this Example, the amount of change in the absorbance of PnFX under the mixing of 0% CTAC was 0.173 and the amount of change in the absorbance under the mixing of 0.01% CTAC was 0.115. The amount of change in the absorbance of PnFX under the mixing of 0.02% CTAC was 0.084, whereas the amount of change in the absorbance of CFP-T7 under the mixing thereof was 0.031; and the amount of change in the absorbance of PnFX under the mixing of 0.04% CTAC was 0.026, whereas the amount of change in the absorbance of CFP-T7 under the mixing thereof was 0.005. Thus, PnFX is capable of measuring αFVH as a substrate under the mixing of CTAC at a concentration as high as 0.02% or more.

For NvFX, absorbance was increased under the mixing of 0.02% or less CTAC; however, αFVH could not accurately be measured since the influence of the occurrence of turbidity increased absorbance even in the blank using ion-exchanged water in place of the substrate.

EXAMPLE 8

[Evaluation of Surfactant Resistance of Amadoriase in Presence of any of Buffering Agents]

It was studied whether the surfactant resistance of an amadoriase is enhanced or not when a buffering agent other than a 30 mM MES/21 mM Tris buffering agent (pH 6.5) was used. Using CFP-T7 purified as described above as a sample, the final concentration of CTAC was set at 0.01% to evaluate the surfactant resistance of CFP-T7 according to the measurement method for surfactant resistance in Example 1 in the presence of any of various buffering agents, specifically a phosphate buffering agent containing phosphoric acid and potassium phosphate (pH 7.0), a citrate buffering agent containing citric acid and sodium citrate (pH 6.0), an MES buffering agent containing MES and it sodium salt (pH 7.0), an HEPES buffering agent containing HEPES and its sodium salt (pH 7.0), and an ACES buffering agent containing ACES and its sodium salt (pH 7.0), in place of the 30 mM MES/21 mM Tris buffering agent (pH 6.5). The results are shown in Table 8. In this respect, it was confirmed that when the warmed sample was again measured for activity 30 minutes after 2-fold dilution in a BSA solution, there was no change in the activity value.

TABLE 8

| Buffer Solution | Concentration | CFP-T7 Residual Activity (%) |
|---|---|---|
| Phosphate | 20 mM | 15.1 |
| | 50 mM | 27.2 |
| | 100 mM | 68.3 |
| | 150 mM | 88.5 |
| | 300 mM | 98.4 |
| Citrate | 10 mM | 104.1 |
| | 50 mM | 108.2 |
| | 100 mM | 105.7 |
| MES | 50 mM | 14.3 |
| | 100 mM | 17.6 |
| | 150 mM | 62.9 |
| | 300 mM | 95.8 |
| HEPES | 50 mM | 13.2 |
| | 100 mM | 13.2 |
| | 150 mM | 12.2 |
| | 300 mM | 9.6 |
| ACES | 20 mM | 15.6 |
| | 100 mM | 16.4 |
| | 200 mM | 22.1 |

As shown in Table 8, under the conditions of this Example, the surfactant resistance of CFP-T7 was demonstrated to be enhanced in a manner dependent on the concentration of a buffering agent in the presence of the phosphate buffering agent, the MES buffering agent, or the ACES buffering agent. The citrate buffering agent was particularly useful since inactivation due to the surfactant did not occur even at 10 mM of this agent. The effect of maintaining amadoriase activity was not observed for the HEPES buffering agent. The above results show, surprisingly, that the phosphate buffering agent, the citrate buffering agent, the MES buffering agent, and the ACES buffering agent have the effect of enhancing the surfactant resistance of the amadoriase.

EXAMPLE 9

[Evaluation of Surfactant Resistance of Amadoriase During Addition of Each Stabilizer]

It was studied whether or not the addition of any of various stabilizers enhanced the surfactant resistance of an amadoriase. Phosphoric acid, a tricarboxylic acid (e.g., citric acid), a dicarboxylic acid (e.g., malic acid, maleic acid, citraconic acid, malonic acid, glutaric acid, or tartaric acid), a monocarboxylic acid (e.g., acetic acid), MES, MOPS, MOPSO, or ammonium sulfate was used as a stabilizer. As a Comparative Example, CHES was used. To prevent change in pH when adding the stabilizer, 500 mM HEPES (pH 7.0) was used as a buffer solution; CFP-T7 purified as described above was used as a sample; the final concentration of CTAC was set at 0.01%; and any of the stabilizers was further added to evaluate the surfactant resistance of CFP-T7 according to the measurement method for surfactant resistance in Example 1. The results are shown in Tables 9-1 and 9-2. Using a 500 mM HEPES (pH 7.0) buffering agent and CFP-D2 purified as described above as a sample, any of the stabilizers was further added, and the surfactant resistance of CFP-D2 was evaluated according to the measurement method for surfactant resistance in Example 1 although under more harsh surfactant treatment conditions in which the final concentration of CTAC was set at 0.08% and the treatment temperature at 37° C. The results are shown in Table 9-3. It was confirmed that the pH actually indicated 7.0 when the stabilizer was added. Incidentally, it was confirmed that when the warmed sample was again measured for activity 30 minutes after 2-fold dilution in a BSA solution, there was no change in the activity value.

TABLE 9-1

| Stabilizer | Concentration | CFP-T7 Residual Activity (%) |
|---|---|---|
| None | — | 4.7 |
| Phosphate | 2 mM | 28.1 |
| | 5 mM | 61.6 |
| | 10 mM | 76.8 |
| | 20 mM | 98.6 |
| | 50 mM | 100.0 |
| Citrate | 0.2 mM | 12.2 |
| | 0.5 mM | 30.7 |
| | 2 mM | 87.6 |
| Malate | 2 mM | 12.6 |
| | 5 mM | 35.4 |
| | 10 mM | 74.3 |
| Acetate | 10 mM | 8.9 |
| | 20 mM | 20.7 |
| | 50 mM | 52.4 |
| MES | 10 mM | 19.5 |
| | 20 mM | 54.1 |
| | 40 mM | 103.0 |
| Ammonium Sulfate | 2 mM | 32.7 |
| | 5 mM | 82.3 |
| | 10 mM | 94.2 |

TABLE 9-2

| Stabilizer | Concentration | CFP-T7 Residual Activity (%) |
|---|---|---|
| None | — | 3.1 |
| Maleate | 2 mM | 15.5 |
| | 10 mM | 81.5 |
| Citraconate | 2 mM | 18.5 |
| | 10 mM | 89.1 |
| Malonate | 2 mM | 10.8 |
| | 10 mM | 77.3 |
| Glutarate | 2 mM | 4.5 |
| | 10 mM | 55.9 |
| Tartrate | 2 mM | 5.3 |
| | 10 mM | 70.0 |
| MOPS | 10 mM | 6.5 |
| | 20 mM | 20.6 |
| MOPSO | 10 mM | 9.0 |
| | 20 mM | 23.5 |
| CHES | 20 mM | 3.0 |

TABLE 9-3

| Stabilizer | Concentration | CFP-D2 Residual Activity (%) |
|---|---|---|
| None | — | 9.4 |
| Phosphate | 5 mM | 72.8 |
| Malate | 5 mM | 59.2 |
| MOPS | 20 mM | 42.4 |

Tables 9-1 and 9-2 demonstrated that under the conditions of this Example, the addition of phosphoric acid, citric acid, malic acid, maleic acid, citraconic acid, malonic acid, glutaric acid, tartaric acid, acetic acid, MES, MOPS, MOPSO, or ammonium sulfate as a stabilizer enhanced the surfactant resistance of CFP-T7 in a manner dependent on the concentration of the stabilizer. In particularly, citric acid was found to be capable of enhancing the surface resistance of CFP-T7 even when added at a trace amount of 0.2 mM. As shown in Table 9-3, the addition of phosphoric acid, malic acid, or MOPS as a stabilizer significantly enhanced the surfactant resistance of the purified CFP-D2 enzyme compared to when the stabilizer is absent. It was not known that the stability of an amadoriase to a surfactant can be enhanced by various compounds and this was surprising. In particular, CHES having the following structure:

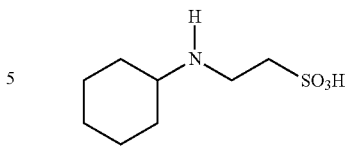

[Formula 9]

did not have any stabilizing action, whereas compounds included in formula (IV)

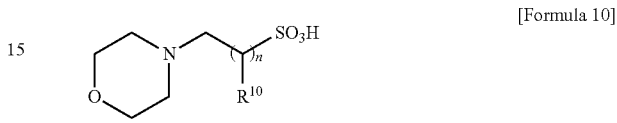

[Formula 10]

[wherein, n may be 0, 1, 2 or 3; each $R^{10}$ independently represent H, OH, —$CH_2OH$ or —COOH], whose structures are highly analogous to the above structure, MES (n=1 and $R^{10}$ represents H), MOPS (n=2 and $R^{10}$ each represent H), MOPSO (n=2 and a plurality of $R^{10}$ each represent OH or H), surprisingly, had an amadoriase-stabilizing action. The above results show that phosphoric acid, tricarboxylic acids, dicarboxylic acids, monocarboxylic acids, and compounds represented by formula (IV), such as MES, MOPS, and MOPSO, have the effect of enhancing the surfactant resistance of an amadoriase. Further, enhanced surfactant resistance was observed regarding CFP-T7, the amadoriase to which the mutation of the present invention was not introduced, as well as regarding CFP-D2, the amadoriase to which the mutation of the present invention was introduced.

The combination of the results of Tables 8 and 9 shows that the amadoriase-stabilizing action of the stabilizer of the present invention is an action different from the amadoriase-stabilizing action of the buffering agent of the present invention. More specifically, it was confirmed from Table 8 that the use of MES at a concentration of 50 mM as a buffering agent of the present invention resulted in a residual activity of CFP-T7 amadoriase of 14.3%, the use thereof at a concentration of 100 mM resulted in a residual activity of the enzyme of 17.6%, and the use thereof at a concentration of 150 mM resulted in a residual activity of the enzyme of 62.9%. In contrast, it was confirmed from Table 9 that the use of MES at a concentration of 10 mM as a stabilizer of the present invention while using HEPES (pH 7.0) merely as a pH buffer agent having no amadoriase-stabilizing action resulted in a residual activity of CFP-T7 amadoriase of 19.5% and the use of MES at a concentration of 20 mM resulted in a residual activity of the enzyme of 54.1%. In other words, MES exhibited an amadoriase-stabilizing action at a concentration as low as 20 mM incapable of sufficiently exerting a buffer capacity, and the confirmed residual activity of the amadoriase surprisingly exceeded the residual activity (Table 8, 17.6%) when MES was used at a concentration of 100 mM as a buffering agent of the present invention. Thus, the amadoriase-stabilizing action of the stabilizer of the present invention is a stabilizing action different from the amadoriase-stabilizing action of the buffering agent of the present invention. The same applies to phosphoric acid and citric acid.

It is believed that the same applies to dicarboxylic acids, MOPS, and MOPSO exhibiting a stabilizing action since these can also be used as buffering agents.

(Evaluation of Surfactant Resistance of PnFX During Addition of Each Stabilizer)

It was studied whether or not the above stabilizers had a surfactant resistance-enhancing effect on amadoriases other than the amadoriase derived from the genus *Coniochaeta*, for example, PnFX. The same stabilizers as those described above were used as stabilizers; 300 mM HEPES (pH 7.0) was used as a buffering agent to prevent a change in pH when the stabilizers was each added; PnFX purified as described above was used as a sample; the final concentration of CTAC was set at 0.04%; and the surfactant resistance of PnFX was evaluated as described above. It was confirmed that the pH actually indicated 7.0 when a stabilizer was added. The results are shown in Table 10. In this respect, it was confirmed that when the warmed sample was again measured for activity 30 minutes after 2-fold dilution in a BSA solution, there was no change in the activity value.

TABLE 10

| Stabilizer | Concentration | PnFX Residual Activity (%) |
| --- | --- | --- |
| None | — | 27.9 |
| Phosphate | 5 mM | 37.5 |
| Citrate | 0.5 mM | 47.3 |
| Malate | 5 mM | 60.4 |
| Acetate | 20 mM | 42.6 |
| MES | 20 mM | 89.6 |
| Ammonium Sulfate | 5 mM | 53.0 |

As shown in Table 10, under the conditions of this Example, the addition of phosphoric acid, citric acid, malic acid, acetic acid, MES, or ammonium sulfate had a surfactant resistance-enhancing effect on PnFX as with CFP-T7. Thus, phosphoric acid, tricarboxylic acids, dicarboxylic acids, monocarboxylic acids, MES, and ammonium sulfate are useful as stabilizers for enhancing the surfactant resistance of a wide variety of amadoriases. Since CFP-T7 has 75% amino acid sequence identity to PnFX, amadoriases having 75% amino acid sequence identity to CFP-T7 can be said to have the above effect.

Sequence Listing Free Text

SEQ ID NO: 1. Amino Acid Sequence of CFP-T7
SEQ ID NO: 2. Gene Sequence for CFP-T7
SEQ ID NO: 3. Amino Acid Sequence of CFP-D
SEQ ID NO: 4. Gene Sequence for CFP-D
SEQ ID NO: 5. N262H Introducing Primer Fw
SEQ ID NO: 6. N262X Introducing Primer Rv
SEQ ID NO: 7. V257C Introducing Primer Fw
SEQ ID NO: 8. V257X Introducing Primer Rv
SEQ ID NO: 9. V257S Introducing Primer Fw
SEQ ID NO: 10. V257T Introducing Primer Fw
SEQ ID NO: 11. E253K Introducing Primer Fw
SEQ ID NO:12. E253X Introducing Primer Rv
SEQ ID NO: 13. E253R Introducing Primer Fw
SEQ ID NO: 14. Q337K Introducing Primer Fw
SEQ ID NO: 15. Q337X Introducing Primer Rv
SEQ ID NO:16. E340P Introducing Primer Fw
SEQ ID NO: 17. E340X Introducing Primer Rv
SEQ ID NO: 18. E133A Introducing Primer Fw
SEQ ID NO: 19. E133X Introducing Primer Rv
SEQ ID NO: 20. E133M Introducing Primer Fw
SEQ ID NO: 21. E133K Introducing Primer Fw
SEQ ID NO: 22. E44P Introducing Primer Fw
SEQ ID NO: 23. E44X Introducing Primer Rv
SEQ ID NO: 24. G256K Introducing Primer Fw
SEQ ID NO: 25. G256R Introducing Primer Fw
SEQ ID NO: 26. E81K Introducing Primer Fw
SEQ ID NO: 27. E81X Introducing Primer Rv
SEQ ID NO: 28. F43Y/E44P Introducing Primer Fw
SEQ ID NO: 29. V257X/N262H Introducing Primer Rv
SEQ ID NO: 30. E253K/V257C Introducing Primer Fw
SEQ ID NO: 31. E253X/V257C/N262H Introducing Primer Rv
SEQ ID NO: 32. Q337K/E340P Introducing Primer Fw
SEQ ID NO: 33. Q337X/E340P Introducing Primer Rv
SEQ ID NO: 34. Amadoriase Derived from *Eupenicillium terrenum*
SEQ ID NO: 35. Ketoamine Oxidase Derived from *Pyrenochaeta* sp.
SEQ ID NO: 36. Ketoamine Oxidase Derived from *Arthrinium* sp.
SEQ ID NO: 37. Ketoamine Oxidase Derived from *Curvularia clavata*
SEQ ID NO: 38. Ketoamine Oxidase Derived from *Neocosmospora vasinfecta*
SEQ ID NO: 39. Fructosyl Amino Acid Oxidase Derived from *Cryptococcus neoformans*
SEQ ID NO: 40. Fructosyl Peptide Oxidase Derived from *Phaeosphaeria nodorum*
SEQ ID NO: 41. Fructosyl Amino Acid Oxidase Derived from *Aspergillus nidulans*
SEQ ID NO: 42. Fructosyl Amino Acid Oxidase Derived from *Ulocladium* sp.
SEQ ID NO: 43. Fructosyl Amino Acid Oxidase Derived from *Penicillium crysogenum*
SEQ ID NO: 44. Gene for Fructosyl Peptide Oxidase Derived from *Phaeosphaeria nodorum*
SEQ ID NO: 45. Gene for Ketoamine Oxidase Derived from *Neocosmospora vasinfecta*
SEQ ID NO: 46. D129K Introducing Primer Fw
SEQ ID NO: 47. D129K Introducing Primer Rv
SEQ ID NO: 48. D132K Introducing Primer Fw
SEQ ID NO: 49. E231K Introducing Primer Fw
SEQ ID NO: 50. E231X Introducing Primer Rv
SEQ ID NO: 51. D232K Introducing Primer Fw
SEQ ID NO: 52. E249K Introducing Primer Fw
SEQ ID NO: 53. E249K Introducing Primer Rv
SEQ ID NO: 54. E249K/V257C Introducing Primer Rv
SEQ ID NO: 55. Gene for Ketoamine Oxidase Derived from *Curvularia clavata*
SEQ ID NO: 56. D129K Introducing Primer Fw for CcFX
SEQ ID NO: 57. D129K Introducing Primer Rv for CcFX
SEQ ID NO: 58. D132K Introducing Primer Fw for CcFX
SEQ ID NO: 59. E133K Introducing Primer Fw for CcFX
SEQ ID NO: 60. E133A Introducing Primer Fw for CcFX
SEQ ID NO: 61. E133X Introducing Primer Rv for CcFX
SEQ ID NO: 62. E229K Introducing Primer Fw for CcFX
SEQ ID NO: 63. D230K Introducing Primer Fw for CcFX
SEQ ID NO: 64. D230X Introducing Primer Rv for CcFX
SEQ ID NO: 65. E247K Introducing Primer Fw for CcFX
SEQ ID NO: 66. E247K Introducing Primer Rv for CcFX
SEQ ID NO: 67. E251K Introducing Primer Fw for CcFX
SEQ ID NO: 68. E251X Introducing Primer Rv for CcFX
SEQ ID NO: 69. E251R Introducing Primer Fw for CcFX
SEQ ID NO: 70. N254K Introducing Primer Fw for CcFX
SEQ ID NO: 71. N254K Introducing Primer Rv for CcFX
SEQ ID NO: 72. T335K Introducing Primer Fw for CcFX
SEQ ID NO: 73. T335K Introducing Primer Rv for CcFX
SEQ ID NO: 74. T335R Introducing Primer Fw for CcFX All publications, patents, and patent applications cited in this application are intended to be incorporated herein by reference in their entirety.

The invention claimed is:

1. A modified amadoriase having improved residual activity (%) 5 minutes after an ionic surfactant is added compared with an amadoriase prior to the modification, and comprising
   (a) the amino acid sequence of SEQ ID No: 1, 3, or 37, said amino acid sequence further having a deletion, insertion, addition, and/or substitution of one to 15 amino acids in the amino acid sequence of SEQ ID No: 1, 3, or 37, or
   (b) an amino acid sequence having an identity of at least 90% with the amino acid sequence of SEQ ID No: 1, 3, or 37, wherein said modified amadoriase comprising the amino acid sequence of (a) or (b) comprises one or more substitution(s) selected from the group consisting of:
   (i) substitution of the amino acid at the position corresponding to position 257 of SEQ ID NO: 1 with cysteine, serine, or threonine,
   (ii) substitution of the amino acid at the position corresponding to position 262 of SEQ ID NO: 1 with histidine,
   (iii) substitution of the amino acid at the position corresponding to position 249 of SEQ ID NO: 1 with lysine, or arginine,
   (iv) substitution of the amino acid at the position corresponding to position 253 of SEQ ID NO: 1 with lysine, or arginine,
   (v) substitution of the amino acid at the position corresponding to position 337 of SEQ ID NO: 1 with lysine, or arginine,
   (vi) substitution of the amino acid at the position corresponding to position 340 of SEQ ID NO: 1 with proline,
   (vii) substitution of the amino acid at the position corresponding to position 232 of SEQ ID NO: 1 with lysine, or arginine,
   (viii) substitution of the amino acid at the position corresponding to position 129 of SEQ ID NO: 1 with lysine, or arginine,
   (ix) substitution of the amino acid at the position corresponding to position 132 of SEQ ID NO: 1 with lysine, or arginine, (x) substitution of the amino acid at the position corresponding to position 133 of SEQ ID NO: 1 with alanine, methionine, lysine, or arginine,
(xi) substitution of the amino acid at the position corresponding to position 44 of SEQ ID NO: 1 with proline,
(xii) substitution of the amino acid at the position corresponding to position 256 of SEQ ID NO: 1 with lysine, or arginine,
(xiii) substitution of the amino acid at the position corresponding to position 231 of SEQ ID NO: 1 with lysine, or arginine, and
(xiv) substitution of the amino acid at the position corresponding to position 81 of SEQ ID NO: 1 with lysine, or arginine.

2. The amadoriase according to claim 1, wherein the ionic surfactant is selected from the group consisting of an anionic surfactant, a cationic surfactant and an amphoteric surfactant.

3. The amadoriase according to claim 1, wherein the amino acid sequence of (a) or (b) comprises substitutions of amino acid residues selected from the group consisting of the following (i) to (ix):
  (i) substitution of the amino acid at the position corresponding to position 44 of SEQ ID NO: 1 with proline and substitution of the amino acid at the position corresponding to-position 340 of SEQ ID NO: 1 with proline;
  (ii) substitution of the amino acid at the position corresponding to position 44 of SEQ ID NO: 1 with proline, substitution of the amino acid at the position corresponding to position 262 of SEQ ID NO: 1 with histidine, and substitution of the amino acid at the position corresponding to position 340 of SEQ ID NO: 1 with proline;
  (iii) substitution of the amino acid at the position corresponding to position 44 of SEQ ID NO: 1 with proline, substitution of the amino acid at the position corresponding to position 257 of SEQ ID NO: 1 with cysteine, substitution of the amino acid at the position corresponding to position 262 of SEQ ID NO: 1 with histidine, and substitution of the amino acid at the position corresponding to position 340 of SEQ ID NO: 1 with proline;
  (iv) substitution of the amino acid at the position corresponding to position 44 of SEQ ID NO: 1 with proline, substitution of the amino acid at the position corresponding to position 257 of SEQ ID NO: 1 with cysteine, substitution of the amino acid at the position corresponding to position 262 of SEQ ID NO: 1 with histidine, substitution of the amino acid at the position corresponding to position 340 of SEQ ID NO: 1 with proline, and substitution of the amino acid at the position corresponding to position 232 of SEQ ID NO: 1 with lysine;
  (v) substitution of the amino acid at the position corresponding to position 44 of SEQ ID NO: 1 with proline, substitution of the amino-acid at the position corresponding to position 257 of SEQ ID NO: 1 with cysteine, substitution of the amino acid at the position corresponding to position 262 of SEQ ID NO: 1 with histidine, substitution of the amino acid at the position corresponding to position 340 of SEQ ID NO: 1 with proline, and substitution of the amino acid at the position corresponding to position 249 of SEQ ID NO: 1 with lysine;
  (vi) substitution of the amino acid at the position corresponding to position 44 of SEQ ID NO: 1 with proline, substitution of the amino acid at the position corresponding to position 253 of SEQ ID NO: 1 with lysine, substitution of the amino acid at the position corresponding to position 257 of SEQ ID NO: 1 with cysteine, substitution of the amino acid at the position corresponding to position 262 of SEQ ID NO: 1 with histidine, and substitution of the amino acid at the position corresponding to position 340 of SEQ ID NO: 1 with proline;
  (vii) substitution of the amino acid at the position corresponding to position 44 of SEQ ID NO: 1 with proline, substitution of the amino acid at the position corresponding to position 253 of SEQ ID NO: 1 with lysine, substitution of the amino acid at the position corresponding to position 257 of SEQ ID NO: 1 with cysteine, substitution of the amino acid at the position corresponding to position 262 of SEQ ID NO: 1 with histidine, substitution of the amino acid at the position corresponding to position 340 of SEQ ID NO: 1 with proline, and substitution of the amino acid at the position corresponding to position 129 of SEQ ID NO: 1 with lysine;
  (viii) substitution of the amino acid at the position corresponding to position 44 of SEQ ID NO: 1 with proline, substitution of the amino acid at the position corresponding to position 133 of SEQ ID NO: 1 with alanine, substitution of the amino acid at the position corresponding to position 253 of SEQ ID NO: 1 with lysine, substitution of the amino acid at the position corresponding to position 257 of SEQ ID NO: 1 with cysteine, substitution of the amino acid at the position corresponding to position 262 of SEQ ID NO: 1 with histidine, and substitution of the amino acid at the position corresponding to position 340 of SEQ ID NO: 1 with proline; and
  (ix) substitution of the amino acid at the position corresponding to position 44 of SEQ ID NO: 1 with proline, substitution of the amino acid at the position corresponding to position 133 of SEQ ID NO: 1 with alanine, substitution of the amino acid at the position corresponding to position 253 of SEQ ID NO: 1 with lysine, substitution of the amino acid at the position corresponding to position 257 of SEQ ID NO: 1 with cysteine, substitution of the amino acid at the position corresponding to position 262 of SEQ ID NO: 1 with histidine, substitution of the amino acid at the position corresponding to position 337 of SEQ ID NO: 1 with lysine, and substitution of the amino acid at the position corresponding to position 340 of SEQ ID NO: 1 with proline.

4. The amadoriase according to claim 1, wherein the amadoriase comprises an amino acid sequence having at least 90% sequence identity with SEQ ID NO: 37 and has at least one of the substitutions of the following (i) to (ix)
  (i) substitution of the amino acid at the position corresponding to position 247 of SEQ ID NO: 37 is substituted with lysine, or arginine;
  (ii) substitution of the amino acid at the position corresponding to position 251 of SEQ ID NO: 37 is substituted with lysine, or arginine;
  (iii) substitution of the amino acid at the position corresponding to position 335 of SEQ ID NO: 37 is substituted with lysine, or arginine;
  (iv) substitution of the amino acid at the position corresponding to position 230 of SEQ ID NO: 37 is substituted with lysine, or arginine;

(v) substitution of the amino acid at the position corresponding to position 129 of SEQ ID NO: 37 is substituted with lysine, or arginine;
(vi) substitution of the amino acid at the position corresponding to position 132 of SEQ ID NO: 37 is substituted with lysine, or arginine;
(vii) substitution of the amino acid at the position corresponding to position 133 of SEQ ID NO: 37 is substituted with alanine, methionine, lysine, or arginine;
(viii) substitution of the amino acid at the position corresponding to position 254 of SEQ ID NO: 37 is substituted with lysine, or arginine; and
(ix) substitution of the amino acid at the position corresponding to position 229 of SEQ ID NO: 37 is substituted with lysine, or arginine.

5. The amadoriase according to claim 4, wherein the amino acid sequence having at least 90% sequence identity with SEQ ID NO: 37 has substitutions of amino acid residues selected from the group consisting of the following (i) to (iv):
(i) substitution of the amino acid at the position corresponding to position 251 of SEQ ID NO: 37 with lysine and substitution of the amino acid at the position corresponding to position 335 of SEQ ID NO: 37 with lysine;
(ii) substitution of the amino acid at the position corresponding to position 132 of SEQ ID NO: 37 with lysine and substitution of the amino acid at the position corresponding to position 335 of SEQ ID NO: 37 with lysine;
(iii) substitution of the amino acid at the position corresponding to position 133 of SEQ ID NO: 37 with alanine and substitution of the amino acid at the position corresponding to position 335 of SEQ ID NO: 37 with lysine; and
(iv) substitution of the amino acid at the position corresponding to position 229 of SEQ ID NO: 37 with lysine and substitution of the amino acid at the position corresponding to position 335 of SEQ ID NO: 37 with lysine.

6. An amadoriase gene encoding the amino acid sequence of claim 1.

7. A recombinant vector comprising the amadoriase gene according to claim 6.

8. An isolated host cell comprising the recombinant vector according to claim 7.

9. A method for producing an amadoriase comprising the following steps:
(i) culturing the host cell according to claim 8;
(ii) expressing an amadoriase gene contained in the host cell; and
(iii) isolating the amadoriase from a culture product.

10. A composition comprising the amadoriase of claim 1, for use in measuring glycated hemoglobin.

* * * * *